US009222143B2

(12) United States Patent
Sebo et al.

(10) Patent No.: US 9,222,143 B2
(45) Date of Patent: *Dec. 29, 2015

(54) MUTANT CYAA POLYPEPTIDES AND POLYPEPTIDE DERIVATIVES SUITABLE FOR THE DELIVERY OF IMMUNOGENIC MOLECULES INTO A CELL

(75) Inventors: Peter Sebo, Prague (CZ); Adriana Osickova, Prague (CZ); Jiri Masin, Uvaly (CZ); Catherine Fayolle, Epinay sur Orge (FR); Jan Krusek, Prague (CZ); Marek Basler, Prague (CZ); Claude Leclerc, Paris (FR); Radim Osicka, Prague (CZ)

(73) Assignees: INSTITUT PASTEUR, Paris (FR); INSTITUTE OF MICROBIOLOGY OF THE ASCR, V.V.I., Prague (CZ); INSTITUTE OF PHYSIOLOGY OF THE ASCR. V.V.I., Prague (CZ)

(*) Notice: Subject to any disclaimer, the term of this patent is extended or adjusted under 35 U.S.C. 154(b) by 0 days.

This patent is subject to a terminal disclaimer.

(21) Appl. No.: 13/257,569

(22) PCT Filed: Mar. 23, 2010

(86) PCT No.: PCT/EP2010/053795
§ 371 (c)(1),
(2), (4) Date: Dec. 2, 2011

(87) PCT Pub. No.: WO2010/136231
PCT Pub. Date: Dec. 2, 2010

(65) Prior Publication Data
US 2012/0071393 A1    Mar. 22, 2012

(30) Foreign Application Priority Data
Mar. 23, 2009    (EP) .................. 09155929

(51) Int. Cl.
*C12N 9/88* (2006.01)
(52) U.S. Cl.
CPC ........... *C12Y 406/01001* (2013.01); *C12N 9/88* (2013.01)

(58) Field of Classification Search
None
See application file for complete search history.

(56) References Cited

U.S. PATENT DOCUMENTS 8,017,132 B2 *    9/2011    Sebo et al. ................ 424/240.1

FOREIGN PATENT DOCUMENTS

WO    WO 2005035557 A2 *    4/2005

OTHER PUBLICATIONS

Basler, et al., "Pore-forming and enzymatic activities of Bordetella pertussis adenylate cyclase toxin synergize in promoting lysis of monocytes," Inf. Immun. 74:2207-14 (2006).*
Masin, et al., "Acylation of lysine 860 allows tight binding and cytotoxicity of Bordetella adenylate cyclase on CD11b-expressing cells," Biochem. 44:12759-66 (2005).*
Sakamoto et al. "Bordetella pertussis Adenylate Cyclase Toxi: structural and functional independence of the catalytic and hemolytic activities" J. Biol. Chem. 267:13598-13602 (1992).*
Guermonprez, et al. "Bordetella pertussis adenylate cyclase toxin: a vehicle to deliver CD8-positive T-cell epitopes into antigen presenting cells" Methods in Enz. 326:527-542 (2000).*

* cited by examiner

*Primary Examiner* — Julie Ha
*Assistant Examiner* — Kristina M Hellman
(74) *Attorney, Agent, or Firm* — Law Office of Salvatore Arrigo and Scott Lee, LLP

(57) ABSTRACT

A polypeptide comprises a mutated *Bordetella pertussis* CyaA (SEQ ID NO:1), *Bordetella parapertussis* CyaA (SEQ ID NO:7), *Bordetella hinzii* CyaA (SEQ ID NO:8), or *Bordetella bronchiseptica* CyaA (SEQ ID NO:9), or a fragment thereof lacking all or part of the N-terminal catalytic domain of the CyaA, or a polypeptide having at least 95% sequence identity with SEQ ID NOS: 1, 7, 8, or 9. The glutamic acid residue at position 570 of SEQ ID NO: 1, 7, 8 or at position 569 of SEQ ID NO:9 has been substituted by a conservative amino acid residue. The lysine residue at position 860 of SEQ ID NO: 1, 7, 8 or at position 859 of SEQ ID NO:9 has been substituted by a conservative amino acid residue. The polypeptide retains the binding activity of native CyaA to CD11b expressing cell, and has a pore-forming activity which is reduced or suppressed as compared to that of the native CyaA toxin.

11 Claims, 23 Drawing Sheets

Figure 1:
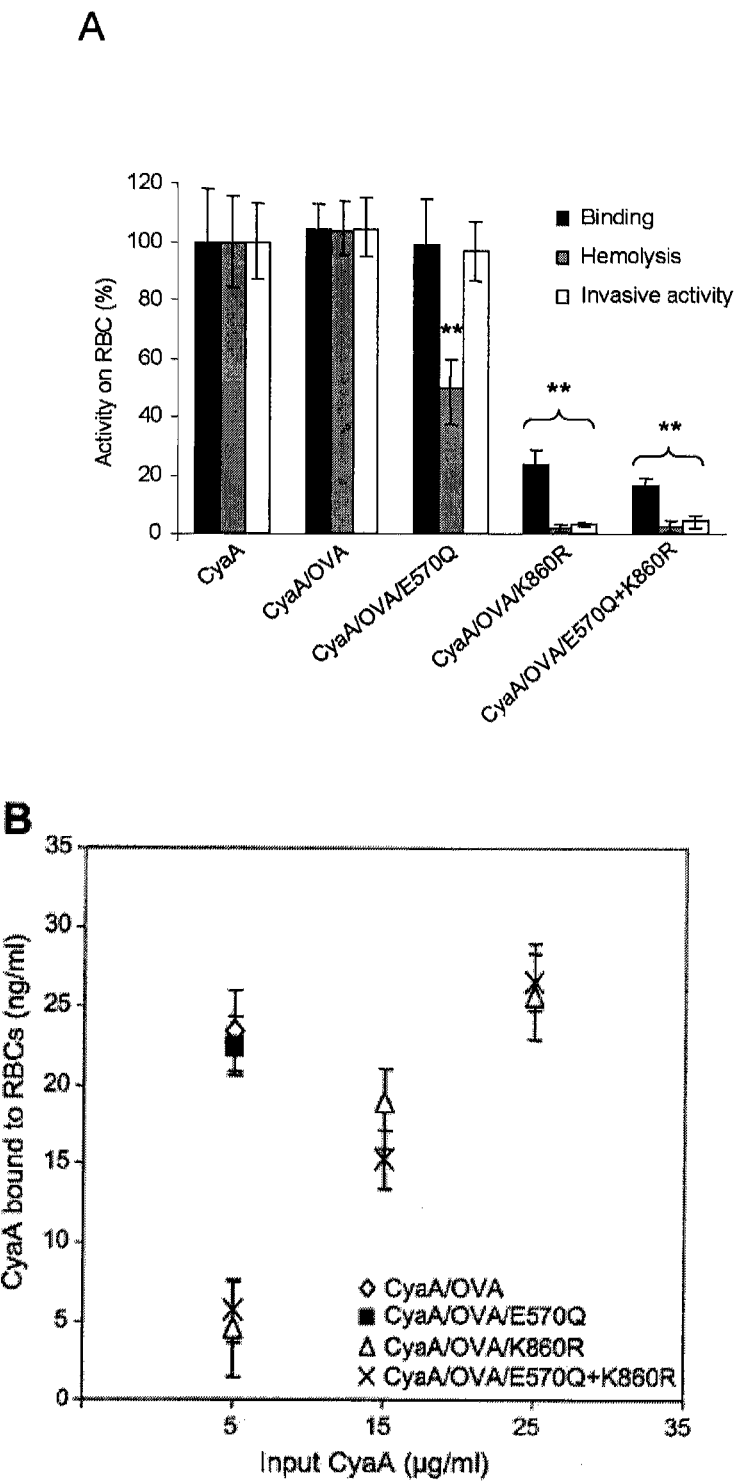
Figure 1:
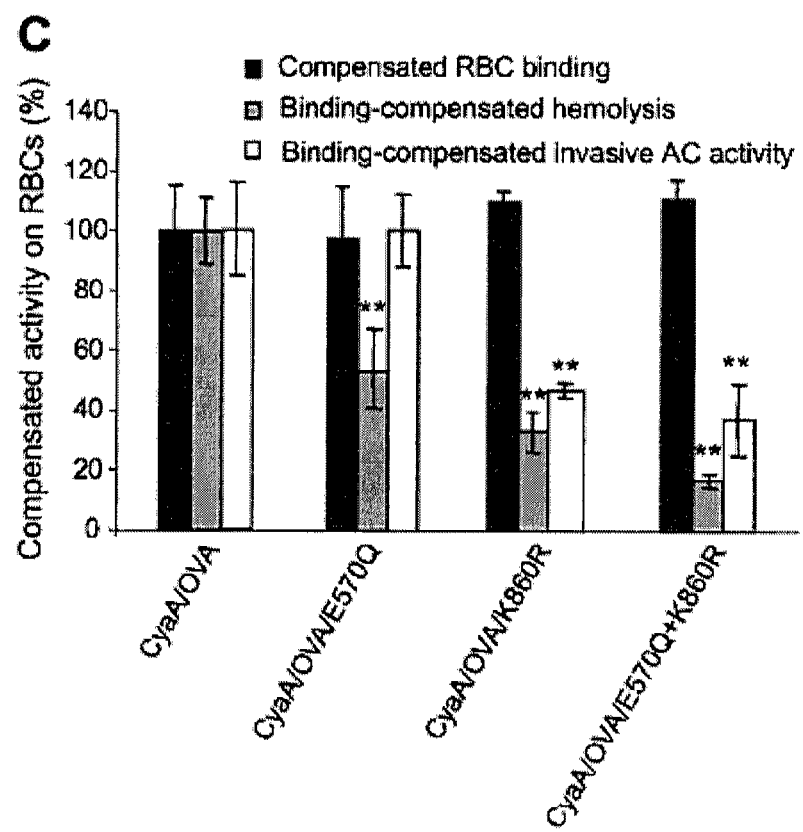

```
   1  MQQSHQAGYA  NAADRESGIP  AAVLDGIKAV  AKEKNATLMF  RLVNPHSTSL  IAEGVATKGL
  61  GVHAKSSDWG  LQAGYIPVNP  NLSKLFGRAP  EVIARADNDV  NSSLAHGHTA  VDLTLSKERL
 121  DYLRQAGLVT  GMADGVVASN  HAGYEQFEFR  VKETSDGRYA  VQYRRKGGDD  FEAVKVIGNA
 181  AGIPLTADID  MFAIMPHLSN  FRDSARSSVT  SGDSVTDYLA  RTRRAASEAT  GGLDRERIDL
 241  LWKIARAGAR  SAVGTEARRQ  FRYDGDMNIG  VITDFELEVR  NALNRRAHAV  GAQDVVQHGT
 301  EQNNPFPEAD  EKIFVVSATG  ESQMLTRGQL  KEYIGQQRGE  GYVFYENRAY  GVAGKSLFDD
 361  GLGAAPGVPS  GRSKFSPDVL  ETVPASPGLR  RPSLGAVERQ  DSGYDSLDGV  GSRSFSLGEV
 421  SDMAAVEAAE  LEMTRQVLHA  GARQDDAEPG  VSGASAHWGQ  RALQGAQAVA  AAQRLVHAIA
 481  LMTQFGRAGS  TNTPQEAASL  SAAVFGLGEA  SSAVAETVSG  FFRGSSRWAG  GFGVAGGAMA
 541  LGGGIAAAVG  AGMSLTDDAP  AGQKAAAGAE  IALQLTGGTV  ELASSIALAL  AAARGVTSGL
 601  QVAGASAGAA  AGALAAALSP  MEIYGLVQQS  HYADQLDKLA  QESSAYGYEG  DALLAQLYRD
 661  KTAAEGAVAG  VSAVLSTVGA  AVSIAAAASV  VGAPVAVVTS  LLTGALNGIL  RGVQQPIIEK
 721  LANDYARKID  ELGGPQAYFE  KNLQARHEQL  ANSDGLRKML  ADLQAGWNAS  SVIGVQTTEI
 781  SKSALELAAI  TGNADNLKSV  DVFVDRFVQG  ERVAGQPVVL  DVAAGGIDIA  SRKGERPALT
 841  FITPLAAPGE  EQRRRTKTGK  SEFTTFVEIV  GKQDRWRIRD  GAADTTIDLA  KVVSQLVDAN
 901  GVLKHSIKLD  VIGGDGDDVV  LANASRIHYD  GGAGTNTVSY  AALGRQDSIT  VSADGERFNV
 961  RKQLNNANVY  REGVATQTTA  YGKRTENVQY  RHVELARVGQ  VVEVDTLEHV  QHIIGGAGND
1021  SITGNAHDNF  LAGGSGDDRL  DGGAGNDTLV  GGEGQNTVIG  GAGDDVFLQD  LGVWSNQLDG
1081  GAGVDTVKYN  VHQPSEERLE  RMGDTGIHAD  LQKGTVEKWP  ALNLFSVDHV  KNIENLHGSR
1141  LNDRIAGDDQ  DNELWGHDGN  DTIRGRGGDD  ILRGGLGLDT  LYGEDGNDIF  LQDDETVSDD
1201  IDGGAGLDTV  DYSAMIHPGR  IVAPHEYGFG  IEADLSREWV  RKASALGVDY  YDNVRNVENV
1261  IGTSMKDVLI  GDAQANTLMG  QGGDDTVRGG  DGDDLLFGGD  GNDMLYGDAG  NDTLYGGLGD
1321  DTLEGGAGND  WFGQTQAREH  DVLRGGDGVD  TVDYSQTGAH  AGIAAGRIGL  GILADLGAGR
1381  VDKLGEAGSS  AYDTVSGIEN  VVGTELADRI  TGDAQANVLR  GAGGADVLAG  GEGDDVLLGG
1441  DGDDQLSGDA  GRDRLYGEAG  DDWFFQDAAN  AGNLLDGGDG  RDTVDFSGPG  RGLDAGAKGV
1501  FLSLGKGFAS  LMDEPETSNV  LRNIENAVGS  ARDDVLIGDA  GANVLNGLAG  NDVLSGGAGD
1561  DVLLGDEGSD  LLSGDAGNDD  LFGGQGDDTY  LFGVGYGHDT  IYESGGGHDT  IRINAGADQL
1621  WFARQGNDLE  IRILGTDDAL  TVHDWYRDAD  HRVEIIHAAN  QAVDQAGIEK  LVEAMAQYPD
1681  PGAAAAPPA   ARVPDTLMQS  LAVNWR
```

Figure 6

```
   1 MQQSHQAGYA NAADRESGIP AAVLDGIKAV AKEKNATLMF RLVNPHSTSL IAEGVATKGL
  61 GVHAKSSDWG LQAGYIPVNP NLSKLFGRAP EVIARADNDV NSSLAHGHTA VDLTLSKERL
 121 DYLRQAGLVT GMADGVVASN HAGYEQFEFR VKETSDGRYA VQYRRKGGDD FEAVKVIGNA
 181 AGIPLTADID MFAIMPHLSN FRDSARSSVT SGDSVTDYLA RTRRAASEAT GGLDRERIDL
 241 LWKIARAGAR SAVGTEARRQ FRYDGDMNIG VITDFELEVR NALNRRAHAV GAQDVVQHGT
 301 EQNNPFPEAD EKIFVVSATG ESQMLTRGQL KEYIGQQRGE GYVFYENRAY GVAGKSLFDD
 361 GLGAAPGVPS GRSKFSPDVL ETVPASPGLR RPSLGAVERQ DSGYDSLDGV GSRSFSLGEV
 421 SDMAAVEAAE LEMTRQVLHA GARQDDAEPG VSGASAHWGQ RALQGAQAVA AAQRLVHAIA
 481 LMTQFGRAGS TNTPQEAASL SAAVFGLGEA SSAVAETVSG FFRGSSRWAG GFGVAGGAMA
 541 LGGGIAAAVG AGMSLTDDAP AGQKAAAGAQ IALQLTGGTV ELASSIALAL AAARGVTSGL
 601 QVAGASAGAA AGALAAALSP MEIYGLVQQS HYADQLDKLA QESSAYGYEG DALLAQLYRD
 661 KTAAEGAVAG VSAVLSTVGA AVSIAAAASV VGAPVAVVTS LLTGALNGIL RGVQQPIIEK
 721 LANDYARKID ELGGPQAYFE KNLQARHEQL ANSDGLRKML ADLQAGWNAS SVIGVQTTEI
 781 SKSALELAAI TGNADNLKSV DVFVDRFVQG ERVAGQPVVL DVAAGGIDIA SRKGERPALT
 841 FITPLAAPGE EQRRRTKTGR SEFTTFVEIV GKQDRWRIRD GAADTTIDLA KVVSQLVDAN
 901 GVLKHSIKLD VIGGDGDDVV LANASRIHYD GGAGTNTVSY AALGRQDSIT VSADGERFNV
 961 RKQLNNANVY REGVATQTTA YGKRTENVQY RHVELARVGQ VVEVDTLEHV QHIIGGAGND
1021 SITGNAHDNF LAGGSGDDRL DGGAGNDTLV GGEGQNTVIG GAGDDVFLQD LGVWSNQLDG
1081 GAGVDTVKYN VHQPSEERLE RMGDTGIHAD LQKGTVEKWP ALNLFSVDHV KNIENLHGSR
1141 LNDRIAGDDQ DNELWGHDGN DTIRGRGGDD ILRGGLGLDT LYGEDGNDIF LQDDETVSDD
1201 IDGGAGLDTV DYSAMIHPGR IVAPHEYGFG IEADLSREWV RKASALGVDY YDNVRNVENV
1261 IGTSMKDVLI GDAQANTLMG QGGDDTVRGG DGDDLLFGGD GNDMLYGDAG NDTLYGGLGD
1321 DTLEGGAGND WFGQTQAREH DVLRGGDGVD TVDYSQTGAH AGIAAGRIGL GILADLGAGR
1381 VDKLGEAGSS AYDTVSGIEN VVGTELADRI TGDAQANVLR GAGGADVLAG GEGDDVLLGG
1441 DGDDQLSGDA GRDRLYGEAG DDWFFQDAAN AGNLLDGGDG RDTVDFSGPG RGLDAGAKGV
1501 FLSLGKGFAS LMDEPETSNV LRNIENAVGS ARDDVLIGDA GANVLNGLAG NDVLSGGAGD
1561 DVLLGDEGSD LLSGDAGNDD LFGGQGDDTY LFGVGYHDT IYESGGGHDT IRINAGADQL
1621 WFARQGNDLE IRILGTDDAL TVHDWYRDAD HRVEIIHAAN QAVDQAGIEK LVEAMAQYPD
1681 PGAAAAPPA ARVPDTLMQS LAVNWR
```

Figure 7

```
   1 MQQSHQAGYA NAADRESGIP AAVLDGIKAV AKEKNATLMF RLVNPHSTSL IAEGVATKGL
  61 GVHAKSSDWG LQAGYIPVNP NLSKLFGRAP EVIARADNDV NSSLAHGHTA VDLTLSKERL
 121 DYLRQAGLVT GMADGVVASN HAGYEQFEFR VKETSDGRYA VQYRRKGGDD FEAVKVIGNA
 181 AGIPLTADGS IDMFAIMPHL SNFRDSARSS VTSGDSVTDY LARTRRAASE ATGGLDRERI
 241 DLLWKIARAG ARSAVGTEAR RQFRYDGDMN IGVITDFELE VRNALNRRAH AVGAQDVVQH
 301 GTEQNNPFPE ADEKIFVVSA TGESQMLTRG QLKEYIGQQR GEGYVFYENR AYGVAGKSLF
 361 DDGLGAAPGV PSGRSKFSPD VLETVPASPG LRRPSLGAVE RQDSGYDSLD GVGSRSFSLG
 421 EVSDMAAVEA AELEMTRQVL HAGARQDDAE PGVSGASAHW GQRALQGAQA VAAAQRLVHA
 481 IALMTQFGRA GSTNTPQEAA SLSAAVFGLG EASSAVAETV SGFFRGSSRW AGGFGVAGGA
 541 MALGGGIAAA VGAGMSLTDD APAGQKAAAG AQIALQLTGG TVELASSIAL ALAAARGVTS
 601 GLQVAGASAG AAAGALAAAL SPMEIYGLVQ QSHYADQLDK LAQESSAYGY EGDALLAQLY
 661 RDKTAAEGAV AGVSAVLSTV GAAVSIAAAA SVVGAPVAVV TSLLTGALNG ILRGVQQPII
 721 EKLANDYARK IDELGGPQAY FEKNLQARHE QLANSDGLRK MLADLQAGWN ASSVIGVQTT
 781 EISKSALELA AITGNADNLK SVDVFVDRFV QGERVAGQPV VLDVAAGGID IASRKGERPA
 841 LTFITPLAAP GEEQRRRTKT GRSEFTTFVE IVGKQDRWRI RDGAADTTID LAKVVSQLVD
 901 ANGVLKHSIK LDVIGGDGDD VVLANASRIH YDGGAGTNTV SYAALGRQDS ITVSADGERF
 960 NVRKQLNNAN VYREGVATQT TAYGKRTENV QYRHVELARV GQVVEVDTLE HVQHIIGGAG
1021 NDSITGNAHD NFLAGGSGDD RLDGGAGNDT LVGGEGQNTV IGGAGDDVFL QDLGVWSNQL
1081 DGGAGVDTVK YNVHQPSEER LERMGDTGIH ADLQKGTVEK WPALNLFSVD HVKNIENLHG
1141 SRLNDRIAGD DQDNELWGHD GNDTIRGRGG DDILRGGLGL DTLYGEDGND IFLQDDETVS
1201 DDIDGGAGLD TVDYSAMIHP GRIVAPHEYG FGIEADLSRE WVRKASALGV DYYDNVRNVE
1261 NVIGTSMKDV LIGDAQANTL MGQGGDDTVR GGDGDDLLFG GDGNDMLYGD AGNDTLYGGL
1321 GDDTLEGGAG NDWFGQTQAR EHDVLRGGDG VDTVDYSQTG AHAGIAAGRI GLGILADLGA
1381 GRVDKLGEAG SSAYDTVSGI ENVVGTELAD RITGDAQANV LRGAGGADVL AGGEGDDVLL
1441 GGDGDDQLSG DAGRDRLYGE AGDDWFFQDA ANAGNLLDGG DGRDTVDFSG PGRGLDAGAK
1501 GVFLSLGKGF ASLMDEPETS NVLRNIENAV GSARDDVLIG DAGANVLNGL AGNDVLSGGA
1561 GDDVLLGDEG SDLLSGDAGN DDLFGGQGDD TYLFGVGYGH DTIYESGGGH DTIRINAGAD
1621 QLWFARQGND LEIRILGTDD ALTVHDWYRD ADHRVEIIHA ANQAVDQAGI EKLVEAMAQY
1681 PDPGAAAAAP PAARVPDTLM QSLAVNWR
```

Figure 8

| | | | | | |
|---|---|---|---|---|---|
| 1 | MQQSHQAGYA | NAADRESGIP | AAVLDGIKAV | AKEKNATLMF | RLVNPHSTSL | IAEGVATKGL |
| 61 | GVHAKSSDWG | LQAGYIPVNP | NLSKLFGRAP | EVIARADNDV | NSSLAHGHTA | VDLTLSKERL |
| 121 | DYLRQAGLVT | GMADGVVASN | HAGYEQFEFR | VKETSDGRYA | VQYRRKGGDD | FEAVKVIGNA |
| 181 | AGIPLTADGS | IDMFAIMPHL | SNFRDSARSS | VTSGDSVTDY | LARTRRAASE | ATGGVLSIIN |
| 241 | FEKLVHLDRE | RIDLLWKIAR | AGARSAVGTE | ARRQFRYDGD | MNIGVITDFE | LEVRNALNRR |
| 301 | AHAVGAQDVV | QHGTEQNNPF | PEADEKIFVV | SATGESQMLT | RGQLKEYIGQ | QRGEGYVFYE |
| 361 | NRAYGVAGKS | LFDDGLGAAP | GVPSGRSKFS | PDVLETVPAS | PGLRRPSLGA | VERQDSGYDS |
| 421 | LDGVGSRSFS | LGEVSDMAAV | EAAELEMTRQ | VLHAGARQDD | AEPGVSGASA | HWGQRALQGA |
| 481 | QAVAAAQRLV | HAIALMTQFG | RAGSTNTPQE | AASLSAAVFG | LGEASSAVAE | TVSGFFRGSS |
| 541 | RWAGGFGVAG | GAMALGGGIA | AAVGAGMSLT | DDAPAGQKAA | AGAQIALQLT | GGTVELASSI |
| 601 | ALALAAARGV | TSGLQVAGAS | AGAAAGALAA | ALSPMEIYGL | VQQSHYADQL | DKLAQESSAY |
| 661 | GYEGDALLAQ | LYRDKTAAEG | AVAGVSAVLS | TVGAAVSIAA | AASVVGAPVA | VVTSLLTGAL |
| 721 | NGILRGVQQP | IIEKLANDYA | RKIDELGGPQ | AYFEKNLQAR | HEQLANSDGL | RKMLADLQAG |
| 781 | WNASSVIGVQ | TTEISKSALE | LAAITGNADN | LKSVDVFVDR | FVQGERVAGQ | PVVLDVAAGG |
| 841 | IDIASRKGER | PALTFITPLA | APGEEQRRRT | KTGRSEFTTF | VEIVGKQDRW | RIRDGAADTT |
| 901 | IDLAKVVSQL | VDANGVLKHS | IKLDVIGGDG | DDVVLANASR | IHYDGGAGTN | TVSYAALGRQ |
| 961 | DSITVSADGE | RFNVRKQLNN | ANVYREGVAT | QTTAYGKRTE | NVQYRHVELA | RVGQVVEVDT |
| 1021 | LEHVQHIIGG | AGNDSITGNA | HDNFLAGGSG | DDRLDGGAGN | DTLVGGEGQN | TVIGGAGDDV |
| 1081 | FLQDLGVWSN | QLDGGAGVDT | VKYNVHQPSE | ERLERMGDTG | IHADLQKGTV | EKWPALNLFS |
| 1141 | VDHVKNIENL | HGSRLNDRIA | GDDQDNELWG | HDGNDTIRGR | GGDDILRGGL | GLDTLYGEDG |
| 1201 | NDIFLQDDET | VSDDIDGGAG | LDTVDYSAMI | HPGRIVAPHE | YGFGIEADLS | REWVRKASAL |
| 1261 | GVDYYDNVRN | VENVIGTSMK | DVLIGDAQAN | TLMGQGGDDT | VRGGDGDDLL | FGGDGNDMLY |
| 1321 | GDAGNDTLYG | GLGDDTLEGG | AGNDWFGQTQ | AREHDVLRGG | DGVDTVDYSQ | TGAHAGIAAG |
| 1381 | RIGLGILADL | GAGRVDKLGE | AGSSAYDTVS | GIENVVGTEL | ADRITGDAQA | NVLRGAGGAD |
| 1441 | VLAGGEGDDV | LLGGDGDDQL | SGDAGRDRLY | GEAGDDWFFQ | DAANAGNLLD | GGDGRDTVDF |
| 1501 | SGPGRGLDAG | AKGVFLSLGK | GFASLMDEPE | TSNVLRNIEN | AVGSARDDVL | IGDAGANVLN |
| 1561 | GLAGNDVLSG | GAGDDVLLGD | EGSDLLSGDA | GNDDLFGGQG | DDTYLFGVGY | GHDTIYESGG |
| 1621 | GHDTIRINAG | ADQLWFARQG | NDLEIRILGT | DDALTVHDWY | RDADHRVEII | HAANQAVDQA |
| 1681 | GIEKLVEAMA | QYPDPGAAAA | APPAARVPDT | LMQSLAVNWR | | |

Figure 9

```
CGGAAGAGCGCCCAATACGCAAACCGCCTCTCCCCGCGCGTTGGCCGATTCATTAATGCA
GCTGGCACGACAGGTTTCCCGACTGGAAAGCGGGCAGTGAGCGCAACGCAATTAATGTGA
GTTAGCTCACTCATTAGGCACCCCAGGCTTTACACTTTATGCTTCCGGCTCGTATGTTGT
GTGGAATTGTGAGCGGATAACAATTTCACACAGGAAACAGCTATGACCATGATTACGAAT
TTAATACGACTCACTATAGGGAAAGCTCTAGAAATAATTTTGTTTAACTTTAAGAAGGAG
ATATACATATGCTTCCGTCCGCCCAAGCGCCCTCCCTCCTCAATCCCACCGACGACTTCG
CGGCACTGGGCAATATTGCCTGGCTGTGGATGAACTCTCCCATGCACCGCGACTGGCCGG
TGCATCTGCTCGCACGCAACACGCTCGCGCCGATTCAACTGGGCCAATACATTCTGCTGC
GATGCAATGACGTGCCGGTTGCATACTGCAGCTGGGCCCTAATGGACGCCGACACCGAAC
TCTCCTATGTCATGGCGCCCTCGTCGCTGGGCGGGAATGCCTGGAACTGCGGCGACCGAC
TGTGGATCATCGACTGGATCGCGCCATTCTCGCGCGACGACAATCGTGCGCTGCGCCGCG
CGCTGGCCGAACGGCACCCCGACAGCGTGGGCCGTTCGCTGCGCGTTCGGCGCGGCGGCG
ACACCGCGCGCGTCAAGGAGTACCGAGGCCGCGCGCTGGACGCGGCCGCCACTCGCGCGC
AGCTGGACCGCTACCATGCCGAACTGATCGCAGGACTGCGCGCGAGCAACGGCGGATACG
CGCCGCGAGGCCGGGGCACCGCCTAAGGATCCTCTAGAGCTTGCATGCCCTGGCACGACA
GGTTTCCCGACTGGAAAGCGGGCAGTGAGCGCAACGCAATTAATGTGAGTTAGCTCACTC
ATTAGGCACCCCAGGCTTTACACTTTATGCTTCCGGCTCGTATGTTGTGTGGAATTGTGA
GCGGATAACAATTTCACACAGGAAACAGCTATGACCATGCAGCAATCGCATCAGGCTGGT
TACGCAAACGCCGCCGACCGGGAGTCTGGCATCCCCGCAGCCGTACTCGATGGCATCAAG
GCCGTGGCGAAGGAAAAAAACGCCACATTGATGTTCCGCCTGGTCAACCCCCATTCCACC
AGCCTGATTGCCGAAGGGGTGGCCACCAAAGGATTGGGCGTGCACGCCAAGTCGTCCGAT
TGGGGGTTGCAGGCGGGCTACATTCCCGTCAACCCGAATCTTTCCAAACTGTTCGGCCGT
GCGCCCGAGGTGATCGCGCGGGCCGACAACGACGTCAACAGCAGCCTGGCGCATGGCCAT
ACCGCGGTCGACCTGACGCTGTCGAAAGAGCGGCTTGACTATCTGCGGCAAGCGGGCCTG
GTCACCGGCATGGCCGATGGCGTGGTCGCGAGCAACCACGCAGGCTACGAGCAGTTCGAG
TTTCGCGTGAAGGAAACCTCGGACGGGCGCTATGCCGTGCAGTATCGCCGCAAGGGCGGC
GACGATTTCGAGGCGGTCAAGGTGATCGGCAATGCCGCCGGTATTCCACTGACGGCGGAT
GGATCCATCGACATGTTCGCCATTATGCCGCATCTGTCCAACTTCCGCGACTCGGCGCGC
AGTTCGGTGACCAGCGGCGATTCGGTGACCGATTACCTGGCGCGCACGCGGCGGGCCGCC
AGCGAGGCCACGGGCGGTGTACACCTGGATCGCGAACGCATCGACTTGTTGTGGAAAATC
GCTCGCGCCGGCGCCCGTTCCGCAGTGGGCACCGAGGCGCGTCGCCAGTTCCGCTACGAC
GGCGACATGAATATCGGCGTGATCACCGATTTCGAGCTGGAAGTGCGCAATGCGCTGAAC
AGGCGGGCGCACGCCGTCGGCGCGCAGGACGTGGTCCAGCATGGCACTGAGCAGAACAAT
CCTTTCCCGGAGGCAGATGAGAAGATTTTCGTCGTATCGGCCACCGGTGAAAGCCAGATG
CTCACGCGCGGGCAACTGAAGGAATACATTGGCCAGCAGCGCGGCGAGGGCTATGTCTTC
TACGAGAACCGTGCATACGGCGTGGCGGGGAAAAGCCTGTTCGACGATGGGCTGGGAGCC
GCGCCCGGCGTGCCGAGCGGACGTTCGAAGTTCTCGCCGGATGTACTGGAAACGGTGCCG
GCGTCACCCGGATTGCGGCGGCCGTCGCTGGGCGCAGTGGAACGCCAGGATTCCGGCTAT
GACAGCCTTGATGGGGTGGGATCGCGATCGTTCTCGTTGGGCGAGGTGTCCGACATGGCC
GCCGTGGAAGCGGCGGAACTGGAAATGACCCGGCAAGTCTTGCACGCCGGGGCGCGGCAG
GACGATGCCGAGCCGGGCGTGAGCGGTGCGTCGGCGCACTGGGGGCAGCGGGCGCTGCAG
GGCGCCCAGGCGGTGGCGGCGGCGCAGCGGCTGGTTCATGCCATTGCCCTGATGACGCAA
TTCGGCCGGGCCGGTTCCACCAACACGCCGCAGGAAGCGGCCTCGTTGTCGGCGGCCGTG
TTCGGCTTGGGCGAGGCCAGCAGCGCCGTGGCCGAAACCGTGAGCGGTTTTTTCCGCGGG
TCTTCGCGCTGGGCCGGCGGTTTCGGCGTGGCTGGCGGCGCGATGGCGCTGGGAGGCGGC
ATCGCCGCGGCCGTTGGCGCCGGGATGTCGTTGACCGATGACGCGCCGGCCGGACAGAAG
GCCGCCGCCGGAGCTCCGATCGCGCTGCAGTTAACGGGTGGAACGGTCGAGCTGGCTTCT
TCCATCGCGTTGGCGCTGGCCGCGGCGCGCGGCGTGACCAGCGGCTTGCAGGTGGCCGGG
GCGTCGGCCGGGCGGCTGCCGGCGCATTGGCCGCGGCGCTCAGTCCCATGGAGATCTAC
GGCCTGGTGCAGCAATCGCACTATGCGGATCAGCTGGACAAGCTGGCGCAGGAATCGAGC
GCATACGGTTACGAGGGCGACGCCTTGCTGGCCCAGCTGTATCGCGACAAGACGGCCGCC
GAGGGCGCCGTCGCCGGCGTCTCCGCCGTCCTGAGCACGGTGGGGGCGGCGGTGTCGATC
GCCGCGGCGGCCAGCGTGGTAGGGGCCCCGGTGGCGGTGGTCACTTCCTTGCTGACCGGG
```

Figure 11A

```
GCTCTCAACGGCATCCTGCGCGGCGTGCAGCAGCCCATCATCGAAAAGCTGGCCAACGAT
TACGCTCGCAAGATCGACGAGCTGGGCGGCCCGCAAGCGTACTTCGAGAAAAACCTGCAG
GCGCGTCACGAACAACTGGCCAATTCGGACGGCCTACGGAAAATGCTGGCCGACCTGCAG
GCCGGTTGGAACGCCAGCAGCGTGATCGGGGTGCAGACGACAGAGATCTCCAAGTCGGCG
CTCGAACTGGCCGCCATTACCGGCAACGCGGACAACCTGAAATCCGTCGACGTGTTCGTG
GACCGCTTCGTCCAGGGCGAGCGGGTGGCCGGCCAGCCGGTGGTCCTCGACGTCGCCGCC
GGCGGCATCGATATCGCCAGCCGCAAGGGCGAGCGGCCGGCGCTGACGTTCATCACGCCG
CTGGCCGCGCCAGGAGAAGAGCAGCGCCGGCGCACGAAAACGGGCAGATCTGAATTCACC
ACATTCGTCGAGATCGTGGGCAAGCAGGACCGCTGGCGCATCCGGGACGGCGCGGCCGAC
ACCACCATCGATCTGGCCAAGGTGGTGTCGCAACTGGTCGACGCCAATGGCGTGCTCAAG
CACAGCATCAAACTGGATGTGATCGGCGGAGATGGCGATGACGTCGTGCTTGCCAATGCT
TCGCGCATCCATTATGACGGCGGCGCGGGCACCAACACGGTCAGCTATGCCGCCCTGGGT
CGACAGGATTCCATTACCGTGTCCGCCGACGGGGAACGTTTCAACGTGCGCAAGCAGTTG
AACAACGCCAACGTGTATCGCGAAGGCGTGGCTACCCAGACAACCGCCTACGGCAAGCGC
ACGGAGAATGTCCAATACCGCCATGTCGAGCTGGCCCGTGTCGGGCAAGTGGTGGAGGTC
GACACGCTCGAGCATGTGCAGCACATCATCGGCGGGGCCGGCAACGATTCGATCACCGGC
AATGCGCACGACAACTTCCTAGCCGGCGGGTCGGGCGACGACAGGCTGGATGGCGGCGCC
GGCAACGACACCCTGGTTGGCGGCGAGGGCCAAAACACGGTCATCGGCGGCGCCGGCGAC
GACGTATTCCTGCAGGACCTGGGGGTATGGAGCAACCAGCTCGATGGCGGCGCGGGCGTC
GATACCGTGAAGTACAACGTGCACCAGCCTTCCGAGGAGCGCCTCGAACGCATGGGCGAC
ACGGGCATCCATGCCGATCTTCAAAAGGGCACGGTCGAGAAGTGGCCGGCCCTGAACCTG
TTCAGCGTCGACCATGTCAAGAATATCGAGAATCTGCACGGCTCCCGCCTAAACGACCGC
ATCGCCGGCGACGACCAGGACAACGAGCTCTGGGGCCACGATGGCAACGACACGATACGC
GGCCGGGGCGGCGACGACATCCTGCGCGGCGGCCTGGGCCTGGACACGCTGTATGGCGAG
GACGGCAACGACATCTTCCTGCAGGACGACGAGACCGTCAGCGATGACATCGACGGCGGC
GCGGGGCTGGACACCGTCGACTACTCCGCCATGATCCATCCAGGCAGGATCGTTGCGCCG
CATGAATACGGCTTCGGGATCGAGGCGGACCTGTCCAGGGAATGGGTGCGCAAGGCGTCC
GCGCTGGGCGTGGACTATTACGATAATGTCCGCAATGTCGAAAACGTCATCGGTACGAGC
ATGAAGGATGTGCTCATCGGCGACGCGCAAGCCAATACCCTGATGGGCCAGGGCGGCGAC
GATACCGTGCGCGGCGGCGACGGCGATGATCTGCTGTTCGGCGGCGACGGCAACGACATG
CTGTATGGCGACGCCGGCAACGACACCCTCTACGGGGGGCTGGGCGACGATACCCTTGAA
GGCGGCGCGGGCAACGATTGGTTCGGCCAGACGCAGGCGCGCGAGCATGACGTGCTGCGC
GGCGGAGATGGGGTGGATACCGTCGATTACAGCCAGACCGGCGCGCATGCCGGCATTGCC
GCGGGTCGCATCGGGCTGGGCATCCTGGCTGACCTGGGCGCCGGCCGCGTCGACAAGCTG
GGCGAGGCCGGCAGCAGCGCCTACGATACGGTTTCCGGTATCGAGAACGTGGTGGGCACG
GAACTGGCCGACCGCATCACGGGCGATGCGCAGGCCAACGTGCTGCGCGGCGCGGGTGGC
GCCGACGTGCTTGCGGGCGGCGAGGGCGACGATGTGCTGCTGGGCGGCGACGGCGACGAC
CAGCTGTCGGGCGACGCCGGACGCGATCGCTTGTACGGCGAAGCCGGTGACGACTGGTTC
TTCCAGGATGCCGCCAATGCCGGCAATCTGCTCGACGGCGGCGACGGCCGCGATACCGTG
GATTTCAGCGGCCCGGGCCGGGGCCTCGACGCCGGCGCAAAGGGCGTATTCCTGAGCTTG
GGCAAGGGGTTCGCCAGCCTGATGGACGAACCCGAAACCAGCAACGTGTTGCGCAATATC
GAGAACGCCGTGGGCAGCGCGCGTGATGACGTGCTGATCGGCGACGCAGGCGCCAACGTC
CTCAATGGCCTGGCGGGCAACGACGTGCTGTCCGGCGGCGCTGGCGACGATGTGCTGCTG
GGCGACGAGGGCTCGGACCTGCTCAGCGGCGATGCGGGCAACGACGATCTGTTCGGCGGG
CAGGGCGATGATACTTATCTGTTCGGGGTCGGGTACGGGCACGACACGATCTACGAATCG
GGCGGCGGCCATGACACCATCCGCATCAACGCGGGGGCGGACCAGCTGTGGTTCGCGCGC
CAGGGCAACGACCTGGAGATCCGCATTCTCGGCACCGACGATGCACTTACCGTGCACGAC
TGGTATCGCGACGCCGATCACCGGGTGGAAATCATCCATGCCGCCAACCAGGCGGTAGAC
CAGGCAGGCATCGAAAAGCTGGTCGAGGCAATGGCGCAGTATCCGGACCCCGGCGCGGCG
GCGGCTGCCCCGCCGGCGGCGCGCGTGCCGGACACGCTGATGCAGTCCCTGGCTGTCAAC
TGGCGCTGAAGCGCCGTGAATCACGGCCCGCCTGCCTCGCGCGGCGGCGCCGTCTCTTTG
CGTTCTTCTCCGAGGTATTTCCCATCATGAATTCACTGGCCGTCGTTTTACAACGTCGTG
ACTGGGAAAACCCTGGCGTTACCCAACTTAATCGCCTTGCAGCACATCCCCCTTTCGCCA
```

Figure 11B

```
GCTGGCGTAATAGCGAAGAGGCCCGCACCGATCGCCCTTCCCAACAGTTGCGCAGCCTGA
ATGGCGAATGGGAAATTGTAAACGTTAATATTTTGTTAATATTTTGTTAAAATTCGCGTT
AAATTTTTGTTAAATCAGCTCATTTTTTAACCAATAGGCCGAAATCGGCAAAATCCCTTA
TAAATCAAAAGAATAGACCGAGATAGGGTTGAGTGTTGTTCCAGTTTGGAACAAGAGTCC
ACTATTAAAGAACGTGGACTCCAACGTCAAAGGGCGAAAAACCGTCTATCAGGGCGATGG
CCCACTACGTGAACCATCACCCTAATCAAGTTTTTTGGGGTCGAGGTGCCGTAAAGCACT
AAATCGGAACCCTAAAGGGATGCCCCGATTTAGAGCTTGACGGGGAAAGCCGGCGAACGT
GGCGAGAAAGGAAGGGAAGAAAGCGAAAGGAGCGGGCGCTAGGGCGCTGGCAAGTGTAGC
GGTCACGCTGCGCGTAACCACCACACCCGCCGCGCTTAATGCGCCGCTACAGGGCGCGTC
AGGTGGCACTTTTCGGGGAAATGTGCGCGGAACCCCTATTTGTTTATTTTTCTAAATACA
TTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATT
TTGCCTTCCTGTTTTTGCTCACCCAGAAACGCTGGTGAAAGTAAAAGATGCTGAAGATCA
GTTGGGTGCACGAGTGGGTTACATCGAACTGGATCTCAACAGCGGTAAGATCCTTGAGAG
TTTTCGCCCCGAAGAACGTTTTCCAATGATGAGCACTTTTAAAGTTCTGCTATGTGGCGC
GGTATTATCCCGTATTGACGCCGGGCAAGAGCAACTCGGTCGCCGCATACACTATTCTCA
GAATGACTTGGTTGAGTACTCACCAGTCACAGAAAAGCATCTTACGGATGGCATGACAGT
AAGAGAATTATGCAGTGCTGCCATAACCATGAGTGATAACACTGCGGCCAACTTACTTCT
GACAACGATCGGAGGACCGAAGGAGCTAACCGCTTTTTTGCACAACATGGGGGATCATGT
AACTCGCCTTGATCGTTGGGAACCGGAGCTGAATGAAGCCATACCAAACGACGAGCGTGA
CACCACGATGCCTGTAGCAATGGCAACAACGTTGCGCAAACTATTAACTGGCGAACTACT
TACTCTAGCTTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTGA
GATAGGTGCCTCACTGATTAAGCATTGGTAACTGTCAGACCAAGTTTACTCATATATACT
TTAGATTGATTTAAAACTTCATTTTTAATTTAAAAGGATCTAGGTGAAGATCCTTTTTGA
TAATCTCATGACCAAAATCCCTTAACGTGAGTTTTCGTTCCACTGAGCGTCAGACCCCGT
AGAAAAGATCAAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGCTACCAACTCT
TTTTCCGAAGGTAACTGGCTTCAGCAGAGCGCAGATACCAAATACTGTCCTTCTAGTGTA
GCCGTAGTTAGGCCACCACTTCAAGAACTCTGTAGCACCGCCTACATACCTCGCTCTGCT
AATCCTGTTACCAGTGGCTGCTGCCAGTGGCGATAAGTCGTGTCTTACCGGGTTGGACTC
AAGACGATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCTATGAGA
AAGCGCCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTCCTGT
CGGGTTTCGCCACCTCTGACTTGAGCGTCGATTTTGTGATGCTCGTCAGGGGGCGGAG
CCTATGGAAAAACGCCAGCAACGCGGCCTTTTTACGGTTCCTGGCCTTTTGCTGGCCTTT
TGCTCACATGTTCTTTCCTGCGTTATCCCCTGATTCTGTGGATAACCGTATTACCGCCTT
TGAGTGAGCTGATACCGCTCGCCGCAGCCGAACGACCGAGCGCAGCGAGTCAGTGAGCGA
GGAAG
```

Figure 11C

```
CGGAAGAGCGCCCAATACGCAAACCGCCTCTCCCCGCGCGTTGGCCGATTCATTAATGCA
GCTGGCACGACAGGTTTCCCGACTGGAAAGCGGGCAGTGAGCGCAACGCAATTAATGTGA
GTTAGCTCACTCATTAGGCACCCCAGGCTTTACACTTTATGCTTCCGGCTCGTATGTTGT
GTGGAATTGTGAGCGGATAACAATTTCACACAGGAAACAGCTATGACCATGATTACGAAT
TTAATACGACTCACTATAGGGAAAGCTCTAGAAATAATTTTGTTTAACTTTAAGAAGGAG
ATATACATATGCTTCCGTCCGCCCAAGCGCCCTCCCTCCTCAATCCCACCGACGACTTCG
CGGCACTGGGCAATATTGCCTGGCTGTGGATGAACTCTCCCATGCACCGCGACTGGCCGG
TGCATCTGCTCGCACGCAACACGCTCGCGCCGATTCAACTGGGCCAATACATTCTGCTGC
GATGCAATGACGTGCCGGTTGCATACTGCAGCTGGGCCCTAATGGACGCCGACACCGAAC
TCTCCTATGTCATGGCGCCCTCGTCGCTGGGCGGGAATGCCTGGAACTGCGGCGACCGAC
TGTGGATCATCGACTGGATCGCGCCATTCTCGCGCGACGACAATCGTGCGCTGCGCCGCG
CGCTGGCCGAACGGCACCCCGACAGCGTGGGCCGTTCGCTGCGCGTTCGGCGCGGCGGCG
ACACCGCGCGCGTCAAGGAGTACCGAGGCCGCGCGCTGGACGCGGCCGCCACTCGCGCGC
AGCTGGACCGCTACCATGCCGAACTGATCGCAGGACTGCGCGCGAGCAACGGCGGATACG
CGCCGCGAGGCCGGGGCACCGCCTAAGGATCCTCTAGAGCTTGCATGCCCTGGCACGACA
GGTTTCCCGACTGGAAAGCGGGCAGTGAGCGCAACGCAATTAATGTGAGTTAGCTCACTC
ATTAGGCACCCCAGGCTTTACACTTTATGCTTCCGGCTCGTATGTTGTGTGGAATTGTGA
GCGGATAACAATTTCACACAGGAAACAGCTATGACCATGCAGCAATCGCATCAGGCTGGT
TACGCAAACGCCGCCGACCGGGAGTCTGGCATCCCCGCAGCCGTACTCGATGGCATCAAG
GCCGTGGCGAAGGAAAAAAACGCCACATTGATGTTCCGCCTGGTCAACCCCCATTCCACC
AGCCTGATTGCCGAAGGGGTGGCCACCAAAGGATTGGGCGTGCACGCCAAGTCGTCCGAT
TGGGGGTTGCAGGCGGGCTACATTCCCGTCAACCCGAATCTTTCCAAACTGTTCGGCCGT
GCGCCCGAGGTGATCGCGCGGGCCGACAACGACGTCAACAGCAGCCTGGCGCATGGCCAT
ACCGCGGTCGACCTGACGCTGTCGAAAGAGCGGCTTGACTATCTGCGGCAAGCGGGCCTG
GTCACCGGCATGGCCGATGGCGTGGTCGCGAGCAACCACGCAGGCTACGAGCAGTTCGAG
TTTCGCGTGAAGGAAACCTCGGACGGGCGCTATGCCGTGCAGTATCGCCGCAAGGGCGGC
GACGATTTCGAGGCGGTCAAGGTGATCGGCAATGCCGCCGGTATTCCACTGACGGCGGAT
GGATCCATCGACATGTTCGCCATTATGCCGCATCTGTCCAACTTCCGCGACTCGGCGCGC
AGTTCGGTGACCAGCGGCGATTCGGTGACCGATTACCTGGCGCGCACGCGGCGGGCCGCC
AGCGAGGCCACGGGCGGTGTACTCTCAATAATTAATTTCGAAAAGCTTGTACACCTGGAT
CGCGAACGCATCGACTTGTTGTGGAAAATCGCTCGCGCCGGCGCCCGTTCCGCAGTGGGC
ACCGAGGCGCGTCGCCAGTTCCGCTACGACGGCGACATGAATATCGGCGTGATCACCGAT
TTCGAGCTGGAAGTGCGCAATGCGCTGAACAGGCGGGCGCACGCCGTCGGCGCGCAGGAC
GTGGTCCAGCATGGCACTGAGCAGAACAATCCTTTCCCGGAGGCAGATGAGAAGATTTTC
GTCGTATCGGCCACCGGTGAAAGCCAGATGCTCACGCGCGGGCAACTGAAGGAATACATT
GGCCAGCAGCGCGGCGAGGGCTATGTCTTCTACGAGAACCGTGCATACGGCGTGGCGGGG
AAAAGCCTGTTCGACGATGGGCTGGAGCCGCGCCCGGCGTGCCGAGCGGACGTTCGAAG
TTCTCGCCGGATGTACTGGAAACGGTGCCGGCGTCACCCGGATTGCGGCGGCCGTCGCTG
GGCGCAGTGGAACGCCAGGATTCCGGCTATGACAGCCTTGATGGGGTGGGATCGCGATCG
TTCTCGTTGGGCGAGGTGTCCGACATGGCCGCCGTGGAAGCGGCGGAACTGGAAATGACC
CGGCAAGTCTTGCACGCCGGGGCGCGGCAGGACGATGCCGAGCCGGGCGTGAGCGGTGCG
TCGGCGCACTGGGGGCAGCGGGCGCTGCAGGGCGCCCAGGCGGTGGCGGCGGCGCAGCGG
CTGGTTCATGCCATTGCCCTGATGACGCAATTCGGCCGGGCCGGTTCCACCAACACGCCG
CAGGAAGCGGCCTCGTTGTCGGCGGCCGTGTTCGGCTTGGGCGAGGCCAGCAGCGCCGTG
GCCGAAACCGTGAGCGGTTTTTTCCGCGGGTCTTCGCGCTGGGCCGGCGGTTTCGGCGTG
GCTGGCGGCGCGATGGCGCTGGGAGGCGGCATCGCCGCGGCCGTTGGCGCCGGGATGTCG
TTGACCGATGACGCGCCGGCCGGACAGAAGGCCGCCGCCGGAGCTCCGATCGCGCTGCAG
TTAACGGGTGGAACGGTCGAGCTGGCTTCTTCCATCGCGTTGGCGCTGGCCGCGGCGCGC
GGCGTGACCAGCGGCTTGCAGGTGGCCGGGGCGTCGGCCGGGCGGCTGCCGGCGCATTG
GCCGCGGCGCTCAGTCCCATGGAGATCTACGGCCTGGTGCAGCAATCGCACTATGCGGAT
CAGCTGGACAAGCTGGCGCAGGAATCGAGCGCATACGGTTACGAGGGCGACGCCTTGCTG
GCCCAGCTGTATCGCGACAAGACGGCCGCCGAGGGCGCCGTCGCCGGCGTCTCCGCCGTC
```

Figure 13A

```
CTGAGCACGGTGGGGGCGGCGGTGTCGATCGCCGCGGCGGCCAGCGTGGTAGGGGCCCCG
GTGGCGGTGGTCACTTCCTTGCTGACCGGGGCTCTCAACGGCATCCTGCGCGGCGTGCAG
CAGCCCATCATCGAAAAGCTGGCCAACGATTACGCTCGCAAGATCGACGAGCTGGGCGGG
CCGCAAGCGTACTTCGAGAAAACCTGCAGGCGCGTCACGAACAACTGGCCAATTCGGAC
GGCCTACGGAAAATGCTGGCCGACCTGCAGGCCGGTTGGAACGCCAGCAGCGTGATCGGG
GTGCAGACGACAGAGATCTCCAAGTCGGCGCTCGAACTGGCCGCCATTACCGGCAACGCG
GACAACCTGAAATCCGTCGACGTGTTCGTGGACCGCTTCGTCCAGGGCGAGCGGGTGGCC
GGCCAGCCGGTGGTCCTCGACGTCGCCGCCGGCGGCATCGATATCGCCAGCCGCAAGGGC
GAGCGGCCGGCGCTGACGTTCATCACGCCGCTGGCCGCGCCAGGAGAAGAGCAGCGCCGG
CGCACGAAAACGGGCAGATCTGAATTCACCACATTCGTCGAGATCGTGGGCAAGCAGGAC
CGCTGGCGCATCCGGGACGGCGCGGCCGACACCACCATCGATCTGGCCAAGGTGGTGTCG
CAACTGGTCGACGCCAATGGCGTGCTCAAGCACAGCATCAAACTGGATGTGATCGGCGGA
GATGGCGATGACGTCGTGCTTGCCAATGCTTCGCGCATCCATTATGACGGCGGCGCGGGC
ACCAACACGGTCAGCTATGCCGCCCTGGGTCGACAGGATTCCATTACCGTGTCCGCCGAC
GGGGAACGTTTCAACGTGCGCAAGCAGTTGAACAACGCCAACGTGTATCGCGAAGGCGTG
GCTACCCAGACAACCGCCTACGGCAAGCGCACGGAGAATGTCCAATACCGCCATGTCGAG
CTGGCCCGTGTCGGGCAAGTGGTGGAGGTCGACACGCTCGAGCATGTGCAGCACATCATC
GGCGGGGCCGGCAACGATTCGATCACCGGCAATGCGCACGACAACTTCCTAGCCGGCGGG
TCGGGCGACGACAGGCTGGATGGCGGCGCCGGCAACGACACCCTGGTTGGCGGCGAGGGC
CAAAACACGGTCATCGGCGGCGCCGGCGACGACGTATTCCTGCAGGACCTGGGGGTATGG
AGCAACCAGCTCGATGGCGGCGCGGGCGTCGATACCGTGAAGTACAACGTGCACCAGCCT
TCCGAGGAGCGCCTCGAACGCATGGGCGACACGGGCATCCATGCCGATCTTCAAAAGGGC
ACGGTCGAGAAGTGGCCGGCCCTGAACCTGTTCAGCGTCGACCATGTCAAGAATATCGAG
AATCTGCACGGCTCCCGCCTAAACGACCGCATCGCCGGCGACGACCAGGACAACGAGCTC
TGGGGCCACGATGGCAACGACACGATACGCGGCCGGGCGGCGACGACATCCTGCGCGGC
GGCCTGGGCCTGGACACGCTGTATGGCGAGGACGGCAACGACATCTTCCTGCAGGACGAC
GAGACCGTCAGCGATGACATCGACGGCGGCGCGGGGCTGGACACCGTCGACTACTCCGCC
ATGATCCATCCAGGCAGGATCGTTGCGCCGCATGAATACGGCTTCGGGATCGAGGCGGAC
CTGTCCAGGGAATGGGTGCGCAAGGCGTCCGCGCTGGGCGTGGACTATTACGATAATGTC
CGCAATGTCGAAAACGTCATCGGTACGAGCATGAAGGATGTGCTCATCGGCGACGCGCAA
GCCAATACCCTGATGGGCCAGGGCGGCGACGATACCGTGCGCGGCGGCGACGGCGATGAT
CTGCTGTTCGGCGGCGACGGCAACGACATGCTGTATGGCGACGCCGGCAACGACACCCTC
TACGGGGGGCTGGGCGACGATACCCTTGAAGGCGGCGCGGGCAACGATTGGTTCGGCCAG
ACGCAGGCGCGCGAGCATGACGTGCTGCGCGGCGGAGATGGGGTGGATACCGTCGATTAC
AGCCAGACCGGCGCGCATGCCGGCATTGCCGCGGGTCGCATCGGGCTGGGCATCCTGGCT
GACCTGGGCGCCGGCCGCGTCGACAAGCTGGGCGAGGCCGGCAGCAGCGCCTACGATACG
GTTTCCGGTATCGAGAACGTGGTGGGCACGGAACTGGCCGACCGCATCACGGGCGATGCG
CAGGCCAACGTGCTGCGCGGCGCGGGTGGCGCCGACGTGCTTGCGGGCGGCGAGGGCGAC
GATGTGCTGCTGGGCGGCGACGGCGACGACCAGCTGTCGGGCGACGCCGGACGCGATCGC
TTGTACGGCGAAGCCGGTGACGACTGGTTCTTCCAGGATGCCGCCAATGCCGGCAATCTG
CTCGACGGCGGCGACGGCCGCGATACCGTGGATTTCAGCGGCCCGGGCCGGGGCCTCGAC
GCCGGCGCAAAGGGCGTATTCCTGAGCTTGGGCAAGGGGTTCGCCAGCCTGATGGACGAA
CCCGAAACCAGCAACGTGTTGCGCAATATCGAGAACGCCGTGGGCAGCGCGCGTGATGAC
GTGCTGATCGGCGACGCAGGCGCCAACGTCCTCAATGGCCTGGCGGGCAACGACGTGCTG
TCCGGCGGCGCTGGCGACGATGTGCTGCTGGGCGACGAGGGCTCGGACCTGCTCAGCGGC
GATGCGGGCAACGACGATCTGTTCGGCGGGCAGGGCGATGATACTTATCTGTTCGGGGTC
GGGTACGGGCACGACACGATCTACGAATCGGGCGGCGGCCATGACACCATCCGCATCAAC
GCGGGGGCGGACCAGCTGTGGTTCGCGCGCCAGGGCAACGACCTGGAGATCCGCATTCTC
GGCACCGACGATGCACTTACCGTGCACGACTGGTATCGCGACGCCGATCACCGGGTGGAA
ATCATCCATGCCGCCAACCAGGCGGTAGACCAGGCAGGCATCGAAAAGCTGGTCGAGGCA
ATGGCGCAGTATCCGGACCCCGGCGCGGCGGCGGCTGCCCCGCCGGCGGCGCGCGTGCCG
GACACGCTGATGCAGTCCCTGGCTGTCAACTGGCGCTGAAGCGCCGTGAATCACGGCCCG
CCTGCCTCGCGCGGCGGCGCCGTCTCTTTGCGTTCTTCTCCGAGGTATTTCCCATCATGA
```

Figure 13B

```
ATTCACTGGCCGTCGTTTTACAACGTCGTGACTGGGAAAACCCTGGCGTTACCCAACTTA
ATCGCCTTGCAGCACATCCCCCTTTCGCCAGCTGGCGTAATAGCGAAGAGGCCCGCACCG
ATCGCCCTTCCCAACAGTTGCGCAGCCTGAATGGCGAATGGGAAATTGTAAACGTTAATA
TTTTGTTAATATTTTGTTAAAATTCGCGTTAAATTTTGTTAAATCAGCTCATTTTTTAA
CCAATAGGCCGAAATCGGCAAAATCCCTTATAAATCAAAAGAATAGACCGAGATAGGGTT
GAGTGTTGTTCCAGTTTGGAACAAGAGTCCACTATTAAAGAACGTGGACTCCAACGTCAA
AGGGCGAAAAACCGTCTATCAGGGCGATGGCCCACTACGTGAACCATCACCCTAATCAAG
TTTTTTGGGGTCGAGGTGCCGTAAAGCACTAAATCGGAACCCTAAAGGGATGCCCCGATT
TAGAGCTTGACGGGGAAAGCCGGCGAACGTGGCGAGAAAGGAAGGGAAGAAAGCGAAAGG
AGCGGGCGCTAGGGCGCTGGCAAGTGTAGCGGTCACGCTGCGCGTAACCACCACACCCGC
CGCGCTTAATGCGCCGCTACAGGGCGCGTCAGGTGGCACTTTTCGGGGAAATGTGCGCGG
AACCCCTATTTGTTTATTTTTCTAAATACATTCAAATATGTATCCGCTCATGAGACAATA
ACCCTGATAAATGCTTCAATAATATTGAAAAAGGAAGAGTATGAGTATTCAACATTTCCG
TGTCGCCCTTATTCCCTTTTTTGCGGCATTTTGCCTTCCTGTTTTGCTCACCCAGAAAC
GCTGGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGA
GCAACTCGGTCGCCGCATACACTATTCTCAGAATGACTTGGTTGAGTACTCACCAGTCAC
AGAAAAGCATCTTACGGATGGCATGACAGTAAGAGAATTATGCAGTGCTGCCATAACCAT
GAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCT
GAATGAAGCCATACCAAACGACGAGCGTGACACCACGATGCCTGTAGCAATGGCAACAAC
GTTGCGCAAACTATTAACTGGCGAACTACTTACTCTAGCTTCCCGGCAACAATTAATAGA
CTGGATGGAGGCGGATAAAGTTGCAGGACCACTTCTGCGCTCGGCCCTTCCGGCTGGCTG
GTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAAC
TATGGATGAACGAAATAGACAGATCGCTGAGATAGGTGCCTCACTGATTAAGCATTGGTA
ACTGTCAGACCAAGTTTACTCATATATACTTTAGATTGATTTAAAACTTCATTTTTAATT
TAAAAGGATCTAGGTGAAGATCCTTTTTGATAATCTCATGACCAAAATCCCTTAACGTGA
GTTTTCGTTCCACTGAGCGTCAGACCCCGTAGAAAAGATCAAAGGATCTTCTTGAGATCC
TTTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCAAGAACTC
TGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCG
GTCGGGCTGAACGGGGGGTTCGTGCACACAGCCCAGCTTGGAGCGAACGACCTACACCGA
ACTGAGATACCTACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCG
ATTTTTGTGATGCTCGTCAGGGGGCGGAGCCTATGGAAAAACGCCAGCAACGCGGCCTT
TTTACGGTTCCTGGCCTTTTGCTGGCCTTTTGCTCACATGTTCTTTCCTGCGTTATCCCC
TGATTCTGTGGATAACCGTATTACCGCCTTTGAGTGAGCTGATACCGCTCGCCGCAGCCG
AACGACCGAGCGCAGCGAGTCAGTGAGCGAGGAAG
```

Figure 13C

```
   1 MQQSHQAGYA NAADRESGIP AAVLDGIKAV AKEKNATLMF RLVNPHSTSL IAEGVATKGL
  61 GVHAKSSDWG LQAGYIPVNP NLSKLFGRAP EVIARADNDV NSSLAHGHTA VDLTLSKERL
 121 DYLRQAGLVT GMADGVVASN HAGYEQFEFR VKETSDGRYA VQYRRKGGDD FEAVKVIGNA
 181 AGIPLTADID MFAIMPHLSN FRDSARSSVT SGDSVTDYLA RTRRAASEAT GGLDRERIDL
 241 LWKIARAGAR SAVGTEARRQ FRYDGDMNIG VITDFELEVR NALNRRAHAV GAQDVVQHGT
 301 EQNNPFPEAD EKIFVVSATG ESQMLTRGQL KEYIGQQRGE GYVFYENRAY GVAGKSLFDD
 361 GLGAAPGVPG GRSKSSPDVL ETVPASPGLR RPSLGAVERQ DSGYDSLDGV GSRSFSLGEV
 421 SDMAAVEAAE LEMTRQVLHA GARQDDAEPG VSGASAHWGQ RALQGAQAVA AAQRLVHAIA
 481 LMTQFGRAGS TNTPQEAASL SAAVFGLGEA SSAVAETVSG FFRGSSRWAG GFGVAGGAMA
 541 LGGGIAAAVG AGMSLTDDAP AGQKAAVGAE IALQLTGGTV ELASSIALAL AAARGVTSGL
 601 QVAGASAGAA AGALAAALSP MEIYGLVQQS HYADQLDKLA QESSAYGYEG DALLAQLYRD
 661 KTAAEGAVAG VSAVLSTVGA AVSIAAAASV VGAPVAVVTS LLTGALNGIL RGVQQPIIEK
 721 LANDYARKID ELGGPQAYFE KNLQARHEQL ANSDGLRKML ADLQAGWNAS SVIGVQTTEI
 781 SKSALELAAI TGNADNLKSA DVFVDRFIQG ERVAGQPVVL DVAAGGIDIA SRKGERPALT
 841 FITPLAAPGE EQRRRTKTGK SEFTTFVEIV GKQDRWRIRD GAADTTIDLA KVVSQLVDAN
 901 GVLKHSIKLE VIGGDGDDVV LANASRIHYD GGAGTNTVSY AALGRQDSIT VSADGERFNV
 961 RKQLNNANVY REGVATQKTA YGKRTENVQY RHVELARVGQ LVEVDTLEHV QHIIGGAGND
1021 SITGNAHDNF LAGGAGDDRL DGGAGNDTLV GGEGHNTVVG GAGDDVFLQD LGVWSNQLDG
1081 GAGVDTVKYN VHQPSEERLE RMGDTGIHAD LQKGTVEKWP ALNLFSVDHV KNIENLHGSS
1141 LNDSIAGDDR DNELWGDDGN DTIHGRGGDD ILRGGLGLDT LYGEDGNDIF LQDDETVSDD
1201 IDGGAGLDTV DYSAMIHAGK IVAPHEYGFG IEADLSEGWV RKAARRGMGY YDSVRSVENV
1261 IGTSMKDVLI GDAQANTLMG QGGDDTVRGG DGDDLLFGGD GNDMLYGDAG NDTLYGGLGD
1321 DTLEGGAGND WFGQTPAREH DVLRGGAGVD TVDYSQAGAH AGVATGRIGL GILADLGAGR
1381 VDKLGEAGSS AYDTVSGIEN VVGTELADRI TGDAQANVLR GAGGADVLAG GEGDDVLLGG
1441 EGDDQLSGDA GRDRLYGEAG DDWFFQDAAN AGNLLDGGDG NDTVDFSGPG RGLDAGAKGV
1501 FLSLGKGFAS LMDEPETSNV LRHIENAVGS VRDDVLIGDA GANVLNGLAG NDVLSGGAGD
1561 DVLLGDEGSD LLSGDAGNDD LFGGQGDDTY LFGAGYGHDT IYESGGGHDT IRINAGADQL
1621 WFARQGNDLE IRILGTDDAL TVHDWYRDAD HRVEAIHAAN QAIDPAGIEK LVEAMAQYPD
1681 PGAAAAAPPA ARVPDTLMQS LAVNWR
```

Figure 14

```
   1 MQQSHQAGYA NAADRESGIP AAVLDGIKAV AKEKNATLMF RLVNPHSTSL IAEGVATKGL
  61 GVHAKSSDWG LQAGYIPVNP NLSKLFGRAP EVIARADNDV NSSLAHGHTA VDLTLSKERL
 121 DYLRQAGLVT GMADGVVASN HAGYEQFEFR VKETSDGRYA VQYRRKGGDD FEAVKVIGNA
 181 AGIPLTADID MFAIMPHLSN FRDSARSSVT SGDSVTDYLA RTRRAASEAT GGLDRERIDL
 241 LWKIARAGAR SAVGTEARRQ FRYDGDMNIG VITDFELEVR NALNRRAHAV GAQDVVQHGT
 301 EQNNPFPEAD EKIFVVSATG ESQMLTRGQL KEYIGQQRGE GYVFYENRAY GVAGKSLFDD
 361 GLGAAPGVPS GRSKFSPDVL ETVPASPGLR RPSLGAVERQ DSGYDSLDGV GSRSFSLGEV
 421 SDMAAVEAAE LEMTRQVLHA GARQDDAEPG VSGASAHWGQ RALQGAQAVA AAQRLVHAIA
 481 LMTQFGRAGS TNTPQEAASL SAAVFGLGEA SSAVAETVSG FFRGSSRWAG GFGVAGGAMA
 541 LGGGIAAAVG AGMSLTDDAP AGQKAAAGAE IALQLTGGTV ELASSIALAL AAARGVTSGL
 601 QVAGASAGAA AGALAAALSP MEIYGLVQQS HYADQLDKLA QESSAYGYEG DALLAQLYRD
 661 KTAAEGAVAG VSAVLSTVGA AVSIAAAASV VGAPVAVVTS LLTGALNGIL RGVQQPIIEK
 721 LANDYARKID ELGGPQAYFE KNLQARHEQL ANSDGLRKML ADLQAGWNAS SVIGVQTTEI
 781 SKSALELAAI TGNADNLKSV DVFVDRFVQG ERVAGQPVVL DVAAGGIDIA SRKGERPALT
 841 FITPLAAPGE EQRRRTKTGK SEFTTFVEIV GKQDRWRIRD GAADTTIDLA KVVSQLVDAN
 901 GVLKHSIKLD VIGGDGDDVV LANASRIHYD GGAGTNTVSY AALGRQDSIT VSADGERFNV
 961 RKQLNNANVY REGVATQTTA YGKRTENVQY RHVELARVGQ LVEVDTLEHV QHIIGGAGND
1021 SITGNAHDNF LAGGSGDDRL DGGAGNDTLV GGEGQNTVIG GAGDDVFLQD LGVWSNQLDG
1081 GAGVDTVKYN VHQPSEERLE RMGDTGIHAD LQKGTVEKWP ALNLFSVDHV KNIENLHGSR
1141 LNDRIAGDDQ DNELWGHDGN DTIRGRGGDD ILRGGLGLDT LYGEDGNDIF LQDDETVSDD
1201 IDGGAGLDTV DYSAMIHPGR IVAPHEYGFG IEADLSREWV RKASALGVDY YDNVRNVENV
1261 IGTSMKDVLI GDAQANTLMG QGGDDTVRGG DGDDLLFGGD GNDMLYGDAG NDTLYGGLGD
1321 DTLEGGAGND WFGQTQAREH DVLRGGDGVD TVDYSQTGAH AGIAAGRIGL GILADLGAGR
1381 VDKLGEAGSS AYDTVSGIEN VVGTELADRI TGDAQANVLR GAGGADVLAG GEGDDVLLGG
1441 DGDDQLSGDA GRDRLYGEAG DDWFFQDAAN AGNLLDGGDG RDTVDFSGPG RGLDAGAKGV
1501 FLSLGKGFAS LMDEPETSNV LRNIENAVGS ARDDVLIGDA GANVLNGLAG NDVLSGGAGD
1561 DVLLGDEGSD LLSGDAGNDD LFGGQGDDTY LFGVGYGHDT IYESGGGHDT IRINAGADQL
1621 WFARQGNDLE IRILGTDDAL TVHDWYRDAD HRVEIIHAAN QAVDQAGIEK LVEAMAQYPD
1681 PGAAAAAPPA ARVPDTLMQS LAVNWR
```

Figure 15

```
   1  MQQSHQAGYA  NAADRESGIP  AAVLDGIKAV  AKEKNATLMF  RLVNPHSTSL  IAEGVATKGL
  61  GVHAKSSDWG  LQAGYIPVNP  NLSKLFGRAP  EVIARADNDV  NSSLAHGHTA  VDLTLSKERL
 121  DYLRQAGLVT  GMADGVVASN  HAGYEQFEFR  VKETSDGRYA  VQYRRKGGDD  FEAVKVIGNA
 181  AGIPLTADID  MFAIMPHLSN  FRDSARSSVT  SGDSVTDYLA  RTRRAASEAT  GGLDRERIDL
 241  LWKIARAGAR  SAVGTEARRQ  FRYDGDMNIG  VITDFELEVR  NALNRRAHAV  GRQDVVQHGT
 301  EQNNPFPEAD  EKIFVVSATG  ESQMLTRGQL  KEYIGQQRGE  GYVFYENRAY  GVAGKSLFDD
 361  GLGAAPGVPG  RRSKSSPDVL  ETVPASPGLR  RPSLGAVERQ  DSGYDSLDGV  GSRSFSLGEV
 421  SDMAAVEAAE  LEMTRQVLHA  GARQDDAEPG  VSGASAHWGQ  RALQGAQAVA  AAQRLVHAIA
 481  LMTQFGRAGS  TNTPQEAASL  SAAVFGLGEA  SSAVAETVSG  FFRGSSRWAG  GFGVAGGAMA
 541  LGGGIGAVGA  GMSLTDDAPA  GQKAAAGAEI  ALQLTGGTVE  LASSIALALA  AARGVTSGLQ
 601  VAGASAGAAA  GALAAALSPM  EIYGLVQQSH  YADQLDKLAQ  ESSAYGYEGD  ALLAQLYRDK
 661  TAAEGAVAGV  SAVLSTVGAA  VSIAAAASVV  GAPVAVVTSL  LTGALNGILR  GVQQPIIEKL
 721  ANDYARKIDE  LGGPQAYFEK  NLQARHEQLA  NSDGLRKMLA  DLQAGWNASS  VIGVQTTEIS
 781  KSALELAAIT  GNADNLKSAD  VFVDRFIQGE  RVAGQPVVLD  VAAGGIDIAS  RKGERPALTF
 841  ITPLAAPGEE  QRRRTKTGKS  EFTTFVEIVG  KQDRWRIRDG  AADTTIDLAK  VVSQLVDANG
 901  VLKHSIKLEV  IGGDGDDVVL  ANASRIHYDG  GAGTNTVSYA  ALGRQDSITV  SADGERFNVR
 961  KQLNNANVYR  EGVATQKTAY  GKRTENVQYR  HVELARVQGL  VEVDTLEHVQ  HIIGGAGNDS
1021  ITGNAHDNFL  AGGAGDDRLD  GGAGNDTLVG  GEGHNTVVGG  AGDDVFLQDL  GVWSNQLDGG
1081  AGVDTVKYNV  HQPSEERLER  MGDTGIHADL  QKGTVEKWPA  LNLFSVDHVK  NIENLHGSSL
1141  NDSIAGDDRD  NELWGDDGND  TIHGRGGDDI  LRGGLGLDTL  YGEDGNDIFL  QDDETVSDDI
1201  DGGAGLDTVD  YSAMIHAGKI  VAPHEYGFGI  EADLSEGWVR  KAARRGMDYY  DSVRSVENVI
1261  GTSMKDVLIG  DAQANTLMGQ  GGDDTVRGGD  GDDLLFGGDG  NDMLYGDAGN  DTLYGGLGDD
1321  TLEGGAGNDW  FGQTPAREHD  VLRGGAGVDT  VDYSQAGAHA  GVATGRIGLG  ILADLGAGRV
1381  DKLGEAGSSA  YDTVSGIENV  VGTELADRIT  GDAQANVLRG  AGGADVLAGG  EGDDVLLGGD
1441  GDDQLSGDAG  RDRLYGEAGD  DWFFQDAANA  GNLLDGGDGN  DTVDFSGPGR  GLDAGAKGVF
1501  LSLGKGFASL  MDEPETSNVL  RHIENAVGSV  RDDVLIGDAG  ANVLNGLAGN  DVLSGGAGDD
1561  VLLGDEGSDL  LSGDAGNDDL  FGGQGDDTYL  FGAGYGHDTI  YESGGGHDTI  RINAGADQLW
1621  FARQGNDLEI  RILGTDDALT  VHDWYRDADH  RVEAIHAANQ  AIDPAGIEKL  VEAMAQYPDP
1681  GAAAAAPPAA  RVPDTLMQSL  AVNWR
```

Figure 16

SEQUENCE LISTING

<160> NUMBER OF SEQ ID NOS: 12

<210> SEQ ID NO 1
<211> LENGTH: 1706
<212> TYPE: PRT
<213> ORGANISM: Bordetella pertussis

<400> SEQUENCE: 1

Met Gln Gln Ser His Gln Ala Gly Tyr Ala Asn Ala Ala Asp Arg Glu
1 5 10 15

Ser Gly Ile Pro Ala Ala Val Leu Asp Gly Ile Lys Ala Val Ala Lys
20 25 30

Glu Lys Asn Ala Thr Leu Met Phe Arg Leu Val Asn Pro His Ser Thr
35 40 45

Ser Leu Ile Ala Glu Gly Val Ala Thr Lys Gly Leu Gly Val His Ala
50 55 60

Lys Ser Ser Asp Trp Gly Leu Gln Ala Gly Tyr Ile Pro Val Asn Pro
65 70 75 80

Asn Leu Ser Lys Leu Phe Gly Arg Ala Pro Glu Val Ile Ala Arg Ala
85 90 95

Asp Asn Asp Val Asn Ser Ser Leu Ala His Gly His Thr Ala Val Asp
100 105 110

Leu Thr Leu Ser Lys Glu Arg Leu Asp Tyr Leu Arg Gln Ala Gly Leu
115 120 125

Val Thr Gly Met Ala Asp Gly Val Val Ala Ser Asn His Ala Gly Tyr
130 135 140

Glu Gln Phe Glu Phe Arg Val Lys Glu Thr Ser Asp Gly Arg Tyr Ala
145 150 155 160

Val Gln Tyr Arg Arg Lys Gly Gly Asp Asp Phe Glu Ala Val Lys Val
165 170 175

Ile Gly Asn Ala Ala Gly Ile Pro Leu Thr Ala Asp Ile Asp Met Phe
180 185 190

Ala Ile Met Pro His Leu Ser Asn Phe Arg Asp Ser Ala Arg Ser Ser
195 200 205

Val Thr Ser Gly Asp Ser Val Thr Asp Tyr Leu Ala Arg Thr Arg Arg
210 215 220

Ala Ala Ser Glu Ala Thr Gly Gly Leu Asp Arg Glu Arg Ile Asp Leu
225 230 235 240

Leu Trp Lys Ile Ala Arg Ala Gly Ala Arg Ser Ala Val Gly Thr Glu
245 250 255

Ala Arg Arg Gln Phe Arg Tyr Asp Gly Asp Met Asn Ile Gly Val Ile
260 265 270

Thr Asp Phe Glu Leu Glu Val Arg Asn Ala Leu Asn Arg Arg Ala His
275 280 285

Ala Val Gly Ala Gln Asp Val Val Gln His Gly Thr Glu Gln Asn Asn
290 295 300

Pro Phe Pro Glu Ala Asp Glu Lys Ile Phe Val Val Ser Ala Thr Gly
305 310 315 320

Glu Ser Gln Met Leu Thr Arg Gly Gln Leu Lys Glu Tyr Ile Gly Gln
325 330 335

Gln Arg Gly Glu Gly Tyr Val Phe Tyr Glu Asn Arg Ala Tyr Gly Val
340 345 350

Ala Gly Lys Ser Leu Phe Asp Asp Gly Leu Gly Ala Ala Pro Gly Val
355 360 365

-continued

```
Pro Ser Gly Arg Ser Lys Phe Ser Pro Asp Val Leu Glu Thr Val Pro
370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
            405                 410                 415

Leu Gly Glu Val Ser Asp Met Ala Ala Val Glu Ala Ala Glu Leu Glu
        420                 425                 430

Met Thr Arg Gln Val Leu His Ala Gly Ala Arg Gln Asp Asp Ala Glu
    435                 440                 445

Pro Gly Val Ser Gly Ala Ser Ala His Trp Gly Gln Arg Ala Leu Gln
450                 455                 460

Gly Ala Gln Ala Val Ala Ala Ala Gln Arg Leu Val His Ala Ile Ala
465                 470                 475                 480

Leu Met Thr Gln Phe Gly Arg Ala Gly Ser Thr Asn Thr Pro Gln Glu
                485                 490                 495

Ala Ala Ser Leu Ser Ala Ala Val Phe Gly Leu Gly Glu Ala Ser Ser
            500                 505                 510

Ala Val Ala Glu Thr Val Ser Gly Phe Phe Arg Gly Ser Ser Arg Trp
        515                 520                 525

Ala Gly Gly Phe Gly Val Ala Gly Gly Ala Met Ala Leu Gly Gly Gly
    530                 535                 540

Ile Ala Ala Ala Val Gly Ala Gly Met Ser Leu Thr Asp Asp Ala Pro
545                 550                 555                 560

Ala Gly Gln Lys Ala Ala Ala Gly Ala Glu Ile Ala Leu Gln Leu Thr
                565                 570                 575

Gly Gly Thr Val Glu Leu Ala Ser Ser Ile Ala Leu Ala Leu Ala Ala
            580                 585                 590

Ala Arg Gly Val Thr Ser Gly Leu Gln Val Ala Gly Ala Ser Ala Gly
        595                 600                 605

Ala Ala Ala Gly Ala Leu Ala Ala Leu Ser Pro Met Glu Ile Tyr
    610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Glu Gly Asp Ala Leu Leu Ala Gln
                645                 650                 655

Leu Tyr Arg Asp Lys Thr Ala Ala Glu Gly Ala Val Ala Gly Val Ser
            660                 665                 670

Ala Val Leu Ser Thr Val Gly Ala Ala Val Ser Ile Ala Ala Ala Ala
        675                 680                 685

Ser Val Val Gly Ala Pro Val Ala Val Val Thr Ser Leu Leu Thr Gly
    690                 695                 700

Ala Leu Asn Gly Ile Leu Arg Gly Val Gln Gln Pro Ile Ile Glu Lys
705                 710                 715                 720

Leu Ala Asn Asp Tyr Ala Arg Lys Ile Asp Glu Leu Gly Gly Pro Gln
                725                 730                 735

Ala Tyr Phe Glu Lys Asn Leu Gln Ala Arg His Glu Gln Leu Ala Asn
            740                 745                 750

Ser Asp Gly Leu Arg Lys Met Leu Ala Asp Leu Gln Ala Gly Trp Asn
        755                 760                 765

Ala Ser Ser Val Ile Gly Val Gln Thr Thr Glu Ile Ser Lys Ser Ala
    770                 775                 780

Leu Glu Leu Ala Ala Ile Thr Gly Asn Ala Asp Asn Leu Lys Ser Val
```

```
                785                 790                 795                 800
        Asp Val Phe Val Asp Arg Phe Val Gln Gly Glu Arg Val Ala Gly Gln
                        805                 810                 815

Pro Val Val Leu Asp Val Ala Ala Gly Gly Ile Asp Ile Ala Ser Arg
                        820                 825                 830

Lys Gly Glu Arg Pro Ala Leu Thr Phe Ile Thr Pro Leu Ala Ala Pro
                        835                 840                 845

Gly Glu Glu Gln Arg Arg Thr Lys Thr Gly Lys Ser Glu Phe Thr
        850                 855                 860

Thr Phe Val Glu Ile Val Gly Lys Gln Asp Arg Trp Arg Ile Arg Asp
        865                 870                 875                 880

Gly Ala Ala Asp Thr Thr Ile Asp Leu Ala Lys Val Val Ser Gln Leu
                        885                 890                 895

Val Asp Ala Asn Gly Val Leu Lys His Ser Ile Lys Leu Asp Val Ile
                        900                 905                 910

Gly Gly Asp Gly Asp Asp Val Val Leu Ala Asn Ala Ser Arg Ile His
                        915                 920                 925

Tyr Asp Gly Gly Ala Gly Thr Asn Thr Val Ser Tyr Ala Ala Leu Gly
        930                 935                 940

Arg Gln Asp Ser Ile Thr Val Ser Ala Asp Gly Glu Arg Phe Asn Val
        945                 950                 955                 960

Arg Lys Gln Leu Asn Asn Ala Asn Val Tyr Arg Glu Gly Val Ala Thr
                        965                 970                 975

Gln Thr Thr Ala Tyr Gly Lys Arg Thr Glu Asn Val Gln Tyr Arg His
                        980                 985                 990

Val Glu Leu Ala Arg Val Gly Gln  Val Val Glu Val Asp  Thr Leu Glu
                        995                 1000                1005

His Val  Gln His Ile Ile Gly  Gly Ala Gly Asn Asp  Ser Ile Thr
                 1010                1015                1020

Gly Asn  Ala His Asp Asn Phe  Leu Ala Gly Gly Ser  Gly Asp Asp
                 1025                1030                1035

Arg Leu  Asp Gly Gly Ala Gly  Asn Asp Thr Leu Val  Gly Gly Glu
                 1040                1045                1050

Gly Gln  Asn Thr Val Ile Gly  Gly Ala Gly Asp Asp  Val Phe Leu
                 1055                1060                1065

Gln Asp  Leu Gly Val Trp Ser  Asn Gln Leu Asp Gly  Gly Ala Gly
                 1070                1075                1080

Val Asp  Thr Val Lys Tyr Asn  Val His Gln Pro Ser  Glu Glu Arg
                 1085                1090                1095

Leu Glu  Arg Met Gly Asp Thr  Gly Ile His Ala Asp  Leu Gln Lys
                 1100                1105                1110

Gly Thr  Val Glu Lys Trp Pro  Ala Leu Asn Leu Phe  Ser Val Asp
                 1115                1120                1125

His Val  Lys Asn Ile Glu Asn  Leu His Gly Ser Arg  Leu Asn Asp
                 1130                1135                1140

Arg Ile  Ala Gly Asp Asp Gln  Asp Asn Glu Leu Trp  Gly His Asp
                 1145                1150                1155

Gly Asn  Asp Thr Ile Arg Gly  Arg Gly Gly Asp Asp  Ile Leu Arg
                 1160                1165                1170

Gly Gly  Leu Gly Leu Asp Thr  Leu Tyr Gly Glu Asp  Gly Asn Asp
                 1175                1180                1185

Ile Phe  Leu Gln Asp Asp Glu  Thr Val Ser Asp Asp  Ile Asp Gly
                 1190                1195                1200
```

-continued

Gly Ala Gly Leu Asp Thr Val Asp Tyr Ser Ala Met Ile His Pro
1205                1210                1215

Gly Arg Ile Val Ala Pro His Glu Tyr Gly Phe Gly Ile Glu Ala
1220                1225                1230

Asp Leu Ser Arg Glu Trp Val Arg Lys Ala Ser Ala Leu Gly Val
1235                1240                1245

Asp Tyr Tyr Asp Asn Val Arg Asn Val Glu Asn Val Ile Gly Thr
1250                1255                1260

Ser Met Lys Asp Val Leu Ile Gly Asp Ala Gln Ala Asn Thr Leu
1265                1270                1275

Met Gly Gln Gly Gly Asp Asp Thr Val Arg Gly Gly Asp Gly Asp
1280                1285                1290

Asp Leu Leu Phe Gly Gly Asp Gly Asn Asp Met Leu Tyr Gly Asp
1295                1300                1305

Ala Gly Asn Asp Thr Leu Tyr Gly Gly Leu Gly Asp Asp Thr Leu
1310                1315                1320

Glu Gly Gly Ala Gly Asn Asp Trp Phe Gly Gln Thr Gln Ala Arg
1325                1330                1335

Glu His Asp Val Leu Arg Gly Gly Asp Gly Val Asp Thr Val Asp
1340                1345                1350

Tyr Ser Gln Thr Gly Ala His Ala Gly Ile Ala Ala Gly Arg Ile
1355                1360                1365

Gly Leu Gly Ile Leu Ala Asp Leu Gly Ala Gly Arg Val Asp Lys
1370                1375                1380

Leu Gly Glu Ala Gly Ser Ser Ala Tyr Asp Thr Val Ser Gly Ile
1385                1390                1395

Glu Asn Val Val Gly Thr Glu Leu Ala Asp Arg Ile Thr Gly Asp
1400                1405                1410

Ala Gln Ala Asn Val Leu Arg Gly Ala Gly Gly Ala Asp Val Leu
1415                1420                1425

Ala Gly Gly Glu Gly Asp Asp Val Leu Leu Gly Gly Asp Gly Asp
1430                1435                1440

Asp Gln Leu Ser Gly Asp Ala Gly Arg Asp Arg Leu Tyr Gly Glu
1445                1450                1455

Ala Gly Asp Asp Trp Phe Phe Gln Asp Ala Ala Asn Ala Gly Asn
1460                1465                1470

Leu Leu Asp Gly Gly Asp Gly Arg Asp Thr Val Asp Phe Ser Gly
1475                1480                1485

Pro Gly Arg Gly Leu Asp Ala Gly Ala Lys Gly Val Phe Leu Ser
1490                1495                1500

Leu Gly Lys Gly Phe Ala Ser Leu Met Asp Glu Pro Glu Thr Ser
1505                1510                1515

Asn Val Leu Arg Asn Ile Glu Asn Ala Val Gly Ser Ala Arg Asp
1520                1525                1530

Asp Val Leu Ile Gly Asp Ala Gly Ala Asn Val Leu Asn Gly Leu
1535                1540                1545

Ala Gly Asn Asp Val Leu Ser Gly Gly Ala Gly Asp Asp Val Leu
1550                1555                1560

Leu Gly Asp Glu Gly Ser Asp Leu Leu Ser Gly Asp Ala Gly Asn
1565                1570                1575

Asp Asp Leu Phe Gly Gly Gln Gly Asp Asp Thr Tyr Leu Phe Gly
1580                1585                1590

Val Gly Tyr Gly His Asp Thr Ile Tyr Glu Ser Gly Gly Gly His
    1595                1600                1605

Asp Thr Ile Arg Ile Asn Ala Gly Ala Asp Gln Leu Trp Phe Ala
    1610                1615                1620

Arg Gln Gly Asn Asp Leu Glu Ile Arg Ile Leu Gly Thr Asp Asp
    1625                1630                1635

Ala Leu Thr Val His Asp Trp Tyr Arg Asp Ala Asp His Arg Val
    1640                1645                1650

Glu Ile Ile His Ala Ala Asn Gln Ala Val Asp Gln Ala Gly Ile
    1655                1660                1665

Glu Lys Leu Val Glu Ala Met Ala Gln Tyr Pro Asp Pro Gly Ala
    1670                1675                1680

Ala Ala Ala Ala Pro Pro Ala Ala Arg Val Pro Asp Thr Leu Met
    1685                1690                1695

Gln Ser Leu Ala Val Asn Trp Arg
    1700                1705

<210> SEQ ID NO 2
<211> LENGTH: 1706
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
                20                  25                  30

Glu Lys Asn Ala Thr Leu Met Phe Arg Leu Val Asn Pro His Ser Thr
            35                  40                  45

Ser Leu Ile Ala Glu Gly Val Ala Thr Lys Gly Leu Gly Val His Ala
        50                  55                  60

Lys Ser Ser Asp Trp Gly Leu Gln Ala Gly Tyr Ile Pro Val Asn Pro
65              70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

-continued

```
Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
                405                 410                 415

Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
        435                 440                 445

Pro Gly Val Ser Gly Ala Ser Ala His Trp Gly Gln Arg Ala Leu Gln
    450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
                485                 490                 495

Ala Ala Ser Leu Ser Ala Ala Val Phe Gly Leu Gly Glu Ala Ser Ser
            500                 505                 510

Ala Val Ala Glu Thr Val Ser Gly Phe Phe Arg Gly Ser Ser Arg Trp
        515                 520                 525

Ala Gly Gly Phe Gly Val Ala Gly Gly Ala Met Ala Leu Gly Gly Gly
    530                 535                 540

Ile Ala Ala Ala Val Gly Ala Gly Met Ser Leu Thr Asp Asp Ala Pro
545                 550                 555                 560

Ala Gly Gln Lys Ala Ala Ala Gly Ala Gln Ile Ala Leu Gln Leu Thr
                565                 570                 575

Gly Gly Thr Val Glu Leu Ala Ser Ser Ile Ala Leu Ala Leu Ala Ala
            580                 585                 590

Ala Arg Gly Val Thr Ser Gly Leu Gln Val Ala Gly Ala Ser Ala Gly
        595                 600                 605

Ala Ala Ala Gly Ala Leu Ala Ala Leu Ser Pro Met Glu Ile Tyr
    610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Glu Gly Asp Ala Leu Leu Ala Gln
                645                 650                 655
```

```
Leu Tyr Arg Asp Lys Thr Ala Ala Glu Gly Ala Val Ala Gly Val Ser
            660                 665                 670

Ala Val Leu Ser Thr Val Gly Ala Ala Val Ser Ile Ala Ala Ala Ala
            675                 680                 685

Ser Val Val Gly Ala Pro Val Ala Val Val Thr Ser Leu Leu Thr Gly
            690                 695                 700

Ala Leu Asn Gly Ile Leu Arg Gly Val Gln Gln Pro Ile Ile Glu Lys
705                 710                 715                 720

Leu Ala Asn Asp Tyr Ala Arg Lys Ile Asp Glu Leu Gly Gly Pro Gln
            725                 730                 735

Ala Tyr Phe Glu Lys Asn Leu Gln Ala Arg His Glu Gln Leu Ala Asn
            740                 745                 750

Ser Asp Gly Leu Arg Lys Met Leu Ala Asp Leu Gln Ala Gly Trp Asn
            755                 760                 765

Ala Ser Ser Val Ile Gly Val Gln Thr Thr Glu Ile Ser Lys Ser Ala
            770                 775                 780

Leu Glu Leu Ala Ala Ile Thr Gly Asn Ala Asp Asn Leu Lys Ser Val
785                 790                 795                 800

Asp Val Phe Val Asp Arg Phe Val Gln Gly Glu Arg Val Ala Gly Gln
            805                 810                 815

Pro Val Val Leu Asp Val Ala Ala Gly Gly Ile Asp Ile Ala Ser Arg
            820                 825                 830

Lys Gly Glu Arg Pro Ala Leu Thr Phe Ile Thr Pro Leu Ala Ala Pro
            835                 840                 845

Gly Glu Glu Gln Arg Arg Thr Lys Thr Gly Arg Ser Glu Phe Thr
            850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
            885                 890                 895

Val Asp Ala Asn Gly Val Leu Lys His Ser Ile Lys Leu Asp Val Ile
            900                 905                 910

Gly Gly Asp Gly Asp Val Val Leu Ala Asn Ala Ser Arg Ile His
            915                 920                 925

Tyr Asp Gly Gly Ala Gly Thr Asn Thr Val Ser Tyr Ala Ala Leu Gly
            930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
            965                 970                 975

Gln Thr Thr Ala Tyr Gly Lys Arg Thr Glu Asn Val Gln Tyr Arg His
            980                 985                 990

Val Glu Leu Ala Arg Val Gly Gln Val Val Glu Val Asp Thr Leu Glu
            995                 1000                1005

His Val Gln His Ile Ile Gly Gly Ala Gly Asn Asp Ser Ile Thr
            1010                1015                1020

Gly Asn Ala His Asp Asn Phe Leu Ala Gly Gly Ser Gly Asp Asp
            1025                1030                1035

Arg Leu Asp Gly Gly Ala Gly Asn Asp Thr Leu Val Gly Gly Glu
            1040                1045                1050

Gly Gln Asn Thr Val Ile Gly Gly Ala Gly Asp Asp Val Phe Leu
            1055                1060                1065

Gln Asp Leu Gly Val Trp Ser Asn Gln Leu Asp Gly Gly Ala Gly
```

1070                1075                1080
Val Asp Thr Val Lys Tyr Asn Val His Gln Pro Ser Glu Glu Arg
    1085                1090                1095

Leu Glu Arg Met Gly Asp Thr Gly Ile His Ala Asp Leu Gln Lys
    1100                1105                1110

Gly Thr Val Glu Lys Trp Pro Ala Leu Asn Leu Phe Ser Val Asp
    1115                1120                1125

His Val Lys Asn Ile Glu Asn Leu His Gly Ser Arg Leu Asn Asp
    1130                1135                1140

Arg Ile Ala Gly Asp Asp Gln Asp Asn Glu Leu Trp Gly His Asp
    1145                1150                1155

Gly Asn Asp Thr Ile Arg Gly Arg Gly Gly Asp Ile Leu Arg
    1160                1165                1170

Gly Gly Leu Gly Leu Asp Thr Leu Tyr Gly Glu Asp Gly Asn Asp
    1175                1180                1185

Ile Phe Leu Gln Asp Asp Glu Thr Val Ser Asp Ile Asp Gly
    1190                1195                1200

Gly Ala Gly Leu Asp Thr Val Asp Tyr Ser Ala Met Ile His Pro
    1205                1210                1215

Gly Arg Ile Val Ala Pro His Glu Tyr Gly Phe Gly Ile Glu Ala
    1220                1225                1230

Asp Leu Ser Arg Glu Trp Val Arg Lys Ala Ser Ala Leu Gly Val
    1235                1240                1245

Asp Tyr Tyr Asp Asn Val Arg Asn Val Glu Asn Val Ile Gly Thr
    1250                1255                1260

Ser Met Lys Asp Val Leu Ile Gly Asp Ala Gln Ala Asn Thr Leu
    1265                1270                1275

Met Gly Gln Gly Gly Asp Asp Thr Val Arg Gly Gly Asp Gly Asp
    1280                1285                1290

Asp Leu Leu Phe Gly Gly Asp Gly Asn Asp Met Leu Tyr Gly Asp
    1295                1300                1305

Ala Gly Asn Asp Thr Leu Tyr Gly Gly Leu Gly Asp Asp Thr Leu
    1310                1315                1320

Glu Gly Gly Ala Gly Asn Asp Trp Phe Gly Gln Thr Gln Ala Arg
    1325                1330                1335

Glu His Asp Val Leu Arg Gly Gly Asp Gly Val Asp Thr Val Asp
    1340                1345                1350

Tyr Ser Gln Thr Gly Ala His Ala Gly Ile Ala Ala Gly Arg Ile
    1355                1360                1365

Gly Leu Gly Ile Leu Ala Asp Leu Gly Ala Gly Arg Val Asp Lys
    1370                1375                1380

Leu Gly Glu Ala Gly Ser Ser Ala Tyr Asp Thr Val Ser Gly Ile
    1385                1390                1395

Glu Asn Val Val Gly Thr Glu Leu Ala Asp Arg Ile Thr Gly Asp
    1400                1405                1410

Ala Gln Ala Asn Val Leu Arg Gly Ala Gly Gly Ala Asp Val Leu
    1415                1420                1425

Ala Gly Gly Glu Gly Asp Asp Val Leu Leu Gly Gly Asp Gly Asp
    1430                1435                1440

Asp Gln Leu Ser Gly Asp Ala Gly Arg Asp Arg Leu Tyr Gly Glu
    1445                1450                1455

Ala Gly Asp Asp Trp Phe Phe Gln Asp Ala Ala Asn Ala Gly Asn
    1460                1465                1470

```
Leu Leu Asp Gly Gly Asp Gly Arg Asp Thr Val Asp Phe Ser Gly
    1475                1480                1485

Pro Gly Arg Gly Leu Asp Ala Gly Ala Lys Gly Val Phe Leu Ser
    1490                1495                1500

Leu Gly Lys Gly Phe Ala Ser Leu Met Asp Glu Pro Glu Thr Ser
    1505                1510                1515

Asn Val Leu Arg Asn Ile Glu Asn Ala Val Gly Ser Ala Arg Asp
    1520                1525                1530

Asp Val Leu Ile Gly Asp Ala Gly Ala Asn Val Leu Asn Gly Leu
    1535                1540                1545

Ala Gly Asn Asp Val Leu Ser Gly Gly Ala Gly Asp Asp Val Leu
    1550                1555                1560

Leu Gly Asp Glu Gly Ser Asp Leu Leu Ser Gly Asp Ala Gly Asn
    1565                1570                1575

Asp Asp Leu Phe Gly Gly Gln Gly Asp Asp Thr Tyr Leu Phe Gly
    1580                1585                1590

Val Gly Tyr Gly His Asp Thr Ile Tyr Glu Ser Gly Gly Gly His
    1595                1600                1605

Asp Thr Ile Arg Ile Asn Ala Gly Ala Asp Gln Leu Trp Phe Ala
    1610                1615                1620

Arg Gln Gly Asn Asp Leu Glu Ile Arg Ile Leu Gly Thr Asp Asp
    1625                1630                1635

Ala Leu Thr Val His Asp Trp Tyr Arg Asp Ala Asp His Arg Val
    1640                1645                1650

Glu Ile Ile His Ala Ala Asn Gln Ala Val Asp Gln Ala Gly Ile
    1655                1660                1665

Glu Lys Leu Val Glu Ala Met Ala Gln Tyr Pro Asp Pro Gly Ala
    1670                1675                1680

Ala Ala Ala Ala Pro Pro Ala Ala Arg Val Pro Asp Thr Leu Met
    1685                1690                1695

Gln Ser Leu Ala Val Asn Trp Arg
    1700                1705
```

<210> SEQ ID NO 3
<211> LENGTH: 1708
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
                20                  25                  30

Glu Lys Asn Ala Thr Leu Met Phe Arg Leu Val Asn Pro His Ser Thr
            35                  40                  45

Ser Leu Ile Ala Glu Gly Val Ala Thr Lys Gly Leu Gly Val His Ala
        50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
```

```
                100                 105                 110
Leu Thr Leu Ser Lys Glu Arg Leu Asp Tyr Leu Arg Gln Ala Gly Leu
            115                 120                 125
Val Thr Gly Met Ala Asp Gly Val Val Ala Ser Asn His Ala Gly Tyr
        130                 135                 140
Glu Gln Phe Glu Phe Arg Val Lys Glu Thr Ser Asp Gly Arg Tyr Ala
145                 150                 155                 160
Val Gln Tyr Arg Arg Lys Gly Gly Asp Phe Glu Ala Val Lys Val
                165                 170                 175
Ile Gly Asn Ala Ala Gly Ile Pro Leu Thr Ala Asp Gly Ser Ile Asp
            180                 185                 190
Met Phe Ala Ile Met Pro His Leu Ser Asn Phe Arg Asp Ser Ala Arg
        195                 200                 205
Ser Ser Val Thr Ser Gly Asp Ser Val Thr Asp Tyr Leu Ala Arg Thr
    210                 215                 220
Arg Arg Ala Ala Ser Glu Ala Thr Gly Gly Leu Asp Arg Glu Arg Ile
225                 230                 235                 240
Asp Leu Leu Trp Lys Ile Ala Arg Ala Gly Ala Arg Ser Ala Val Gly
                245                 250                 255
Thr Glu Ala Arg Arg Gln Phe Arg Tyr Asp Gly Asp Met Asn Ile Gly
            260                 265                 270
Val Ile Thr Asp Phe Glu Leu Glu Val Arg Asn Ala Leu Asn Arg Arg
        275                 280                 285
Ala His Ala Val Gly Ala Gln Asp Val Val Gln His Gly Thr Glu Gln
    290                 295                 300
Asn Asn Pro Phe Pro Glu Ala Asp Glu Lys Ile Phe Val Val Ser Ala
305                 310                 315                 320
Thr Gly Glu Ser Gln Met Leu Thr Arg Gly Gln Leu Lys Glu Tyr Ile
                325                 330                 335
Gly Gln Gln Arg Gly Glu Gly Tyr Val Phe Tyr Glu Asn Arg Ala Tyr
            340                 345                 350
Gly Val Ala Gly Lys Ser Leu Phe Asp Asp Gly Leu Gly Ala Ala Pro
        355                 360                 365
Gly Val Pro Ser Gly Arg Ser Lys Phe Ser Pro Asp Val Leu Glu Thr
    370                 375                 380
Val Pro Ala Ser Pro Gly Leu Arg Arg Pro Ser Leu Gly Ala Val Glu
385                 390                 395                 400
Arg Gln Asp Ser Gly Tyr Asp Ser Leu Asp Gly Val Gly Ser Arg Ser
                405                 410                 415
Phe Ser Leu Gly Glu Val Ser Asp Met Ala Ala Val Glu Ala Ala Glu
            420                 425                 430
Leu Glu Met Thr Arg Gln Val Leu His Ala Gly Ala Arg Gln Asp Asp
        435                 440                 445
Ala Glu Pro Gly Val Ser Gly Ala Ser Ala His Trp Gly Gln Arg Ala
    450                 455                 460
Leu Gln Gly Ala Gln Ala Val Ala Ala Gln Arg Leu Val His Ala
465                 470                 475                 480
Ile Ala Leu Met Thr Gln Phe Gly Arg Ala Gly Ser Thr Asn Thr Pro
                485                 490                 495
Gln Glu Ala Ala Ser Leu Ser Ala Ala Val Phe Gly Leu Gly Glu Ala
            500                 505                 510
Ser Ser Ala Val Ala Glu Thr Val Ser Gly Phe Phe Arg Gly Ser Ser
        515                 520                 525
```

-continued

```
Arg Trp Ala Gly Gly Phe Gly Val Ala Gly Ala Met Ala Leu Gly
    530                 535                 540
Gly Gly Ile Ala Ala Ala Val Gly Ala Gly Met Ser Leu Thr Asp Asp
545                 550                 555                 560
Ala Pro Ala Gly Gln Lys Ala Ala Gly Ala Gln Ile Ala Leu Gln
                565                 570                 575
Leu Thr Gly Gly Thr Val Glu Leu Ala Ser Ser Ile Ala Leu Ala Leu
                580                 585                 590
Ala Ala Ala Arg Gly Val Thr Ser Gly Leu Gln Val Ala Gly Ala Ser
                595                 600                 605
Ala Gly Ala Ala Ala Gly Ala Leu Ala Ala Ala Leu Ser Pro Met Glu
610                 615                 620
Ile Tyr Gly Leu Val Gln Gln Ser His Tyr Ala Asp Gln Leu Asp Lys
625                 630                 635                 640
Leu Ala Gln Glu Ser Ser Ala Tyr Gly Tyr Glu Gly Asp Ala Leu Leu
                645                 650                 655
Ala Gln Leu Tyr Arg Asp Lys Thr Ala Ala Glu Gly Ala Val Ala Gly
                660                 665                 670
Val Ser Ala Val Leu Ser Thr Val Gly Ala Ala Val Ser Ile Ala Ala
                675                 680                 685
Ala Ala Ser Val Val Gly Ala Pro Val Ala Val Thr Ser Leu Leu
690                 695                 700
Thr Gly Ala Leu Asn Gly Ile Leu Arg Gly Val Gln Gln Pro Ile Ile
705                 710                 715                 720
Glu Lys Leu Ala Asn Asp Tyr Ala Arg Lys Ile Asp Glu Leu Gly Gly
                725                 730                 735
Pro Gln Ala Tyr Phe Glu Lys Asn Leu Gln Ala Arg His Glu Gln Leu
                740                 745                 750
Ala Asn Ser Asp Gly Leu Arg Lys Met Leu Ala Asp Leu Gln Ala Gly
                755                 760                 765
Trp Asn Ala Ser Ser Val Ile Gly Val Gln Thr Thr Glu Ile Ser Lys
770                 775                 780
Ser Ala Leu Glu Leu Ala Ala Ile Thr Gly Asn Ala Asp Asn Leu Lys
785                 790                 795                 800
Ser Val Asp Val Phe Val Asp Arg Phe Val Gln Gly Glu Arg Val Ala
                805                 810                 815
Gly Gln Pro Val Val Leu Asp Val Ala Ala Gly Gly Ile Asp Ile Ala
                820                 825                 830
Ser Arg Lys Gly Glu Arg Pro Ala Leu Thr Phe Ile Thr Pro Leu Ala
                835                 840                 845
Ala Pro Gly Glu Glu Gln Arg Arg Arg Thr Lys Thr Gly Arg Ser Glu
850                 855                 860
Phe Thr Thr Phe Val Glu Ile Val Gly Lys Gln Asp Arg Trp Arg Ile
865                 870                 875                 880
Arg Asp Gly Ala Ala Asp Thr Thr Ile Asp Leu Ala Lys Val Val Ser
                885                 890                 895
Gln Leu Val Asp Ala Asn Gly Val Leu Lys His Ser Ile Lys Leu Asp
                900                 905                 910
Val Ile Gly Gly Asp Gly Asp Val Val Leu Ala Asn Ala Ser Arg
                915                 920                 925
Ile His Tyr Asp Gly Gly Ala Gly Thr Asn Thr Val Ser Tyr Ala Ala
930                 935                 940
```

-continued

```
Leu Gly Arg Gln Asp Ser Ile Thr Val Ser Ala Asp Gly Glu Arg Phe
945                 950                 955                 960

Asn Val Arg Lys Gln Leu Asn Asn Ala Asn Val Tyr Arg Glu Gly Val
                965                 970                 975

Ala Thr Gln Thr Thr Ala Tyr Gly Lys Arg Thr Glu Asn Val Gln Tyr
            980                 985                 990

Arg His Val Glu Leu Ala Arg Val  Gly Gln Val Val Glu  Val Asp Thr
        995                 1000                1005

Leu Glu  His Val Gln His Ile  Ile Gly Gly Ala Gly  Asn Asp Ser
    1010                1015                1020

Ile Thr  Gly Asn Ala His Asp  Asn Phe Leu Ala Gly  Gly Ser Gly
    1025                1030                1035

Asp Asp  Arg Leu Asp Gly Gly  Ala Gly Asn Asp Thr  Leu Val Gly
    1040                1045                1050

Gly Glu  Gly Gln Asn Thr Val  Ile Gly Gly Ala Gly  Asp Asp Val
    1055                1060                1065

Phe Leu  Gln Asp Leu Gly Val  Trp Ser Asn Gln Leu  Asp Gly Gly
    1070                1075                1080

Ala Gly  Val Asp Thr Val Lys  Tyr Asn Val His Gln  Pro Ser Glu
    1085                1090                1095

Glu Arg  Leu Glu Arg Met Gly  Asp Thr Gly Ile His  Ala Asp Leu
    1100                1105                1110

Gln Lys  Gly Thr Val Glu Lys  Trp Pro Ala Leu Asn  Leu Phe Ser
    1115                1120                1125

Val Asp  His Val Lys Asn Ile  Glu Asn Leu His Gly  Ser Arg Leu
    1130                1135                1140

Asn Asp  Arg Ile Ala Gly Asp  Gln Asp Asn Glu Leu  Leu Trp Gly
    1145                1150                1155

His Asp  Gly Asn Asp Thr Ile  Arg Gly Arg Gly Gly  Asp Asp Ile
    1160                1165                1170

Leu Arg  Gly Gly Leu Gly Leu  Asp Thr Leu Tyr Gly  Glu Asp Gly
    1175                1180                1185

Asn Asp  Ile Phe Leu Gln Asp  Asp Glu Thr Val Ser  Asp Asp Ile
    1190                1195                1200

Asp Gly  Gly Ala Gly Leu Asp  Thr Val Asp Tyr Ser  Ala Met Ile
    1205                1210                1215

His Pro  Gly Arg Ile Val Ala  Pro His Glu Tyr Gly  Phe Gly Ile
    1220                1225                1230

Glu Ala  Asp Leu Ser Arg Glu  Trp Val Arg Lys Ala  Ser Ala Leu
    1235                1240                1245

Gly Val  Asp Tyr Tyr Asp Asn  Val Arg Asn Val Glu  Asn Val Ile
    1250                1255                1260

Gly Thr  Ser Met Lys Asp Val  Leu Ile Gly Asp Ala  Gln Ala Asn
    1265                1270                1275

Thr Leu  Met Gly Gln Gly Gly  Asp Asp Thr Val Arg  Gly Gly Asp
    1280                1285                1290

Gly Asp  Asp Leu Leu Phe Gly  Gly Asp Gly Asn Asp  Met Leu Tyr
    1295                1300                1305

Gly Asp  Ala Gly Asn Asp Thr  Leu Tyr Gly Gly Leu  Gly Asp Asp
    1310                1315                1320

Thr Leu  Glu Gly Gly Ala Gly  Asn Asp Trp Phe Gly  Gln Thr Gln
    1325                1330                1335

Ala Arg  Glu His Asp Val Leu  Arg Gly Gly Asp Gly  Val Asp Thr
```

```
            1340                1345                1350
Val Asp Tyr Ser Gln Thr Gly Ala His Ala Gly Ile Ala Ala Gly
    1355                1360                1365

Arg Ile Gly Leu Gly Ile Leu Ala Asp Leu Gly Ala Gly Arg Val
    1370                1375                1380

Asp Lys Leu Gly Glu Ala Gly Ser Ser Ala Tyr Asp Thr Val Ser
    1385                1390                1395

Gly Ile Glu Asn Val Val Gly Thr Glu Leu Ala Asp Arg Ile Thr
    1400                1405                1410

Gly Asp Ala Gln Ala Asn Val Leu Arg Gly Ala Gly Gly Ala Asp
    1415                1420                1425

Val Leu Ala Gly Gly Glu Gly Asp Asp Val Leu Leu Gly Gly Asp
    1430                1435                1440

Gly Asp Asp Gln Leu Ser Gly Asp Ala Gly Arg Asp Arg Leu Tyr
    1445                1450                1455

Gly Glu Ala Gly Asp Asp Trp Phe Phe Gln Asp Ala Ala Asn Ala
    1460                1465                1470

Gly Asn Leu Leu Asp Gly Gly Asp Gly Arg Asp Thr Val Asp Phe
    1475                1480                1485

Ser Gly Pro Gly Arg Gly Leu Asp Ala Gly Ala Lys Gly Val Phe
    1490                1495                1500

Leu Ser Leu Gly Lys Gly Phe Ala Ser Leu Met Asp Glu Pro Glu
    1505                1510                1515

Thr Ser Asn Val Leu Arg Asn Ile Glu Asn Ala Val Gly Ser Ala
    1520                1525                1530

Arg Asp Asp Val Leu Ile Gly Asp Ala Gly Ala Asn Val Leu Asn
    1535                1540                1545

Gly Leu Ala Gly Asn Asp Val Leu Ser Gly Gly Ala Gly Asp Asp
    1550                1555                1560

Val Leu Leu Gly Asp Glu Gly Ser Asp Leu Leu Ser Gly Asp Ala
    1565                1570                1575

Gly Asn Asp Asp Leu Phe Gly Gly Gln Gly Asp Asp Thr Tyr Leu
    1580                1585                1590

Phe Gly Val Gly Tyr Gly His Asp Thr Ile Tyr Glu Ser Gly Gly
    1595                1600                1605

Gly His Asp Thr Ile Arg Ile Asn Ala Gly Ala Asp Gln Leu Trp
    1610                1615                1620

Phe Ala Arg Gln Gly Asn Asp Leu Glu Ile Arg Ile Leu Gly Thr
    1625                1630                1635

Asp Asp Ala Leu Thr Val His Asp Trp Tyr Arg Asp Ala Asp His
    1640                1645                1650

Arg Val Glu Ile Ile His Ala Ala Asn Gln Ala Val Asp Gln Ala
    1655                1660                1665

Gly Ile Glu Lys Leu Val Glu Ala Met Ala Gln Tyr Pro Asp Pro
    1670                1675                1680

Gly Ala Ala Ala Ala Pro Pro Ala Ala Arg Val Pro Asp Thr
    1685                1690                1695

Leu Met Gln Ser Leu Ala Val Asn Trp Arg
    1700                1705

<210> SEQ ID NO 4
<211> LENGTH: 1720
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 4

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Asp Asp Phe Glu Ala Val Lys Val
                165                 170                 175

Ile Gly Asn Ala Ala Gly Ile Pro Leu Thr Ala Asp Gly Ser Ile Asp
            180                 185                 190

Met Phe Ala Ile Met Pro His Leu Ser Asn Phe Arg Asp Ser Ala Arg
        195                 200                 205

Ser Ser Val Thr Ser Gly Asp Ser Val Thr Asp Tyr Leu Ala Arg Thr
    210                 215                 220

Arg Arg Ala Ala Ser Glu Ala Thr Gly Gly Val Leu Ser Ile Ile Asn
225                 230                 235                 240

Phe Glu Lys Leu Val His Leu Asp Arg Glu Arg Ile Asp Leu Leu Trp
                245                 250                 255

Lys Ile Ala Arg Ala Gly Ala Arg Ser Ala Val Gly Thr Glu Ala Arg
            260                 265                 270

Arg Gln Phe Arg Tyr Asp Gly Asp Met Asn Ile Gly Val Ile Thr Asp
        275                 280                 285

Phe Glu Leu Glu Val Arg Asn Ala Leu Asn Arg Ala His Ala Val
    290                 295                 300

Gly Ala Gln Asp Val Val Gln His Gly Thr Glu Gln Asn Asn Pro Phe
305                 310                 315                 320

Pro Glu Ala Asp Glu Lys Ile Phe Val Val Ser Ala Thr Gly Glu Ser
                325                 330                 335

Gln Met Leu Thr Arg Gly Gln Leu Lys Glu Tyr Ile Gly Gln Gln Arg
            340                 345                 350

Gly Glu Gly Tyr Val Phe Tyr Glu Asn Arg Ala Tyr Gly Val Ala Gly
        355                 360                 365

Lys Ser Leu Phe Asp Asp Gly Leu Gly Ala Ala Pro Gly Val Pro Ser
    370                 375                 380

Gly Arg Ser Lys Phe Ser Pro Asp Val Leu Glu Thr Val Pro Ala Ser

```
385                 390                 395                 400
Pro Gly Leu Arg Arg Pro Ser Leu Gly Ala Val Glu Arg Gln Asp Ser
                405                 410                 415
Gly Tyr Asp Ser Leu Asp Gly Val Gly Ser Arg Ser Phe Ser Leu Gly
                420                 425                 430
Glu Val Ser Asp Met Ala Ala Val Glu Ala Ala Glu Leu Glu Met Thr
                435                 440                 445
Arg Gln Val Leu His Ala Gly Arg Gln Asp Asp Ala Glu Pro Gly
    450                 455                 460
Val Ser Gly Ala Ser Ala His Trp Gly Gln Arg Ala Leu Gln Gly Ala
465                 470                 475                 480
Gln Ala Val Ala Ala Gln Arg Leu Val His Ala Ile Ala Leu Met
                485                 490                 495
Thr Gln Phe Gly Arg Ala Gly Ser Thr Asn Thr Pro Gln Glu Ala Ala
                500                 505                 510
Ser Leu Ser Ala Ala Val Phe Gly Leu Gly Glu Ala Ser Ser Ala Val
                515                 520                 525
Ala Glu Thr Val Ser Gly Phe Phe Arg Gly Ser Ser Arg Trp Ala Gly
    530                 535                 540
Gly Phe Gly Val Ala Gly Gly Ala Met Ala Leu Gly Gly Gly Ile Ala
545                 550                 555                 560
Ala Ala Val Gly Ala Gly Met Ser Leu Thr Asp Asp Ala Pro Ala Gly
                565                 570                 575
Gln Lys Ala Ala Ala Gly Ala Gln Ile Ala Leu Gln Leu Thr Gly Gly
                580                 585                 590
Thr Val Glu Leu Ala Ser Ser Ile Ala Leu Ala Leu Ala Ala Ala Arg
    595                 600                 605
Gly Val Thr Ser Gly Leu Gln Val Ala Gly Ala Ser Ala Gly Ala Ala
    610                 615                 620
Ala Gly Ala Leu Ala Ala Ala Leu Ser Pro Met Glu Ile Tyr Gly Leu
625                 630                 635                 640
Val Gln Gln Ser His Tyr Ala Asp Gln Leu Asp Lys Leu Ala Gln Glu
                645                 650                 655
Ser Ser Ala Tyr Gly Tyr Glu Gly Asp Ala Leu Leu Ala Gln Leu Tyr
                660                 665                 670
Arg Asp Lys Thr Ala Ala Glu Gly Ala Val Ala Gly Val Ser Ala Val
                675                 680                 685
Leu Ser Thr Val Gly Ala Ala Val Ser Ile Ala Ala Ala Ser Val
    690                 695                 700
Val Gly Ala Pro Val Ala Val Thr Ser Leu Leu Thr Gly Ala Leu
705                 710                 715                 720
Asn Gly Ile Leu Arg Gly Val Gln Gln Pro Ile Ile Glu Lys Leu Ala
                725                 730                 735
Asn Asp Tyr Ala Arg Lys Ile Asp Glu Leu Gly Gly Pro Gln Ala Tyr
                740                 745                 750
Phe Glu Lys Asn Leu Gln Ala Arg His Glu Gln Leu Ala Asn Ser Asp
                755                 760                 765
Gly Leu Arg Lys Met Leu Ala Asp Leu Gln Ala Gly Trp Asn Ala Ser
                770                 775                 780
Ser Val Ile Gly Val Gln Thr Thr Glu Ile Ser Lys Ser Ala Leu Glu
785                 790                 795                 800
Leu Ala Ala Ile Thr Gly Asn Ala Asp Asn Leu Lys Ser Val Asp Val
                805                 810                 815
```

-continued

```
Phe Val Asp Arg Phe Val Gln Gly Glu Arg Val Ala Gly Gln Pro Val
            820                 825                 830

Val Leu Asp Val Ala Ala Gly Ile Asp Ile Ala Ser Arg Lys Gly
            835                 840                 845

Glu Arg Pro Ala Leu Thr Phe Ile Thr Pro Leu Ala Ala Pro Gly Glu
    850                 855                 860

Glu Gln Arg Arg Thr Lys Thr Gly Arg Ser Glu Phe Thr Thr Phe
865                 870                 875                 880

Val Glu Ile Val Gly Lys Gln Asp Arg Trp Arg Ile Arg Asp Gly Ala
                885                 890                 895

Ala Asp Thr Thr Ile Asp Leu Ala Lys Val Val Ser Gln Leu Val Asp
            900                 905                 910

Ala Asn Gly Val Leu Lys His Ser Ile Lys Leu Asp Val Ile Gly Gly
            915                 920                 925

Asp Gly Asp Asp Val Val Leu Ala Asn Ala Ser Arg Ile His Tyr Asp
    930                 935                 940

Gly Gly Ala Gly Thr Asn Thr Val Ser Tyr Ala Ala Leu Gly Arg Gln
945                 950                 955                 960

Asp Ser Ile Thr Val Ser Ala Asp Gly Glu Arg Phe Asn Val Arg Lys
                965                 970                 975

Gln Leu Asn Asn Ala Asn Val Tyr Arg Glu Gly Val Ala Thr Gln Thr
            980                 985                 990

Thr Ala Tyr Gly Lys Arg Thr Glu Asn Val Gln Tyr Arg His Val Glu
            995                 1000                1005

Leu Ala Arg Val Gly Gln Val  Val Glu Val Asp Thr  Leu Glu His
    1010                1015                1020

Val Gln His Ile Ile Gly Gly  Ala Gly Asn Asp Ser  Ile Thr Gly
    1025                1030                1035

Asn Ala His Asp Asn Phe Leu  Ala Gly Gly Ser Gly  Asp Asp Arg
    1040                1045                1050

Leu Asp Gly Gly Ala Gly Asn  Asp Thr Leu Val Gly  Gly Glu Gly
    1055                1060                1065

Gln Asn Thr Val Ile Gly Gly  Ala Gly Asp Val  Phe Leu Gln
    1070                1075                1080

Asp Leu Gly Val Trp Ser Asn  Gln Leu Asp Gly Gly  Ala Gly Val
    1085                1090                1095

Asp Thr Val Lys Tyr Asn Val  His Gln Pro Ser Glu  Glu Arg Leu
    1100                1105                1110

Glu Arg Met Gly Asp Thr Gly  Ile His Ala Asp Leu  Gln Lys Gly
    1115                1120                1125

Thr Val Glu Lys Trp Pro Ala  Leu Asn Leu Phe Ser  Val Asp His
    1130                1135                1140

Val Lys Asn Ile Glu Asn Leu  His Gly Ser Arg Leu  Asn Asp Arg
    1145                1150                1155

Ile Ala Gly Asp Asp Gln Asp  Asn Glu Leu Trp Gly  His Asp Gly
    1160                1165                1170

Asn Asp Thr Ile Arg Gly Arg  Gly Gly Asp Asp Ile  Leu Arg Gly
    1175                1180                1185

Gly Leu Gly Leu Asp Thr Leu  Tyr Gly Glu Asp Gly  Asn Asp Ile
    1190                1195                1200

Phe Leu Gln Asp Asp Glu Thr  Val Ser Asp Asp Ile  Asp Gly Gly
    1205                1210                1215
```

```
Ala Gly Leu Asp Thr Val Asp Tyr Ser Ala Met Ile His Pro Gly
1220                1225                1230

Arg Ile Val Ala Pro His Glu Tyr Gly Phe Gly Ile Glu Ala Asp
1235                1240                1245

Leu Ser Arg Glu Trp Val Arg Lys Ala Ser Ala Leu Gly Val Asp
1250                1255                1260

Tyr Tyr Asp Asn Val Arg Asn Val Glu Asn Val Ile Gly Thr Ser
1265                1270                1275

Met Lys Asp Val Leu Ile Gly Asp Ala Gln Ala Asn Thr Leu Met
1280                1285                1290

Gly Gln Gly Gly Asp Asp Thr Val Arg Gly Gly Asp Gly Asp Asp
1295                1300                1305

Leu Leu Phe Gly Gly Asp Gly Asn Asp Met Leu Tyr Gly Asp Ala
1310                1315                1320

Gly Asn Asp Thr Leu Tyr Gly Gly Leu Gly Asp Asp Thr Leu Glu
1325                1330                1335

Gly Gly Ala Gly Asn Asp Trp Phe Gly Gln Thr Gln Ala Arg Glu
1340                1345                1350

His Asp Val Leu Arg Gly Gly Asp Gly Val Asp Thr Val Asp Tyr
1355                1360                1365

Ser Gln Thr Gly Ala His Ala Gly Ile Ala Ala Gly Arg Ile Gly
1370                1375                1380

Leu Gly Ile Leu Ala Asp Leu Gly Ala Gly Arg Val Asp Lys Leu
1385                1390                1395

Gly Glu Ala Gly Ser Ser Ala Tyr Asp Thr Val Ser Gly Ile Glu
1400                1405                1410

Asn Val Val Gly Thr Glu Leu Ala Asp Arg Ile Thr Gly Asp Ala
1415                1420                1425

Gln Ala Asn Val Leu Arg Gly Ala Gly Gly Ala Asp Val Leu Ala
1430                1435                1440

Gly Gly Glu Gly Asp Asp Val Leu Leu Gly Gly Asp Gly Asp Asp
1445                1450                1455

Gln Leu Ser Gly Asp Ala Gly Arg Asp Arg Leu Tyr Gly Glu Ala
1460                1465                1470

Gly Asp Asp Trp Phe Phe Gln Asp Ala Ala Asn Ala Gly Asn Leu
1475                1480                1485

Leu Asp Gly Gly Asp Gly Arg Asp Thr Val Asp Phe Ser Gly Pro
1490                1495                1500

Gly Arg Gly Leu Asp Ala Gly Ala Lys Gly Val Phe Leu Ser Leu
1505                1510                1515

Gly Lys Gly Phe Ala Ser Leu Met Asp Glu Pro Glu Thr Ser Asn
1520                1525                1530

Val Leu Arg Asn Ile Glu Asn Ala Val Gly Ser Ala Arg Asp Asp
1535                1540                1545

Val Leu Ile Gly Asp Ala Gly Ala Asn Val Leu Asn Gly Leu Ala
1550                1555                1560

Gly Asn Asp Val Leu Ser Gly Gly Ala Gly Asp Asp Val Leu Leu
1565                1570                1575

Gly Asp Glu Gly Ser Asp Leu Leu Ser Gly Asp Ala Gly Asn Asp
1580                1585                1590

Asp Leu Phe Gly Gly Gln Asp Asp Thr Tyr Leu Phe Gly Val
1595                1600                1605

Gly Tyr Gly His Asp Thr Ile Tyr Glu Ser Gly Gly Gly His Asp
```

| | | | | | | | | | | |
|---|---|---|---|---|---|---|---|---|---|---|
| | | 1610 | | | 1615 | | | 1620 | | |
| Thr | Ile | Arg | Ile | Asn | Ala | Gly | Ala | Asp | Gln | Leu | Trp | Phe | Ala | Arg |
| | | 1625 | | | | 1630 | | | | 1635 | | | | |
| Gln | Gly | Asn | Asp | Leu | Glu | Ile | Arg | Ile | Leu | Gly | Thr | Asp | Asp | Ala |
| | | 1640 | | | | 1645 | | | | 1650 | | | | |
| Leu | Thr | Val | His | Asp | Trp | Tyr | Arg | Asp | Ala | Asp | His | Arg | Val | Glu |
| | | 1655 | | | | 1660 | | | | 1665 | | | | |
| Ile | Ile | His | Ala | Ala | Asn | Gln | Ala | Val | Asp | Gln | Ala | Gly | Ile | Glu |
| | | 1670 | | | | 1675 | | | | 1680 | | | | |
| Lys | Leu | Val | Glu | Ala | Met | Ala | Gln | Tyr | Pro | Asp | Pro | Gly | Ala | Ala |
| | | 1685 | | | | 1690 | | | | 1695 | | | | |
| Ala | Ala | Ala | Pro | Pro | Ala | Ala | Arg | Val | Pro | Asp | Thr | Leu | Met | Gln |
| | | 1700 | | | | 1705 | | | | 1710 | | | | |
| Ser | Leu | Ala | Val | Asn | Trp | Arg | | | | | | | | |
| | | 1715 | | | | 1720 | | | | | | | | |

```
<210> SEQ ID NO 5
<211> LENGTH: 8825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
cggaagagcg cccaatacgc aaaccgcctc tccccgcgcg ttggccgatt cattaatgca      60
gctggcacga caggtttccc gactggaaag cgggcagtga gcgcaacgca attaatgtga     120
gttagctcac tcattaggca ccccaggctt tacactttat gcttccggct cgtatgttgt     180
gtggaattgt gagcggataa caatttcaca caggaaacag ctatgaccat gattacgaat     240
ttaatacgac tcactatagg gaaagctcta gaataatttt gtttaacttt aagaaggag     300
atatacatat gcttccgtcc gcccaagcgc cctccctcct caatcccacc gacgacttcg     360
cggcactggg caatattgcc tggctgtgga tgaactctcc catgcaccgc gactggccgg     420
tgcatctgct cgcacgcaac acgctcgcgc gattcaact gggccaatac attctgctgc     480
gatgcaatga cgtgccggtt gcatactgca gctgggccct aatggacgcc gacaccgaac     540
tctcctatgt catggcgccc tcgtcgctgg gcgggaatgc ctggaactgc ggcgaccgac     600
tgtggatcat cgactggatc gcgccattct cgcgcgacga caatcgtgcg ctgcgccgcg     660
cgctggccga acggcacccc gacagcgtgg gccgttcgct gcgcgttcgg cgcggcggcg     720
acaccgcgcg cgtcaaggag taccgaggcc gcgcgctgga cgcggccgcc actcgcgcgc     780
agctggaccg ctaccatgcc gaactgatcg caggactgcg cgcgagcaac ggcggatacg     840
cgccgcgagg ccggggcacc gcctaaggat cctctagagc ttgcatgccc tggcacgaca     900
ggtttcccga ctgaaagcg gcagtgagc gcaacgcaat taatgtgagt tagctcactc     960
attaggcacc ccaggcttta cactttatgc ttccggctcg tatgttgtgt ggaattgtga    1020
gcggataaca atttcacaca ggaaacagct atgaccatgc agcaatcgca tcaggctggt    1080
tacgcaaacg ccgccgaccg ggagtctggc atccccgcag ccgtactcga tggcatcaag    1140
gccgtggcga aggaaaaaaa cgccacattg atgttccgcc tggtcaaccc ccattccacc    1200
agcctgattg ccgaaggggt ggccaccaaa ggattgggcg tgcacgccaa gtcgtccgat    1260
tgggggttgc aggcgggcta cattcccgtc aaccgaatc tttccaaact gttcggccgt    1320
gcgcccgagg tgatcgcgcg gccgacaac gacgtcaaca gcagcctggc gcatggccat    1380
```

```
accgcggtcg acctgacgct gtcgaaagag cggcttgact atctgcggca agcgggcctg    1440
gtcaccggca tggccgatgg cgtggtcgcg agcaaccacg caggctacga gcagttcgag    1500
tttcgcgtga aggaaacctc ggacgggcgc tatgccgtgc agtatcgccg caagggcggc    1560
gacgatttcg aggcggtcaa ggtgatcggc aatgccgccg gtattccact gacggcggat    1620
ggatccatcg acatgttcgc cattatgccg catctgtcca acttcgcga ctcggcgcgc     1680 agttcggtga ccagcggcga ttcggtgacc gattacctgg cgcgcacgcg gcgggccgcc    1740
agcgaggcca cgggcggtgt acacctggat cgcgaacgca tcgacttgtt gtggaaaatc    1800
gctcgcgccg cgcccgttc cgcagtgggc accgaggcgc gtcgccagtt ccgctacgac      1860
ggcgacatga atatcggcgt gatcaccgat ttcgagctgg aagtgcgcaa tgcgctgaac    1920
aggcgggcgc acgccgtcgg cgcgcaggac gtggtccagc atggcactga gcagaacaat    1980
cctttcccgg aggcagatga aagattttc gtcgtatcgg ccaccggtga agccagatg       2040 ctcacgcgcg gcaactgaa ggaatacatt ggccagcagc gcggcgaggg ctatgtcttc      2100
tacgagaacc gtgcatacgg cgtggcgggg aaaagcctgt tcgacgatgg gctgggagcc    2160
gcgcccggcg tgccgagcgg acgttcgaag ttctcgccgg atgtactgga aacggtgccg    2220
gcgtcacccg gattgcggcg gccgtcgctg ggcgcagtgg aacgccagga ttccggctat    2280
gacagccttg atggggtggg atcgcgatcg ttctcgttgg gcgaggtgtc cgacatggcc    2340
gccgtggaag cggcggaact ggaaatgacc cggcaagtct gcacgccgg ggcgcggcag     2400 gacgatgccg agccgggcgt gagcggtgcg tcggcgcact ggggggcagcg ggcgctgcag   2460 ggcgcccagg cggtggcggc ggcgcagcgg ctggttcatg ccattgccct gatgacgcaa    2520
ttcggccggg ccggttccac caacacgccg caggaagcgg cctcgttgtc ggcggccgtg    2580
ttcggcttgg gcgaggccag cagcgccgtg gccgaaaccg tgagcggttt tttccgcggg    2640
tcttcgcgct gggccggcgg tttcggcgtg gctggcggcg cgatggcgct gggaggcggc    2700
atcgccgcgg ccgttggcgc cgggatgtcg ttgaccgatg acgcgccggc cggacagaag    2760
gccgccgccg gagctccgat cgcgctgcag ttaacgggtg gaacggtcga gctggcttct    2820
tccatcgcgt tggcgctggc cgcggcgcgc ggcgtgacca gcggcttgca ggtggccggg    2880
gcgtcggccg gggcggctgc cggcgcattg gccgcggcgc tcagtcccat ggagatctac    2940
ggcctggtgc agcaatcgca ctatgcggat cagctggaca gctggcgca ggaatcgagc     3000 gcatacggtt acgagggcga cgccttgctg gcccagctgt atcgcgacaa gacggccgcc    3060
gagggcgccg tcgccggcgt ctccgccgtc ctgagcacgg tggggcggc ggtgtcgatc     3120 gccgcggcgg ccagcgtggt aggggccccg gtggcggtgg tcacttcctt gctgaccggg    3180
gctctcaacg gcatcctgcg cggcgtgcag cagcccatca tcgaaaagct ggccaacgat    3240
tacgctcgca agatcgacga gctgggcggg ccgcaagcgt acttcgagaa aaacctgcag    3300
gcgcgtcacg aacaactggc caattcggac ggcctacgga aaatgctggc cgacctgcag    3360
gccggttgga acgccagcag cgtgatcggg gtgcagacga cagagatctc caagtcggcg    3420
ctcgaactgg ccgccattac cggcaacgcg acaacctga atccgtcga cgtgttcgtg      3480 gaccgcttcg tccagggcga gcgggtgcc ggccagccgg tggtcctcga cgtcgccgcc     3540
ggcggcatcg atatcgccag ccgcaagggc gagcggccgg cgctgacgtt catcacgccg    3600
ctggccgcgc caggagaaga gcagcgccgg cgcacgaaaa cgggcagatc tgaattcacc    3660
acattcgtcg agatcgtggg caagcaggac cgctggcgca tccgggacgg cgcggccgac    3720
```

```
accaccatcg atctggccaa ggtggtgtcg caactggtcg acgccaatgg cgtgctcaag    3780
cacagcatca aactggatgt gatcggcgga gatggcgatg acgtcgtgct tgccaatgct    3840
tcgcgcatcc attatgacgg cggcgcgggc accaacacgg tcagctatgc cgccctgggt    3900
cgacaggatt ccattaccgt gtccgccgac ggggaacgtt tcaacgtgcg caagcagttg    3960
aacaacgcca acgtgtatcg cgaaggcgtg gctacccaga caaccgccta cggcaagcgc    4020
acggagaatg tccaataccg ccatgtcgag ctggcccgtg tcgggcaagt ggtggaggtc    4080
gacacgctcg agcatgtgca gcacatcatc ggcggggccg gcaacgattc gatcaccggc    4140
aatgcgcacg acaacttcct agccggcggg tcgggcgacg acaggctgga tggcggcgcc    4200
ggcaacgaca ccctggttgg cggcgagggc caaaacacgg tcatcggcgg cgccggcgac    4260
gacgtattcc tgcaggacct gggggtatgg agcaaccagc tcgatggcgg cgcgggcgtc    4320
gataccgtga agtacaacgt gcaccagcct tccgaggagc gcctcgaacg catgggcgac    4380
acgggcatcc atgccgatct tcaaaagggc acggtcgaga agtggccggc cctgaacctg    4440
ttcagcgtcg accatgtcaa gaatatcgag aatctgcacg gctcccgcct aaacgaccgc    4500
atcgccggcg acgaccagga caacgagctc tggggccacg atggcaacga cacgatacgc    4560
ggccggggcg gcgacgacat cctgcgcggc ggcctgggcc tggacacgct gtatggcgag    4620
gacggcaacg acatcttcct gcaggacgac gagaccgtca gcgatgacat cgacggcggc    4680
gcggggctgg acaccgtcga ctactccgcc atgatccatc caggcaggat cgttgcgccg    4740
catgaatacg gcttcgggat cgaggcggac ctgtccaggg aatgggtgcg caaggcgtcc    4800
gcgctgggcg tggactatta cgataatgtc cgcaatgtcg aaaacgtcat cggtacgagc    4860
atgaaggatg tgctcatcgg cgacgcgcaa gccaataccc tgatgggcca gggcggcgac    4920
gataccgtgc gcgcggcgga cggcgatgat ctgctgttcg gcggcgacgg caacgacatg    4980
ctgtatggcg acgccggcaa cgacaccctc tacgggggc tgggcgacga taccctttgaa    5040 ggcggcgcgg gcaacgattg gttcggccag acgcaggcgc gcgagcatga cgtgctgcgc    5100
ggcggagatg gggtggatac cgtcgattac agccagaccg gcgcgcatgc cggcattgcc    5160
gcgggtcgca tcgggctggg catcctggct gacctgggcg ccggccgcgt cgacaagctg    5220
ggcgaggccg gcagcagcgc ctacgatacg gtttccggta tcgagaacgt ggtgggcacg    5280
gaactggccg accgcatcac gggcgatgcg caggccaacg tgctgcgcgg cgcgggtggc    5340
gccgacgtgc ttgcgggcgg cgagggcgac gatgtgctgc tgggcggcga cggcgacgac    5400
cagctgtcgg gcgacgccgg acgcgatcgc ttgtacggcg aagccggtga cgactggttc    5460
ttccaggatg ccgccaatgc cggcaatctg ctcgacggcg gcgacggccg cgataccgtg    5520
gatttcagcg gcccgggccg gggcctcgac gccggcgcaa agggcgtatt cctgagcttg    5580 ggcaagggt tcgccagcct gatggacgaa cccgaaacca gcaacgtgtt gcgcaatatc    5640
gagaacgccg tgggcagcgc gcgtgatgac gtgctgatcg gcgacgcagg cgccaacgtc    5700
ctcaatggcc tggcgggcaa cgacgtgctg tccggcggcg ctggcgacga tgtgctgctg    5760
ggcgacgagg gctcggacct gctcagcggc gatgcgggca acgacgatct gttcggcggg    5820
cagggcgatg atacttatct gttcggggtc gggtacgggc acgacacgat ctacgaatcg    5880
ggcggcggcc atgacaccat ccgcatcaac gcggggcgg accagctgtg gttcgcgcgc    5940
cagggcaacg acctggagat ccgcattctc ggcaccgacg atgcacttac cgtgcacgac    6000
tggtatcgcg acgccgatca ccgggtggaa atcatccatg ccgccaacca ggcggtagac    6060 cagggcaggca tcgaaaagct ggtcgaggca atggcgcagt atccggaccc cggcgcggcg    6120
```

```
gcggctgccc cgccggcggc gcgcgtgccg gacacgctga tgcagtccct ggctgtcaac    6180
tggcgctgaa gcgccgtgaa tcacggcccg cctgcctcgc gcggcggcgc cgtctctttg    6240
cgttcttctc cgaggtattt cccatcatga attcactggc cgtcgtttta caacgtcgtg    6300
actgggaaaa ccctggcgtt acccaactta atcgccttgc agcacatccc cctttcgcca    6360
gctggcgtaa tagcgaagag gcccgcaccg atcgcccttc ccaacagttg cgcagcctga    6420
atggcgaatg ggaaattgta aacgttaata ttttgttaat attttgttaa aattcgcgtt    6480
aaatttttgt taaatcagct cattttttaa ccaataggcc gaaatcggca aaatccctta    6540
taaatcaaaa gaatagaccg agatagggtt gagtgttgtt ccagtttgga acaagagtcc    6600
actattaaag aacgtggact ccaacgtcaa agggcgaaaa accgtctatc agggcgatgg    6660
cccactacgt gaaccatcac cctaatcaag ttttttgggg tcgaggtgcc gtaaagcact    6720
aaatcggaac cctaaaggga tgccccgatt tagagcttga cggggaaagc cggcgaacgt    6780
ggcgagaaag gaagggaaga agcgaaagg agcgggcgct agggcgctgg caagtgtagc    6840
ggtcacgctg cgcgtaacca ccacacccgc cgcgcttaat gcgccgctac agggcgcgtc    6900
aggtggcact tttcggggaa atgtgcgcgg aacccctatt tgtttatttt tctaaataca    6960
ttcaaatatg tatccgctca tgagacaata accctgataa atgcttcaat aatattgaaa    7020
aaggaagagt atgagtattc aacatttccg tgtcgccctt attcccttt ttgcggcatt    7080 ttgccttcct gttttgctc acccagaaac gctggtgaaa gtaaaagatg ctgaagatca    7140
gttgggtgca cgagtgggtt acatcgaact ggatctcaac agcggtaaga tccttgagag    7200
ttttcgcccc gaagaacgtt ttccaatgat gagcactttt aaagttctgc tatgtggcgc    7260
ggtattatcc cgtattgacg ccgggcaaga gcaactcggt cgccgcatac actattctca    7320
gaatgacttg gttgagtact caccagtcac agaaaagcat cttacggatg gcatgacagt    7380
aagagaatta tgcagtgctg ccataaccat gagtgataac actgcggcca acttacttct    7440
gacaacgatc ggaggaccga aggagctaac cgcttttttg cacaacatgg ggatcatgt    7500 aactcgcctt gatcgttggg aaccggagct gaatgaagcc ataccaaacg acgagcgtga    7560
caccacgatg cctgtagcaa tggcaacaac gttgcgcaaa ctattaactg gcgaactact    7620
tactctagct tcccggcaac aattaataga ctggatggag gcggataaag ttgcaggacc    7680
acttctgcgc tcggcccttc cggctggctg gtttattgct gataaatctg gagccggtga    7740
gcgtgggtct cgcggtatca ttgcagcact ggggccagat ggtaagccct cccgtatcgt    7800
agttatctac acgacgggga gtcaggcaac tatggatgaa cgaaatagac agatcgctga    7860
gataggtgcc tcactgatta agcattggta actgtcagac caagtttact catatatact    7920
ttagattgat ttaaaacttc attttttaatt taaaaggatc taggtgaaga tccttttga    7980 taatctcatg accaaaatcc cttaacgtga gttttcgttc cactgagcgt cagaccccgt    8040
agaaaagatc aaaggatctt cttgagatcc tttttttctg cgcgtaatct gctgcttgca    8100
aacaaaaaaa ccaccgctac cagcggtggt ttgtttgccg gatcaagagc taccaactct    8160
ttttccgaag gtaactggct tcagcagagc gcagatacca atactgtcc ttctagtgta    8220 gccgtagtta ggccaccact tcaagaactc tgtagcaccg cctacatacc tcgctctgct    8280
aatcctgtta ccagtggctg ctgccagtgg cgataagtcg tgtcttaccg ggttggactc    8340
aagacgatag ttaccggata aggcgcagcg gtcgggctga acggggggtt cgtgcacaca    8400
gcccagcttg gagcgaacga cctacaccga actgagatac ctacagcgtg agctatgaga    8460
```

```
aagcgccacg cttcccgaag ggagaaaggc ggacaggtat ccggtaagcg gcagggtcgg    8520
aacaggagag cgcacgaggg agcttccagg gggaaacgcc tggtatcttt atagtcctgt    8580
cgggtttcgc cacctctgac ttgagcgtcg attttgtga tgctcgtcag gggggcggag    8640
cctatggaaa aacgccagca acgcggcctt tttacggttc ctggccttt gctggccttt    8700 tgctcacatg ttctttcctg cgttatcccc tgattctgtg ataaccgta ttaccgcctt    8760 tgagtgagct gataccgctc gccgcagccg aacgaccgag cgcagcgagt cagtgagcga    8820
ggaag                                                                8825

<210> SEQ ID NO 6
<211> LENGTH: 8855
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
cggaagagcg cccaatacgc aaaccgcctc tccccgcgcg ttggccgatt cattaatgca      60
gctggcacga caggtttccc gactggaaag cgggcagtga gcgcaacgca attaatgtga     120
gttagctcac tcattaggca ccccaggctt tacactttat gcttccggct cgtatgttgt     180
gtggaattgt gagcggataa caatttcaca caggaaacag ctatgaccat gattacgaat     240
ttaatacgac tcactatagg gaaagctcta gaataattt tgtttaactt taagaaggag     300
atatacatat gcttccgtcc gcccaagcgc cctccctcct caatcccacc gacgacttcg     360
cggcactggg caatattgcc tggctgtgga tgaactctcc catgcaccgc gactggccgg     420
tgcatctgct cgcacgcaac acgctcgcgc gattcaact gggccaatac attctgctgc     480
gatgcaatga cgtgccggtt gcatactgca gctgggccct aatggacgcc gacaccgaac     540
tctcctatgt catggcgccc tcgtcgctgg gcgggaatgc ctggaactgc ggcgaccgac     600
tgtggatcat cgactggatc gcgccattct cgcgcgacga caatcgtgcg ctgcgccgcg     660
cgctggccga acggcacccc gacagcgtgg gccgttcgct gcgcgttcgg cgcggcggcg     720
acaccgcgcg cgtcaaggag taccgaggcc gcgcgctgga cgcggccgcc actcgcgcgc     780
agctggaccg ctaccatgcc gaactgatcg caggactgcg cgcgagcaac ggcggatacg     840
cgccgcgagg ccggggcacc gcctaaggat cctctagagc ttgcatgccc tggcacgaca     900
ggtttcccga ctggaaagcg gcagtgagc gcaacgcaat taatgtgagt tagctcactc     960
attaggcacc ccaggcttta cactttatgc ttccggctcg tatgttgtgt ggaattgtga    1020
gcggataaca atttcacaca ggaaacagct atgaccatgc agcaatcgca tcaggctggt    1080
tacgcaaacg ccgccgaccg ggagtctggc atccccgcag ccgtactcga tggcatcaag    1140
gccgtggcga aggaaaaaaa cgccacattg atgttccgcc tggtcaaccc ccattccacc    1200
agcctgattg ccgaagggt ggccaccaaa ggattgggcg tgcacgccaa gtcgtccgat    1260
tgggggttgc aggcgggcta cattcccgtc aacccgaatc tttccaaact gttcggccgt    1320
gcgcccgagg tgatcgcgcg ggccgacaac gacgtcaaca gcagcctggc gcatggccat    1380
accgcggtcg acctgacgct gtcgaaagag cggcttgact atctgcggca agcgggcctg    1440
gtcaccggca tggccgatgg cgtggtcgcg agcaaccacg caggctacga gcagttcgag    1500
tttcgcgtga aggaaacctc ggacgggcgc tatgccgtgc agtatcgccg caagggcggc    1560
gacgatttcg aggcggtcaa ggtgatcggc aatgccgccg gtattccact gacggcggat    1620
```

```
ggatccatcg acatgttcgc cattatgccg catctgtcca acttccgcga ctcggcgcgc    1680
agttcggtga ccagcggcga ttcggtgacc gattacctgg cgcgcacgcg gcgggccgcc    1740
agcgaggcca cgggcggtgt actctcaata attaatttcg aaaagcttgt acacctggat    1800
cgcgaacgca tcgacttgtt gtggaaaatc gctcgcgccg gcgcccgttc cgcagtgggc    1860
accgaggcgc gtcgccagtt ccgctacgac ggcgacatga atatcggcgt gatcaccgat    1920
ttcgagctgg aagtgcgcaa tgcgctgaac aggcgggcgc acgccgtcgg cgcgcaggac    1980
gtggtccagc atggcactga gcagaacaat cctttcccgg aggcagatga aagattttc    2040
gtcgtatcgg ccaccggtga aagccagatg ctcacgcgcg ggcaactgaa ggaatacatt    2100
ggccagcagc gcggcgaggg ctatgtcttc tacgagaacc gtgcatacgg cgtggcgggg    2160
aaaagcctgt tcgacgatgg gctgggagcc gcgcccggcg tgccgagcgg acgttcgaag    2220
ttctcgccgg atgtactgga aacggtgccg gcgtcacccg gattgcggcg gccgtcgctg    2280
ggcgcagtgg aacgccagga ttccggctat gacagccttg atgggtggg atcgcgatcg    2340
ttctcgttgg gcgaggtgtc cgacatgccc gccgtggaag cggcggaact ggaaatgacc    2400
cggcaagtct tgcacgccgg ggcgcggcag gacgatgccg agccgggcgt gagcggtgcg    2460
tcggcgcact gggggcagcg ggcgctgcag ggcgcccagg cggtggcggc ggcgcagcgg    2520
ctggttcatg ccattgccct gatgacgcaa ttcggccggg ccggttccac caacacgccg    2580
caggaagcgg cctcgttgtc ggcggccgtg ttcggcttgg gcgaggccag cagcgccgtg    2640
gccgaaaccg tgagcggttt tttccgcggg tcttcgcgct gggccggcgg tttcggcgtg    2700
gctggcggcg cgatgcgct gggaggcggc atcgccgcgg ccgttggcgc cgggatgtcg    2760
ttgaccgatg acgcgccggc cggacagaag gccgccgccg gagctccgat cgcgctgcag    2820
ttaacgggtg gaacggtcga gctggcttct tccatcgcgt tggcgctggc cgcggcgcgc    2880
ggcgtgacca gcggcttgca ggtggccggg gcgtcggccg gggcggctgc cggcgcattg    2940
gccgcggcgc tcagtcccat ggagatctac ggcctggtgc agcaatcgca ctatgcggat    3000
cagctggaca agctggcgca ggaatcgagc gcatacggtt acgagggcga cgccttgctg    3060
gcccagctgt atcgcgacaa gacggccgcc gagggcgccg tcgccggcgt ctccgccgtc    3120
ctgagcacgg tgggggcggc ggtgtcgatc gccgcggcgg ccagcgtggt aggggccccg    3180
gtggcggtgg tcacttcctt gctgaccggg gctctcaacg gcatcctgcg cggcgtgcag    3240
cagcccatca tcgaaaagct ggccaacgat tacgctcgca agatcgacga gctgggcggg    3300
ccgcaagcgt acttcgagaa aaacctgcag gcgcgtcacg aacaactggc caattcggac    3360
ggcctacgga aaatgctggc cgacctgcag gccggttgga acgccagcag cgtgatcggg    3420
gtgcagacga cagagatctc caagtcggcg ctcgaactgg ccgccattac cggcaacgcg    3480
gacaacctga atccgtcga cgtgttcgtg gaccgcttcg tccagggcga gcgggtggcc    3540
ggccagccgg tggtcctcga cgtcgccgcc ggcggcatcg atatcgccag ccgcaagggc    3600
gagcggccgg cgctgacgtt catcacgccg ctggccgcgc aggagaaga gcagcgccgg    3660
cgcacgaaaa cggcagatc tgaattcacc acattcgtcg agatcgtggg caagcaggac    3720
cgctggcgca tccggacgg cgcggccgac accaccatca atctggccaa ggtggtgtcg    3780
caactggtcg acgccaatgg cgtgctcaag cacagcatca aactggatgt gatcggcgga    3840
gatggcgatg acgtcgtgct tgccaatgct tcgcgcatcc attatgacgg cggcgcgggc    3900
accaacacgg tcagctatgc cgccctgggt cgacaggatt ccattaccgt gtccgccgac    3960
ggggaacgtt tcaacgtgcg caagcagttg aacaacgcca acgtgtatcg cgaaggcgtg    4020
```

```
gctacccaga caaccgccta cggcaagcgc acggagaatg tccaataccg ccatgtcgag    4080
ctggcccgtg tcgggcaagt ggtggaggtc gacacgctcg agcatgtgca gcacatcatc    4140
ggcggggccg gcaacgattc gatcaccggc aatgcgcacg acaacttcct agccggcggg    4200
tcgggcgacg acaggctgga tggcggcgcc ggcaacgaca ccctggttgg cggcgagggc    4260
caaaacacgg tcatcggcgg cgccggcgac gacgtattcc tgcaggacct ggggg tatgg    4320
agcaaccagc tcgatggcgg cgcgggcgtc gataccgtga agtacaacgt gcaccagcct    4380
tccgaggagc gcctcgaacg catgggcgac acgggcatcc atgccgatct caaaagggc    4440
acggtcgaga agtggccggc cctgaacctg ttcagcgtcg accatgtcaa gaatatcgag    4500
aatctgcacg gctcccgcct aaacgaccgc atcgccggcg acgaccagga caacgagctc    4560
tggggccacg atggcaacga cacgatacgg ggcgggggcg gcgacgacat cctgcgcggc    4620
ggcctgggcc tggacacgct gtatggcgag gacggcaacg acatcttcct gcaggacgac    4680
gagaccgtca gcgatgacat cgacggcggc gcggggctgg acaccgtcga ctactccgcc    4740
atgatccatc caggcaggat cgttgcgccg catgaatacg gcttcgggat cgaggcggac    4800
ctgtccaggg aatgggtgcg caaggcgtcc gcgctgggcg tggactatta cgataatgtc    4860
cgcaatgtcg aaaacgtcat cggtacgagc atgaaggatg tgctcatcgg cgacgcgcaa    4920
gccaataccc tgatgggcca gggcggcgac gataccgtgc gcggcggcga cggcgatgat    4980
ctgctgttcg gcggcgacgg caacgacatg ctgtatggcg acgccggcaa cgacaccctc    5040
tacggggggc tggcgacga taccc ttgaa ggcggcgcgg gcaacgattg gttcggccag    5100
acgcaggcgc gcgagcatga cgtgctgcgc ggcggagatg gggtggatac cgtcgattac    5160
agccagaccg cgcgcatgc cggcattgcc gcgggtcgca tcgggctggg catcctggct    5220
gacctgggcg ccggccgcgt cgacaagctg ggcgaggccg gcagcagcgc ctacgatacg    5280
gtttccggta tcgagaacgt ggtgggcacg gaactggccg accgcatcac gggcgatgcg    5340
caggccaacg tgctgcgcgg cgcgggtggc gccgacgtgc ttgcgggcgg cgagggcgac    5400
gatgtgctgc tggcggcga cggcgacgac cagctgtcgg gcgacgccgg acgcgatcgc    5460
ttgtacggcg aagccggtga cgactggttc ttccaggatg ccgccaatgc cggcaatctg    5520
ctcgacggcg cgacggccg cgataccgtg gatttcagcg gcccgggccg gggcctcgac    5580
gccggcgcaa agggcgtatt cctgagcttg gcaagggt tcgccagcct gatggacgaa    5640
cccgaaacca gcaacgtgtt gcgcaatatc gagaacgccg tgggcagcgc gcgtgatgac    5700
gtgctgatcg gcgacgcagg cgccaacgtc tcaatggcc tggcgggcaa cgacgtgctg    5760
tccggcggcg ctggcgacga tgtgctgctg ggcgacgagg ctcggacct gctcagcggc    5820
gatgcgggca acgacgatct gttcggcggg cagggcgatg atacttatct gttcggggtc    5880
gggtacgggc acgacacgat ctacgaatcg ggcggcggcc atgacaccat ccgcatcaac    5940
gcggggcgg accagctgtg gttcgcgcgc agggcaacg acctggagat ccgcattctc    6000
ggcaccgacg atgcacttac cgtgcacgac tggtatcgcg acgccgatca ccgggtggaa    6060
atcatccatg ccgccaacca ggcggtagac caggcaggca tcgaaaagct ggtcgaggca    6120
atggcgcagt atccggaccc cggcgcgcg gcggctgccc cgccggcggc gcgcgtgccg    6180
gacacgctga tgcagtccct ggctgtcaac tggcgctgaa gcgccgtgaa tcacggcccg    6240
cctgcctcgc gcggcggcgc cgtctctttg cgttcttctc cgaggtatt tccatcatga    6300
attcactggc cgtcgtttta caacgtcgtg actgggaaaa ccctggcgtt acccaactta    6360
```

```
atcgccttgc agcacatccc cctttcgcca gctggcgtaa tagcgaagag gcccgcaccg    6420
atcgcccttc ccaacagttg cgcagcctga atggcgaatg ggaaattgta acgttaata     6480 ttttgttaat attttgttaa aattcgcgtt aaattttgt taaatcagct cattttttaa     6540
ccaataggcc gaaatcggca aaatcccta taaatcaaaa gaatagaccg atatagggtt     6600
gagtgttgtt ccagtttgga acaagagtcc actattaaag aacgtggact ccaacgtcaa    6660
agggcgaaaa accgtctatc agggcgatgg cccactacgt gaaccatcac cctaatcaag    6720 tttttttgggg tcgaggtgcc gtaaagcact aaatcggaac cctaagggga tgccccgatt   6780
tagagcttga cggggaaagc cggcgaacgt ggcgagaaag gaagggaaga agcgaaagg     6840 agcgggcgct agggcgctgg caagtgtagc ggtcacgctg cgcgtaacca ccacacccgc    6900
cgcgcttaat gcgccgctac agggcgcgtc aggtggcact tttcggggaa atgtgcgcgg    6960 aaccccctatt tgtttatttt tctaaataca ttcaaatatg tatccgctca tgagacaata   7020
accctgataa atgcttcaat aatattgaaa aggaagagt atgagtattc aacatttccg     7080
tgtcgccctt attcccttt ttgcggcatt ttgccttcct gtttttgctc acccagaaac     7140
gctggtgaaa gtaaaagatg ctgaagatca gttgggtgca cgagtgggtt acatcgaact    7200
ggatctcaac agcggtaaga tccttgagag ttttcgcccc gaagaacgtt ttccaatgat    7260
gagcactttt aaagttctgc tatgtggcgc ggtattatcc cgtattgacg ccgggcaaga    7320
gcaactcggt cgccgcatac actattctca gaatgacttg gttgagtact caccagtcac    7380
agaaaagcat cttacggatg gcatgacagt aagagaatta tgcagtgctg ccataaccat    7440
gagtgataac actgcggcca acttacttct gacaacgatc ggaggaccga aggagctaac    7500
cgcttttttg cacaacatgg ggatcatgt aactcgcctt gatcgttggg aaccggagct    7560
gaatgaagcc ataccaaacg acgagcgtga ccaccacgat cctgtagcaa tggcaacaac    7620
gttgcgcaaa ctattaactg gcgaactact tactctagct tcccggcaac aattaataga    7680
ctggatggag gcggataaag ttgcaggacc acttctgcgc tcggcccttc cggctggctg    7740
gtttattgct gataaatctg gagccggtga gcgtgggtct cgcggtatca ttgcagcact    7800
ggggccagat ggtaagccct cccgtatcgt agttatctac acgacgggga gtcaggcaac    7860
tatggatgaa cgaaatagac agatcgctga gataggtgcc tcactgatta agcattggta    7920
actgtcagac caagtttact catatatact ttagattgat ttaaaacttc atttttaatt    7980
taaaaggatc taggtgaaga tccttttga taatctcatg accaaaatcc cttaacgtga    8040
gttttcgttc cactgagcgt cagacccgt agaaaagatc aaaggatctt cttgagatcc     8100
ttttttcctg cgcgtaatct gctgcttgca acaaaaaaa ccaccgctac cagcggtggt    8160
ttgtttgccg gatcaagagc taccaactct ttttccgaag gtaactggct tcagcagagc    8220
gcagatacca atactgtcc ttctagtgta gccgtagtta ggccaccact tcaagaactc     8280
tgtagcaccg cctacatacc tcgctctgct aatcctgtta ccagtggctg ctgccagtgg    8340
cgataagtcg tgtcttaccg ggttggactc aagacgatag ttaccggata aggcgcagcg    8400
gtcgggctga acggggggtt cgtgcacaca gcccagcttg gagcgaacga cctacaccga    8460
actgagatac ctacagcgtg agctatgaga aagcgccacg cttcccgaag ggagaaaggc    8520
ggacaggtat ccggtaagcg cagggtcgg aacaggagag cgcacgaggg agcttccagg    8580
gggaaacgcc tggtatcttt atagtcctgt cgggtttcgc cacctctgac ttgagcgtcg    8640 attttttgtga tgctcgtcag gggggcggag cctatggaaa aacgccagca acgcggcctt   8700
tttacggttc ctggcctttt gctggccttt tgctcacatg ttctttcctg cgttatcccc    8760
```

-continued

```
tgattctgtg gataaccgta ttaccgcctt tgagtgagct gataccgctc gccgcagccg    8820
aacgaccgag cgcagcgagt cagtgagcga ggaag                              8855
```

<210> SEQ ID NO 7
<211> LENGTH: 1706
<212> TYPE: PRT
<213> ORGANISM: Bordetella parapertussis

<400> SEQUENCE: 7

```
Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350
```

```
Ala Gly Lys Ser Leu Phe Asp Asp Gly Leu Gly Ala Ala Pro Gly Val
            355                 360                 365
Pro Gly Gly Arg Ser Lys Ser Ser Pro Asp Val Leu Glu Thr Val Pro
        370                 375                 380
Ala Ser Pro Gly Leu Arg Arg Pro Ser Leu Gly Ala Val Glu Arg Gln
385                 390                 395                 400
Asp Ser Gly Tyr Asp Ser Leu Asp Gly Val Gly Ser Arg Ser Phe Ser
                405                 410                 415
Leu Gly Glu Val Ser Asp Met Ala Ala Val Glu Ala Ala Leu Glu
            420                 425                 430
Met Thr Arg Gln Val Leu His Ala Gly Ala Arg Gln Asp Asp Ala Glu
        435                 440                 445
Pro Gly Val Ser Gly Ala Ser Ala His Trp Gly Gln Arg Ala Leu Gln
    450                 455                 460
Gly Ala Gln Ala Val Ala Ala Gln Arg Leu Val His Ala Ile Ala
465                 470                 475                 480
Leu Met Thr Gln Phe Gly Arg Ala Gly Ser Thr Asn Thr Pro Gln Glu
                485                 490                 495
Ala Ala Ser Leu Ser Ala Ala Val Phe Gly Leu Gly Glu Ala Ser Ser
            500                 505                 510
Ala Val Ala Glu Thr Val Ser Gly Phe Phe Arg Gly Ser Ser Arg Trp
        515                 520                 525
Ala Gly Gly Phe Gly Val Ala Gly Gly Ala Met Ala Leu Gly Gly Gly
    530                 535                 540
Ile Ala Ala Ala Val Gly Ala Gly Met Ser Leu Thr Asp Asp Ala Pro
545                 550                 555                 560
Ala Gly Gln Lys Ala Ala Val Gly Ala Glu Ile Ala Leu Gln Leu Thr
                565                 570                 575
Gly Gly Thr Val Glu Leu Ala Ser Ser Ile Ala Leu Ala Leu Ala Ala
            580                 585                 590
Ala Arg Gly Val Thr Ser Gly Leu Gln Val Ala Gly Ala Ser Ala Gly
        595                 600                 605
Ala Ala Ala Gly Ala Leu Ala Ala Ala Leu Ser Pro Met Glu Ile Tyr
    610                 615                 620
Gly Leu Val Gln Gln Ser His Tyr Ala Asp Gln Leu Asp Lys Leu Ala
625                 630                 635                 640
Gln Glu Ser Ser Ala Tyr Gly Tyr Glu Gly Asp Ala Leu Leu Ala Gln
                645                 650                 655
Leu Tyr Arg Asp Lys Thr Ala Ala Glu Gly Ala Val Ala Gly Val Ser
            660                 665                 670
Ala Val Leu Ser Thr Val Gly Ala Ala Val Ser Ile Ala Ala Ala Ala
        675                 680                 685
Ser Val Val Gly Ala Pro Val Ala Val Thr Ser Leu Leu Thr Gly
    690                 695                 700
Ala Leu Asn Gly Ile Leu Arg Gly Val Gln Gln Pro Ile Ile Glu Lys
705                 710                 715                 720
Leu Ala Asn Asp Tyr Ala Arg Lys Ile Asp Glu Leu Gly Gly Pro Gln
                725                 730                 735
Ala Tyr Phe Glu Lys Asn Leu Gln Ala Arg His Glu Gln Leu Ala Asn
            740                 745                 750
Ser Asp Gly Leu Arg Lys Met Leu Ala Asp Leu Gln Ala Gly Trp Asn
        755                 760                 765
Ala Ser Ser Val Ile Gly Val Gln Thr Thr Glu Ile Ser Lys Ser Ala
```

-continued

```
                770             775             780
Leu Glu Leu Ala Ala Ile Thr Gly Asn Ala Asp Asn Leu Lys Ser Ala
785                 790                 795                 800

Asp Val Phe Val Asp Arg Phe Ile Gln Gly Glu Arg Val Ala Gly Gln
                805                 810                 815

Pro Val Val Leu Asp Val Ala Ala Gly Ile Asp Ile Ala Ser Arg
                820                 825                 830

Lys Gly Glu Arg Pro Ala Leu Thr Phe Ile Thr Pro Leu Ala Ala Pro
                835                 840                 845

Gly Glu Glu Gln Arg Arg Thr Lys Thr Gly Lys Ser Glu Phe Thr
        850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
                885                 890                 895

Val Asp Ala Asn Gly Val Leu Lys His Ser Ile Lys Leu Glu Val Ile
                900                 905                 910

Gly Gly Asp Gly Asp Asp Val Val Leu Ala Asn Ala Ser Arg Ile His
        915                 920                 925

Tyr Asp Gly Gly Ala Gly Thr Asn Thr Val Ser Tyr Ala Ala Leu Gly
        930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Lys Thr Ala Tyr Gly Lys Arg Thr Glu Asn Val Gln Tyr Arg His
                980                 985                 990

Val Glu Leu Ala Arg Val Gly Gln  Leu Val Glu Val Asp  Thr Leu Glu
                995                 1000                1005

His Val  Gln His Ile Ile Gly  Gly Ala Gly Asn Asp  Ser Ile Thr
        1010                1015                1020

Gly Asn  Ala His Asp Asn Phe  Leu Ala Gly Gly Ala  Gly Asp Asp
        1025                1030                1035

Arg Leu  Asp Gly Gly Ala Gly  Asn Asp Thr Leu Val  Gly Gly Glu
        1040                1045                1050

Gly His  Asn Thr Val Val Gly  Gly Ala Gly Asp Asp  Val Phe Leu
        1055                1060                1065

Gln Asp  Leu Gly Val Trp Ser  Asn Gln Leu Asp Gly  Gly Ala Gly
        1070                1075                1080

Val Asp  Thr Val Lys Tyr Asn  Val His Gln Pro Ser  Glu Glu Arg
        1085                1090                1095

Leu Glu  Arg Met Gly Asp Thr  Gly Ile His Ala Asp  Leu Gln Lys
        1100                1105                1110

Gly Thr  Val Glu Lys Trp Pro  Ala Leu Asn Leu Phe  Ser Val Asp
        1115                1120                1125

His Val  Lys Asn Ile Glu Asn  Leu His Gly Ser Ser  Leu Asn Asp
        1130                1135                1140

Ser Ile  Ala Gly Asp Asp Arg  Asp Asn Glu Leu Trp  Gly Asp Asp
        1145                1150                1155

Gly Asn  Asp Thr Ile His Gly  Arg Gly Gly Asp Asp  Ile Leu Arg
        1160                1165                1170

Gly Gly  Leu Gly Leu Asp Thr  Leu Tyr Gly Glu Asp  Gly Asn Asp
        1175                1180                1185
```

```
Ile Phe Leu Gln Asp Asp Glu Thr Val Ser Asp Asp Ile Asp Gly
1190                1195                1200

Gly Ala Gly Leu Asp Thr Val Asp Tyr Ser Ala Met Ile His Ala
1205                1210                1215

Gly Lys Ile Val Ala Pro His Glu Tyr Gly Phe Gly Ile Glu Ala
1220                1225                1230

Asp Leu Ser Glu Gly Trp Val Arg Lys Ala Ala Arg Arg Gly Met
1235                1240                1245

Gly Tyr Tyr Asp Ser Val Arg Ser Val Glu Asn Val Ile Gly Thr
1250                1255                1260

Ser Met Lys Asp Val Leu Ile Gly Asp Ala Gln Ala Asn Thr Leu
1265                1270                1275

Met Gly Gln Gly Gly Asp Thr Val Arg Gly Gly Asp Gly Asp
1280                1285                1290

Asp Leu Leu Phe Gly Gly Asp Gly Asn Asp Met Leu Tyr Gly Asp
1295                1300                1305

Ala Gly Asn Asp Thr Leu Tyr Gly Gly Leu Gly Asp Asp Thr Leu
1310                1315                1320

Glu Gly Gly Ala Gly Asn Asp Trp Phe Gly Gln Thr Pro Ala Arg
1325                1330                1335

Glu His Asp Val Leu Arg Gly Gly Ala Gly Val Asp Thr Val Asp
1340                1345                1350

Tyr Ser Gln Ala Gly Ala His Ala Gly Val Ala Thr Gly Arg Ile
1355                1360                1365

Gly Leu Gly Ile Leu Ala Asp Leu Gly Ala Gly Arg Val Asp Lys
1370                1375                1380

Leu Gly Glu Ala Gly Ser Ser Ala Tyr Asp Thr Val Ser Gly Ile
1385                1390                1395

Glu Asn Val Val Gly Thr Glu Leu Ala Asp Arg Ile Thr Gly Asp
1400                1405                1410

Ala Gln Ala Asn Val Leu Arg Gly Ala Gly Gly Ala Asp Val Leu
1415                1420                1425

Ala Gly Gly Glu Gly Asp Asp Val Leu Leu Gly Gly Glu Gly Asp
1430                1435                1440

Asp Gln Leu Ser Gly Asp Ala Gly Arg Asp Arg Leu Tyr Gly Glu
1445                1450                1455

Ala Gly Asp Asp Trp Phe Phe Gln Asp Ala Ala Asn Ala Gly Asn
1460                1465                1470

Leu Leu Asp Gly Gly Asp Gly Asn Asp Thr Val Asp Phe Ser Gly
1475                1480                1485

Pro Gly Arg Gly Leu Asp Ala Gly Ala Lys Gly Val Phe Leu Ser
1490                1495                1500

Leu Gly Lys Gly Phe Ala Ser Leu Met Asp Glu Pro Glu Thr Ser
1505                1510                1515

Asn Val Leu Arg His Ile Glu Asn Ala Val Gly Ser Val Arg Asp
1520                1525                1530

Asp Val Leu Ile Gly Asp Ala Gly Ala Asn Val Leu Asn Gly Leu
1535                1540                1545

Ala Gly Asn Asp Val Leu Ser Gly Gly Ala Gly Asp Asp Val Leu
1550                1555                1560

Leu Gly Asp Glu Gly Ser Asp Leu Leu Ser Gly Asp Ala Gly Asn
1565                1570                1575
```

```
Asp Asp  Leu Phe Gly Gly Gln  Gly Asp Asp Thr Tyr  Leu Phe Gly
    1580                 1585                 1590

Ala Gly  Tyr Gly His Asp Thr  Ile Tyr Glu Ser Gly  Gly Gly His
    1595                 1600                 1605

Asp Thr  Ile Arg Ile Asn Ala  Gly Ala Asp Gln Leu  Trp Phe Ala
    1610                 1615                 1620

Arg Gln  Gly Asn Asp Leu Glu  Ile Arg Ile Leu Gly  Thr Asp Asp
    1625                 1630                 1635

Ala Leu  Thr Val His Asp Trp  Tyr Arg Asp Ala Asp  His Arg Val
    1640                 1645                 1650

Glu Ala  Ile His Ala Ala Asn  Gln Ala Ile Asp Pro  Ala Gly Ile
    1655                 1660                 1665

Glu Lys  Leu Val Glu Ala Met  Ala Gln Tyr Pro Asp  Pro Gly Ala
    1670                 1675                 1680

Ala Ala  Ala Ala Pro Pro Ala  Ala Arg Val Pro Asp  Thr Leu Met
    1685                 1690                 1695

Gln Ser  Leu Ala Val Asn Trp  Arg
    1700                 1705

<210> SEQ ID NO 8
<211> LENGTH: 1706
<212> TYPE: PRT
<213> ORGANISM: Bordetella hinzii

<400> SEQUENCE: 8

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240
```

```
Leu Trp Lys Ile Ala Arg Ala Gly Ala Arg Ser Ala Val Gly Thr Glu
            245                 250                 255

Ala Arg Arg Gln Phe Arg Tyr Asp Gly Asp Met Asn Ile Gly Val Ile
        260                 265                 270

Thr Asp Phe Glu Leu Glu Val Arg Asn Ala Leu Asn Arg Arg Ala His
            275                 280                 285

Ala Val Gly Ala Gln Asp Val Gln His Gly Thr Glu Gln Asn Asn
        290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
            325                 330                 335

Gln Arg Gly Glu Gly Tyr Val Phe Tyr Glu Asn Arg Ala Tyr Gly Val
        340                 345                 350

Ala Gly Lys Ser Leu Phe Asp Asp Gly Leu Gly Ala Ala Pro Gly Val
            355                 360                 365

Pro Ser Gly Arg Ser Lys Phe Ser Pro Asp Val Leu Glu Thr Val Pro
        370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
            405                 410                 415

Leu Gly Glu Val Ser Asp Met Ala Ala Val Glu Ala Ala Glu Leu Glu
        420                 425                 430

Met Thr Arg Gln Val Leu His Ala Gly Ala Arg Gln Asp Asp Ala Glu
            435                 440                 445

Pro Gly Val Ser Gly Ala Ser Ala His Trp Gly Gln Arg Ala Leu Gln
        450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
            485                 490                 495

Ala Ala Ser Leu Ser Ala Ala Val Phe Gly Leu Gly Glu Ala Ser Ser
        500                 505                 510

Ala Val Ala Glu Thr Val Ser Gly Phe Phe Arg Gly Ser Ser Arg Trp
        515                 520                 525

Ala Gly Gly Phe Gly Val Ala Gly Gly Ala Met Ala Leu Gly Gly Gly
        530                 535                 540

Ile Ala Ala Ala Val Gly Ala Gly Met Ser Leu Thr Asp Asp Ala Pro
545                 550                 555                 560

Ala Gly Gln Lys Ala Ala Ala Gly Ala Glu Ile Ala Leu Gln Leu Thr
            565                 570                 575

Gly Gly Thr Val Glu Leu Ala Ser Ser Ile Ala Leu Ala Leu Ala Ala
        580                 585                 590

Ala Arg Gly Val Thr Ser Gly Leu Gln Val Ala Gly Ala Ser Ala Gly
        595                 600                 605

Ala Ala Ala Gly Ala Leu Ala Ala Leu Ser Pro Met Glu Ile Tyr
        610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Glu Gly Asp Ala Leu Leu Ala Gln
            645                 650                 655
```

-continued

Leu Tyr Arg Asp Lys Thr Ala Ala Glu Gly Ala Val Ala Gly Val Ser
            660                 665                 670

Ala Val Leu Ser Thr Val Gly Ala Ala Val Ser Ile Ala Ala Ala Ala
        675                 680                 685

Ser Val Val Gly Ala Pro Val Ala Val Val Thr Ser Leu Leu Thr Gly
    690                 695                 700

Ala Leu Asn Gly Ile Leu Arg Gly Val Gln Gln Pro Ile Ile Glu Lys
705                 710                 715                 720

Leu Ala Asn Asp Tyr Ala Arg Lys Ile Asp Glu Leu Gly Gly Pro Gln
                725                 730                 735

Ala Tyr Phe Glu Lys Asn Leu Gln Ala Arg His Glu Gln Leu Ala Asn
            740                 745                 750

Ser Asp Gly Leu Arg Lys Met Leu Ala Asp Leu Gln Ala Gly Trp Asn
        755                 760                 765

Ala Ser Ser Val Ile Gly Val Gln Thr Thr Glu Ile Ser Lys Ser Ala
    770                 775                 780

Leu Glu Leu Ala Ala Ile Thr Gly Asn Ala Asp Asn Leu Lys Ser Val
785                 790                 795                 800

Asp Val Phe Val Asp Arg Phe Val Gln Gly Glu Arg Val Ala Gly Gln
                805                 810                 815

Pro Val Val Leu Asp Val Ala Ala Gly Gly Ile Asp Ile Ala Ser Arg
            820                 825                 830

Lys Gly Glu Arg Pro Ala Leu Thr Phe Ile Thr Pro Leu Ala Ala Pro
        835                 840                 845

Gly Glu Glu Gln Arg Arg Arg Thr Lys Thr Gly Lys Ser Glu Phe Thr
    850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
                885                 890                 895

Val Asp Ala Asn Gly Val Leu Lys His Ser Ile Lys Leu Asp Val Ile
            900                 905                 910

Gly Gly Asp Gly Asp Val Val Leu Ala Asn Ala Ser Arg Ile His
        915                 920                 925

Tyr Asp Gly Gly Ala Gly Thr Asn Thr Val Ser Tyr Ala Ala Leu Gly
    930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                965                 970                 975

Gln Thr Thr Ala Tyr Gly Lys Arg Thr Glu Asn Val Gln Tyr Arg His
            980                 985                 990

Val Glu Leu Ala Arg Val Gly Gln Leu Val Glu Val Asp Thr Leu Glu
        995                 1000                1005

His Val Gln His Ile Ile Gly Gly Ala Gly Asn Asp Ser Ile Thr
    1010                1015                1020

Gly Asn Ala His Asp Asn Phe Leu Ala Gly Gly Ser Gly Asp Asp
    1025                1030                1035

Arg Leu Asp Gly Gly Ala Gly Asn Asp Thr Leu Val Gly Gly Glu
    1040                1045                1050

Gly Gln Asn Thr Val Ile Gly Gly Ala Gly Asp Asp Val Phe Leu
    1055                1060                1065

Gln Asp Leu Gly Val Trp Ser Asn Gln Leu Asp Gly Gly Ala Gly

-continued

```
           1070                1075                1080
Val Asp Thr Val Lys Tyr Asn Val His Gln Pro Ser Glu Glu Arg
   1085                1090                1095
Leu Glu Arg Met Gly Asp Thr Gly Ile His Ala Asp Leu Gln Lys
   1100                1105                1110
Gly Thr Val Glu Lys Trp Pro Ala Leu Asn Leu Phe Ser Val Asp
   1115                1120                1125
His Val Lys Asn Ile Glu Asn Leu His Gly Ser Arg Leu Asn Asp
   1130                1135                1140
Arg Ile Ala Gly Asp Asp Gln Asp Asn Glu Leu Trp Gly His Asp
   1145                1150                1155
Gly Asn Asp Thr Ile Arg Gly Arg Gly Gly Asp Asp Ile Leu Arg
   1160                1165                1170
Gly Gly Leu Gly Leu Asp Thr Leu Tyr Gly Glu Asp Gly Asn Asp
   1175                1180                1185
Ile Phe Leu Gln Asp Asp Glu Thr Val Ser Asp Ile Asp Gly
   1190                1195                1200
Gly Ala Gly Leu Asp Thr Val Asp Tyr Ser Ala Met Ile His Pro
   1205                1210                1215
Gly Arg Ile Val Ala Pro His Glu Tyr Gly Phe Gly Ile Glu Ala
   1220                1225                1230
Asp Leu Ser Arg Glu Trp Val Arg Lys Ala Ser Ala Leu Gly Val
   1235                1240                1245
Asp Tyr Tyr Asp Asn Val Arg Asn Val Glu Asn Val Ile Gly Thr
   1250                1255                1260
Ser Met Lys Asp Val Leu Ile Gly Asp Ala Gln Ala Asn Thr Leu
   1265                1270                1275
Met Gly Gln Gly Gly Asp Asp Thr Val Arg Gly Gly Asp Gly Asp
   1280                1285                1290
Asp Leu Leu Phe Gly Gly Asp Gly Asn Asp Met Leu Tyr Gly Asp
   1295                1300                1305
Ala Gly Asn Asp Thr Leu Tyr Gly Gly Leu Gly Asp Asp Thr Leu
   1310                1315                1320
Glu Gly Gly Ala Gly Asn Asp Trp Phe Gly Gln Thr Gln Ala Arg
   1325                1330                1335
Glu His Asp Val Leu Arg Gly Gly Asp Gly Val Asp Thr Val Asp
   1340                1345                1350
Tyr Ser Gln Thr Gly Ala His Ala Gly Ile Ala Ala Gly Arg Ile
   1355                1360                1365
Gly Leu Gly Ile Leu Ala Asp Leu Gly Ala Gly Arg Val Asp Lys
   1370                1375                1380
Leu Gly Glu Ala Gly Ser Ser Ala Tyr Asp Thr Val Ser Gly Ile
   1385                1390                1395
Glu Asn Val Val Gly Thr Glu Leu Ala Asp Arg Ile Thr Gly Asp
   1400                1405                1410
Ala Gln Ala Asn Val Leu Arg Gly Ala Gly Gly Ala Asp Val Leu
   1415                1420                1425
Ala Gly Gly Glu Gly Asp Asp Val Leu Leu Gly Gly Asp Gly Asp
   1430                1435                1440
Asp Gln Leu Ser Gly Asp Ala Gly Arg Asp Arg Leu Tyr Gly Glu
   1445                1450                1455
Ala Gly Asp Asp Trp Phe Phe Gln Asp Ala Ala Asn Ala Gly Asn
   1460                1465                1470
```

```
Leu Leu  Asp Gly Gly Asp Gly  Arg Asp Thr Val Asp  Phe Ser Gly
    1475                 1480                 1485

Pro Gly  Arg Gly Leu Asp Ala  Gly Ala Lys Gly Val  Phe Leu Ser
    1490                 1495                 1500

Leu Gly  Lys Gly Phe Ala Ser  Leu Met Asp Glu Pro  Glu Thr Ser
    1505                 1510                 1515

Asn Val  Leu Arg Asn Ile Glu  Asn Ala Val Gly Ser  Ala Arg Asp
    1520                 1525                 1530

Asp Val  Leu Ile Gly Asp Ala  Gly Ala Asn Val Leu  Asn Gly Leu
    1535                 1540                 1545

Ala Gly  Asn Asp Val Leu Ser  Gly Gly Ala Gly Asp  Asp Val Leu
    1550                 1555                 1560

Leu Gly  Asp Glu Gly Ser Asp  Leu Leu Ser Gly Asp  Ala Gly Asn
    1565                 1570                 1575

Asp Asp  Leu Phe Gly Gly Gln  Gly Asp Asp Thr Tyr  Leu Phe Gly
    1580                 1585                 1590

Val Gly  Tyr Gly His Asp Thr  Ile Tyr Glu Ser Gly  Gly Gly His
    1595                 1600                 1605

Asp Thr  Ile Arg Ile Asn Ala  Gly Ala Asp Gln Leu  Trp Phe Ala
    1610                 1615                 1620

Arg Gln  Gly Asn Asp Leu Glu  Ile Arg Ile Leu Gly  Thr Asp Asp
    1625                 1630                 1635

Ala Leu  Thr Val His Asp Trp  Tyr Arg Asp Ala Asp  His Arg Val
    1640                 1645                 1650

Glu Ile  Ile His Ala Ala Asn  Gln Ala Val Asp Gln  Ala Gly Ile
    1655                 1660                 1665

Glu Lys  Leu Val Glu Ala Met  Ala Gln Tyr Pro Asp  Pro Gly Ala
    1670                 1675                 1680

Ala Ala  Ala Ala Pro Pro Ala  Ala Arg Val Pro Asp  Thr Leu Met
    1685                 1690                 1695

Gln Ser  Leu Ala Val Asn Trp  Arg
    1700                 1705

<210> SEQ ID NO 9
<211> LENGTH: 1705
<212> TYPE: PRT
<213> ORGANISM: Bordetella bronchiseptica

<400> SEQUENCE: 9

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
```

-continued

```
            115                 120                 125
Val Thr Gly Met Ala Asp Gly Val Ala Ser Asn His Ala Gly Tyr
        130                 135                 140
Glu Gln Phe Glu Phe Arg Val Lys Glu Thr Ser Asp Gly Arg Tyr Ala
145                 150                 155                 160
Val Gln Tyr Arg Arg Lys Gly Asp Asp Phe Glu Ala Val Lys Val
                165                 170                 175
Ile Gly Asn Ala Ala Gly Ile Pro Leu Thr Ala Asp Ile Asp Met Phe
                180                 185                 190
Ala Ile Met Pro His Leu Ser Asn Phe Arg Asp Ser Ala Arg Ser Ser
            195                 200                 205
Val Thr Ser Gly Asp Ser Val Thr Asp Tyr Leu Ala Arg Thr Arg Arg
        210                 215                 220
Ala Ala Ser Glu Ala Thr Gly Gly Leu Asp Arg Glu Arg Ile Asp Leu
225                 230                 235                 240
Leu Trp Lys Ile Ala Arg Ala Gly Ala Arg Ser Ala Val Gly Thr Glu
                245                 250                 255
Ala Arg Arg Gln Phe Arg Tyr Asp Gly Asp Met Asn Ile Gly Val Ile
                260                 265                 270
Thr Asp Phe Glu Leu Glu Val Arg Asn Ala Leu Asn Arg Arg Ala His
            275                 280                 285
Ala Val Gly Arg Gln Asp Val Val Gln His Gly Thr Glu Gln Asn Asn
        290                 295                 300
Pro Phe Pro Glu Ala Asp Glu Lys Ile Phe Val Val Ser Ala Thr Gly
305                 310                 315                 320
Glu Ser Gln Met Leu Thr Arg Gly Gln Leu Lys Glu Tyr Ile Gly Gln
                325                 330                 335
Gln Arg Gly Glu Gly Tyr Val Phe Tyr Glu Asn Arg Ala Tyr Gly Val
                340                 345                 350
Ala Gly Lys Ser Leu Phe Asp Asp Gly Leu Gly Ala Ala Pro Gly Val
            355                 360                 365
Pro Gly Arg Arg Ser Lys Ser Ser Pro Asp Val Leu Glu Thr Val Pro
        370                 375                 380
Ala Ser Pro Gly Leu Arg Arg Pro Ser Leu Gly Ala Val Glu Arg Gln
385                 390                 395                 400
Asp Ser Gly Tyr Asp Ser Leu Asp Gly Val Gly Ser Arg Ser Phe Ser
                405                 410                 415
Leu Gly Glu Val Ser Asp Met Ala Ala Val Glu Ala Ala Glu Leu Glu
                420                 425                 430
Met Thr Arg Gln Val Leu His Ala Gly Ala Arg Gln Asp Asp Ala Glu
            435                 440                 445
Pro Gly Val Ser Gly Ala Ser Ala His Trp Gly Gln Arg Ala Leu Gln
        450                 455                 460
Gly Ala Gln Ala Val Ala Ala Gln Arg Leu Val His Ala Ile Ala
465                 470                 475                 480
Leu Met Thr Gln Phe Gly Arg Ala Gly Ser Thr Asn Thr Pro Gln Glu
                485                 490                 495
Ala Ala Ser Leu Ser Ala Ala Val Phe Gly Leu Gly Glu Ala Ser Ser
            500                 505                 510
Ala Val Ala Glu Thr Val Ser Gly Phe Phe Arg Gly Ser Ser Arg Trp
        515                 520                 525
Ala Gly Gly Phe Gly Val Ala Gly Gly Ala Met Ala Leu Gly Gly Gly
    530                 535                 540
```

```
Ile Gly Ala Val Gly Ala Gly Met Ser Leu Thr Asp Asp Ala Pro Ala
545                 550                 555                 560

Gly Gln Lys Ala Ala Gly Ala Glu Ile Ala Leu Gln Leu Thr Gly
            565                 570                 575

Gly Thr Val Glu Leu Ala Ser Ser Ile Ala Leu Ala Leu Ala Ala Ala
                580                 585                 590

Arg Gly Val Thr Ser Gly Leu Gln Val Ala Gly Ala Ser Ala Gly Ala
            595                 600                 605

Ala Ala Gly Ala Leu Ala Ala Ala Leu Ser Pro Met Glu Ile Tyr Gly
610                 615                 620

Leu Val Gln Gln Ser His Tyr Ala Asp Gln Leu Asp Lys Leu Ala Gln
625                 630                 635                 640

Glu Ser Ser Ala Tyr Gly Tyr Glu Gly Asp Ala Leu Leu Ala Gln Leu
                645                 650                 655

Tyr Arg Asp Lys Thr Ala Ala Glu Gly Ala Val Ala Gly Val Ser Ala
            660                 665                 670

Val Leu Ser Thr Val Gly Ala Ala Val Ser Ile Ala Ala Ala Ala Ser
            675                 680                 685

Val Val Gly Ala Pro Val Ala Val Val Thr Ser Leu Leu Thr Gly Ala
690                 695                 700

Leu Asn Gly Ile Leu Arg Gly Val Gln Gln Pro Ile Ile Glu Lys Leu
705                 710                 715                 720

Ala Asn Asp Tyr Ala Arg Lys Ile Asp Glu Leu Gly Gly Pro Gln Ala
                725                 730                 735

Tyr Phe Glu Lys Asn Leu Gln Ala Arg His Gln Leu Ala Asn Ser
            740                 745                 750

Asp Gly Leu Arg Lys Met Leu Ala Asp Leu Gln Ala Gly Trp Asn Ala
            755                 760                 765

Ser Ser Val Ile Gly Val Gln Thr Thr Glu Ile Ser Lys Ser Ala Leu
770                 775                 780

Glu Leu Ala Ala Ile Thr Gly Asn Ala Asp Asn Leu Lys Ser Ala Asp
785                 790                 795                 800

Val Phe Val Asp Arg Phe Ile Gln Gly Glu Arg Val Ala Gly Gln Pro
                805                 810                 815

Val Val Leu Asp Val Ala Ala Gly Gly Ile Asp Ile Ala Ser Arg Lys
            820                 825                 830

Gly Glu Arg Pro Ala Leu Thr Phe Ile Thr Pro Leu Ala Ala Pro Gly
            835                 840                 845

Glu Glu Gln Arg Arg Thr Lys Thr Gly Lys Ser Glu Phe Thr Thr
850                 855                 860

Phe Val Glu Ile Val Gly Lys Gln Asp Arg Trp Arg Ile Arg Asp Gly
865                 870                 875                 880

Ala Ala Asp Thr Thr Ile Asp Leu Ala Lys Val Val Ser Gln Leu Val
                885                 890                 895

Asp Ala Asn Gly Val Leu Lys His Ser Ile Lys Leu Glu Val Ile Gly
            900                 905                 910

Gly Asp Gly Asp Asp Val Val Leu Ala Asn Ala Ser Arg Ile His Tyr
            915                 920                 925

Asp Gly Gly Ala Gly Thr Asn Thr Val Ser Tyr Ala Ala Leu Gly Arg
930                 935                 940

Gln Asp Ser Ile Thr Val Ser Ala Asp Gly Glu Arg Phe Asn Val Arg
945                 950                 955                 960
```

```
Lys Gln Leu Asn Asn Ala Asn Val Tyr Arg Glu Gly Val Ala Thr Gln
                965                 970                 975

Lys Thr Ala Tyr Gly Lys Arg Thr Glu Asn Val Gln Tyr Arg His Val
            980                 985                 990

Glu Leu Ala Arg Val Gly Gln Leu Val Glu Val Asp Thr Leu Glu His
        995                 1000                1005

Val Gln His Ile Ile Gly Gly Ala Gly Asn Asp Ser Ile Thr Gly
    1010                1015                1020

Asn Ala His Asp Asn Phe Leu Ala Gly Ala Gly Asp Asp Arg
    1025                1030                1035

Leu Asp Gly Gly Ala Gly Asn Asp Thr Leu Val Gly Gly Glu Gly
    1040                1045                1050

His Asn Thr Val Val Gly Ala Gly Asp Asp Val Phe Leu Gln
    1055                1060                1065

Asp Leu Gly Val Trp Ser Asn Gln Leu Asp Gly Gly Ala Gly Val
    1070                1075                1080

Asp Thr Val Lys Tyr Asn Val His Gln Pro Ser Glu Glu Arg Leu
    1085                1090                1095

Glu Arg Met Gly Asp Thr Gly Ile His Ala Asp Leu Gln Lys Gly
    1100                1105                1110

Thr Val Glu Lys Trp Pro Ala Leu Asn Leu Phe Ser Val Asp His
    1115                1120                1125

Val Lys Asn Ile Glu Asn Leu His Gly Ser Ser Leu Asn Asp Ser
    1130                1135                1140

Ile Ala Gly Asp Asp Arg Asp Asn Glu Leu Trp Gly Asp Asp Gly
    1145                1150                1155

Asn Asp Thr Ile His Gly Arg Gly Gly Asp Asp Ile Leu Arg Gly
    1160                1165                1170

Gly Leu Gly Leu Asp Thr Leu Tyr Gly Glu Asp Gly Asn Asp Ile
    1175                1180                1185

Phe Leu Gln Asp Asp Glu Thr Val Ser Asp Ile Asp Gly Gly
    1190                1195                1200

Ala Gly Leu Asp Thr Val Asp Tyr Ser Ala Met Ile His Ala Gly
    1205                1210                1215

Lys Ile Val Ala Pro His Glu Tyr Gly Phe Gly Ile Glu Ala Asp
    1220                1225                1230

Leu Ser Glu Gly Trp Val Arg Lys Ala Ala Arg Arg Gly Met Asp
    1235                1240                1245

Tyr Tyr Asp Ser Val Arg Ser Val Glu Asn Val Ile Gly Thr Ser
    1250                1255                1260

Met Lys Asp Val Leu Ile Gly Asp Ala Gln Ala Asn Thr Leu Met
    1265                1270                1275

Gly Gln Gly Gly Asp Asp Thr Val Arg Gly Gly Asp Gly Asp Asp
    1280                1285                1290

Leu Leu Phe Gly Gly Asp Gly Asn Asp Met Leu Tyr Gly Asp Ala
    1295                1300                1305

Gly Asn Asp Thr Leu Tyr Gly Gly Leu Gly Asp Asp Thr Leu Glu
    1310                1315                1320

Gly Gly Ala Gly Asn Asp Trp Phe Gly Gln Thr Pro Ala Arg Glu
    1325                1330                1335

His Asp Val Leu Arg Gly Gly Ala Gly Val Asp Thr Val Asp Tyr
    1340                1345                1350

Ser Gln Ala Gly Ala His Ala Gly Val Ala Thr Gly Arg Ile Gly
```

```
               1355                1360                1365

Leu Gly  Ile Leu Ala Asp  Leu Gly Ala Arg  Val Asp Lys Leu
         1370                1375                1380

Gly Glu  Ala Gly Ser Ser  Ala Tyr Asp Thr  Val Ser Gly Ile Glu
1385                1390                1395

Asn Val  Val Gly Thr Glu  Leu Ala Asp Arg  Ile Thr Gly Asp Ala
1400                1405                1410

Gln Ala  Asn Val Leu Arg  Gly Ala Gly Ala  Asp Val Leu Ala
1415                1420                1425

Gly Gly  Glu Gly Asp Asp  Val Leu Leu Gly  Gly Asp Gly Asp Asp
1430                1435                1440

Gln Leu  Ser Gly Asp Ala  Gly Arg Asp Arg  Leu Tyr Gly Glu Ala
1445                1450                1455

Gly Asp  Asp Trp Phe Phe  Gln Asp Ala Ala  Asn Ala Gly Asn Leu
1460                1465                1470

Leu Asp  Gly Gly Asp Gly  Asn Asp Thr Val  Asp Phe Ser Gly Pro
1475                1480                1485

Gly Arg  Gly Leu Asp Ala  Gly Ala Lys Gly  Val Phe Leu Ser Leu
1490                1495                1500

Gly Lys  Gly Phe Ala Ser  Leu Met Asp Glu  Pro Glu Thr Ser Asn
1505                1510                1515

Val Leu  Arg His Ile Glu  Asn Ala Val Gly  Ser Val Arg Asp Asp
1520                1525                1530

Val Leu  Ile Gly Asp Ala  Gly Ala Asn Val  Leu Asn Gly Leu Ala
1535                1540                1545

Gly Asn  Asp Val Leu Ser  Gly Gly Ala Gly  Asp Asp Val Leu Leu
1550                1555                1560

Gly Asp  Glu Gly Ser Asp  Leu Leu Ser Gly  Asp Ala Gly Asn Asp
1565                1570                1575

Asp Leu  Phe Gly Gly Gln  Gly Asp Asp Thr  Tyr Leu Phe Gly Ala
1580                1585                1590

Gly Tyr  Gly His Asp Thr  Ile Tyr Glu Ser  Gly Gly His Asp
1595                1600                1605

Thr Ile  Arg Ile Asn Ala  Gly Ala Asp Gln  Leu Trp Phe Ala Arg
1610                1615                1620

Gln Gly  Asn Asp Leu Glu  Ile Arg Ile Leu  Gly Thr Asp Asp Ala
1625                1630                1635

Leu Thr  Val His Asp Trp  Tyr Arg Asp Ala  Asp His Arg Val Glu
1640                1645                1650

Ala Ile  His Ala Ala Asn  Gln Ala Ile Asp  Pro Ala Gly Ile Glu
1655                1660                1665

Lys Leu  Val Glu Ala Met  Ala Gln Tyr Pro  Asp Pro Gly Ala Ala
1670                1675                1680

Ala Ala  Ala Pro Pro Ala  Ala Arg Val Pro  Asp Thr Leu Met Gln
1685                1690                1695

Ser Leu  Ala Val Asn Trp  Arg
1700                1705

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 10
gggggacgat cgtcgggggg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tccatgacgt tcctgacgtt                                              20

<210> SEQ ID NO 12
<211> LENGTH: 8
<212> TYPE: PRT
<213> ORGANISM: Unknown
<220> FEATURE:
<223> OTHER INFORMATION: Description of Unknown: 'SIINFEKL'
      family peptide motif

<400> SEQUENCE: 12

Ser Ile Ile Asn Phe Glu Lys Leu
1               5
```

MUTANT CYAA POLYPEPTIDES AND POLYPEPTIDE DERIVATIVES SUITABLE FOR THE DELIVERY OF IMMUNOGENIC MOLECULES INTO A CELL

CROSS REFERENCE TO RELATED APPLICATIONS

This application is a national phase application based on PCT/EP2010/053795, filed Mar. 23, 2010, which claims the priority of European Patent Application No. 09155929.4, filed Mar. 23, 2009; and claims the priority of U.S. application Ser. No. 12/409,324, filed Mar. 23, 2009, the contents of all of which are incorporated herein by reference.

SEQUENCE LISTING

The instant application contains a Sequence Listing which has been submitted in ASCII format via EFS-Web and is hereby incorporated by reference in its entirety. Said ASCII copy, created on May 20, 2013, is named 03495.0446_SL.txt and is 129,227 bytes in size.

The invention relates to polypeptides suitable for use in the delivery of one or more molecules into a cell.

In particular, the invention relates to polypeptides suitable for use in the delivery of one or more molecules which are able to elicite an immune response into a host, especially by targeting cells which express the CD11b/CD18 receptor (also referred to herein as "CD11b expressing cells").

The invention is more particularly directed to polypeptides derived from an adenylate cyclase protein (CyaA), the latter being used either under the form of a toxin or of a detoxified protein or toxoid, which are mutant polypeptides. Said mutant polypeptides are capable of retaining the binding activity of native CyaA to a target cell and preferably of also retaining the translocating activity of native CyaA through its N-terminal domain into target cells and furthermore have a pore-forming activity which is reduced or suppressed as compared to that of the native CyaA toxin.

The invention relates in particular to the use of said polypeptides as proteinaceous vectors. Accordingly the mutant polypeptides are further combined with non-CyaA molecules, thereby giving rise to polypeptide derivatives, wherein said molecules have a preventive vaccinal and/or therapeutic interest when administered to a host.

The polypeptides according to the invention are suitable for use as proteinaceous vectors for the delivery of a molecule, in particular of a polypeptidic molecule having an amino acid sequence comprising one or more epitope(s), especially antigens, into a cell, in particular in CD11b expressing cells.

The invention thus also relates to a polypeptide derivative (a derivative of the mutant polypeptide of the invention) which comprises or consists of a mutant polypeptide according to the invention recombined to one or more molecules, in particular to one or more molecules suitable for eliciting an immune response, thus constituting a recombinant polypeptide or a fusion polypeptide. The invention also relates to polypeptide derivatives obtained by chemically grafting said molecule(s) to the mutant polypeptides.

According to an embodiment, the polypeptide derivatives according to the invention are suitable for use in prophylactic treatment and especially in vaccination and in therapy including in immunotherapy, in particular for eliciting an immune response in a subject.

The native CyaA used in the context of the present invention for the design of the polypeptides of the invention is the adenylate cyclase produced primarily in *Bordetella* organisms, especially in *Bordetella Pertussis* and which has the following features and properties disclosed for the purpose of characterising said protein in the context of the invention.

The bi-functional RTX adenylate cyclase toxin-hemolysin (also designated herewith as the adenylate cyclase toxin (CyaA, ACT, or AC-Hly) is a key virulence factor of *Bordetella pertussis* which is the causative agent of whooping cough (1). Its 1706 residues-long polypeptide is a fusion of an N-terminal adenylate cyclase (AC) enzyme domain or part (~400 residues) to a pore-forming RTX hemolysin (Repeat in ToXin cytolysin) of ~1306 residues constituting the C-terminal part or domain (2). The latter harbors the sites of activation of proCyaA to CyaA by covalent post-translational palmitoylation of ε-amino groups of $Lys^{860}$ and $Lys^{983}$, as well as the numerous RTX repeats forming ~40 calcium binding sites, the loading of which is required for cytotoxic activity of CyaA (3, 4). The CyaA protein is indeed synthesized as an inactive protoxin which is converted into an active toxin by post translational palmitoylation of two internal lysine residues (lysines 860 and 983). This post translational modification requires the expression with the cyaA gene, of an accessory gene i.e., cyaC which is located nearby cyaA on *B. pertussis* chromosome.

The toxin primarily targets host myeloid phagocytes expressing the $\alpha_M\beta_2$ integrin receptor, known also as CD11b/CD18, CR3 or Mac-1 (5). Said toxin especially binds to the CD11b/CD18 receptor of cells expressing the same through a receptor binding site present in its C-terminal part. These cells are accordingly target cells for the native toxin and also for the polypeptides of the invention. CyaA inserts into cytoplasmic membrane of cells and translocates the AC enzyme domain into the cytosol of said target cells (6, 7). Inside cells, the AC is activated by calmodulin and catalyzes uncontrolled conversion of cellular ATP to cAMP, a key second messenger molecule provoking impairment of bactericidal functions of phagocytes (1). At high doses (>100 ng/ml), CyaA-catalyzed dissipation of ATP into cAMP becomes cytotoxic and promotes apoptosis or even rapid necrotic death and lysis of $CD11b^+$ monocytes (8, 9).

Recently, the inventors showed that CyaA binds N-linked oligosaccharides of its CD11b/CD18 receptor (10). This suggests that low specificity interactions with glycans of ubiquitous cell surface proteins or glycolipids may account for the about two order of magnitude reduced but readily detectable capacity of CyaA to penetrate also cells lacking CD11b/CD18. Indeed, due to the extremely high specific catalytic activity of the AC domain, CyaA was found to substantially elevate cAMP also in mammalian and avian erythrocytes, lymphocytes, lymphoma, neuroblastoma, CHO, or tracheal epithelial cells (1, 11).

It has already been proposed in the prior art to provide detoxified toxin also called toxoid, wherein the adenylate cyclase activity is decreased, especially essentially suppressed. Such CyaA/AC⁻ toxoid may be used to achieve the preparation of the polypeptides of the invention.

Besides elevating cAMP, the toxin exhibits also a moderate hemolytic activity on mammalian and avian erythrocytes. This is due to the capacity to form small cation-selective pores of an estimated diameter of 0.6 to 0.8 nm, which permeabilize cellular membrane and eventually provoke colloid-osmotic cell lysis (12). Recently, the inventors and others have shown that the pore-forming activity of CyaA synergizes with its cell-invasive AC enzyme activity and contributes to the overall cytolytic potency of CyaA on $CD11b^+$ cells (13, 14). Due to an intact pore-forming (hemolytic) capacity, in the absence of osmoprotectants such as serum, the enzymatically inactive CyaA/AC⁻ toxoid (15) still exhibits a full hemolytic activity on erythrocytes and a residual, about tenfold reduced cytolytic activity on CD11b-expressing monocytes (8), which sets a limit to its use in therapy.

The hemolytic (pore-forming) and AC membrane translocation (cell-invasive) activities of CyaA were early on found to be dissociable by low calcium concentration, low temperature (16) and by the extent and nature of acylation of CyaA (4, 12, 17). Moreover, the two activities differ substantially in sensitivity to charge-reversing or neutral substitutions of glutamates at positions 509, 516, 570 and 581 within the hydrophobic domain (8, 13, 18). The cell-invasive and pore-forming activities of CyaA were thus proposed to be mutually independent and operating in parallel in target cell membrane. The model illustrated in FIG. 5A, suggests that two distinct CyaA conformers insert into target cell membrane in parallel, one being the translocation precursor, accounting for delivery of the AC domain across cellular membrane with concomitant influx of calcium ions into cells, the other being a pore precursor eventually forming oligomeric pores (13, 18, 19).

The inventors have now tested this model and refined it, showing that the pore-forming activity is not involved in translocation of the AC domain across target cell.

In the present invention, the inventors initially designed CyaA mutant polypeptides, based especially on the adenylate cyclase of *Bordetella pertussis*, either in the toxin or in the toxoid format, having a combination of substitutions within the pore-forming (E570Q) and acylation-bearing (K860R) domains and showed that this specific combination of substitutions selectively abolished the cell-permeabilizing activity of CyaA, thus eliminating the residual cytolytic activity of CyaA/AC− toxoids on CD11b+ cells. At the same time, the E570Q+K860R construct retained a full capacity to translocate the AC domain into cytosol of cells to elevate cellular cAMP and its toxoid was fully capable to deliver epitopes containing molecules inserted within said construct to the cytosolic pathway of dendritic cells for MHC class I-restricted presentation and induction of specific cytotoxic T cell responses in vivo.

The CyaA/233OVA/E570Q+K860R mutant designed by the inventors, and in which an OVA antigenic peptide is inserted as described in the examples, is the first construct illustrative of the capacity of the CyaA mutant to provide an importantly reduced capacity to permeabilize cells while remaining fully capable of translocating the AC domain across cellular membrane.

The inventors have now designed particular constructs, illustrated especially as a CyaA/E570Q+K860R/AC⁻ toxoid and have shown that despite its much reduced cell-permeabilizing (cytolytic) activity, it remains fully active in antigen delivery into CD11b⁺ APCs. The inventors have further shown that the overall cytolytic activity of the illustrative CyaA/E570Q+K860R/AC⁻ toxoid is very low. It is thus devoid of residual toxicity in an animal or human host and is therefore highly suitable for use in therapy.

The invention thus provides new polypeptides, which are toxoids and have an enhanced safety profile and can be used as proteinaceous vectors for the delivery of molecules of interest, in particular of immunogenic peptidic sequences, to cells of a patient in need of a treatment, and more particularly to cells expressing CD11b.

Based on the experiments carried out by the inventors it has thus been possible to define and provide a polypeptide which is a mutant of an adenylate cyclase protein (mutant polypeptide) and whose amino acid sequence comprises or consists of one of the following sequences:

a) the amino acid sequence of the adenylate cyclase (CyaA) of *Bordetella pertussis, Bordetella parapertussis* or *Bordetella hinzii* wherein the following mutations have been performed:
  (i) the substitution of the glutamic acid residue at position 570 by a glutamine residue (E570Q) or by a conservative amino acid residue, and
  (ii) the substitution of the lysine residue at position 860 by an arginine residue (K860R) or by a conservative amino acid residue, or;
b) an amino acid sequence of a fragment of the adenylate cyclase of *Bordetella pertussis, Bordetella parapertussis* or *Bordetella hinzii*, which fragment has the capacity of the CyaA protein of *Bordetella pertussis* to bind to a target cell and the capacity to translocate its N-terminal adenylate cyclase enzyme domain or part thereof into said cell, wherein said fragment further contains the following mutated amino acid residues located at positions 570 and 860 in said adenylate cyclase: E570Q and K860R, or
c) an amino acid sequence which differs from the amino acid sequence as defined in a) or b) by one or more amino acid residue substitutions and/or insertions and which has the capacity of the CyaA protein of *Bordetella Pertussis* to bind to a target cell and the capacity to translocate its N-terminal adenylate cyclase enzyme domain or part thereof into said cell, wherein said amino acid sequence further contains the following mutated amino acid residues located at positions 570 and 860 in said adenylate cyclase: E570Q and K860R, or
d) the amino acid sequence of the adenylate cyclase (CyaA) of *Bordetella bronchiseptica* wherein the following mutations have been performed:
  (i) the substitution of the glutamic acid residue at position 569 by a glutamine residue (E569Q) or by a conservative amino acid residue, and
  (ii) the substitution of the lysine residue at position 859 by an arginine residue (K859R) or by a conservative amino acid residue, or;
e) an amino acid sequence of a fragment of the adenylate cyclase of *Bordetella bronchiseptica*, which fragment has the capacity of the CyaA protein of *Bordetella pertussis* to bind to a target cell and the capacity to translocate its N-terminal adenylate cyclase enzyme domain or part thereof into said cell, wherein said fragment further contains the following mutated amino acid residues located at positions 569 and 859 in said adenylate cyclase: E569Q and K859R, or
f) an amino acid sequence which differs from the amino acid sequence as defined in d) or e) by one or more amino acid residue substitutions and/or insertions and which has the capacity of the CyaA protein of *Bordetella Pertussis* to bind to a target cell and the capacity to translocate its N-terminal adenylate cyclase enzyme domain or part thereof into said cell, wherein said amino acid sequence further contains the following mutated amino acid residues located at positions 569 and 859 in said adenylate cyclase: E569Q and K859R.

For the purpose of the invention, the N-terminal domain of the described fragment is the amino acid sequence of the fragment which includes the contiguous amino acid residues of the N-terminal part of the native CyaA protein, e.g. the N-terminal part of the fragment is all or part of the contiguous residues forming the sequence of 400 amino acid residues of the N-terminal domain of the *Bordetella pertussis* CyaA protein.

Herein, "E570Q" encompasses substitution of the glutamic acid residue at position 570 of native CyaA of *Bordetella pertussis, Bordetella parapertussis* or *Bordetella hinzii* by a glutamine residue or by another conservative residue, in particular a residue whose side chain size and hydrophilic nature is close to that of glutamic acid. The glutamic acid residue at position 570 is preferably substituted by an amino acid residue selected from Gln, Asn, Met, Thr, Ser, Gly, Arg, Lys, Val, Leu, Cys, Ile, Asp.

Herein, "K860R" encompasses substitution of the lysine residue at position 860 of native CyaA of *Bordetella pertussis, Bordetella parapertussis* or *Bordetella hinzii* by an arginine residue or by another conservative residue, in particular a residue whose side chain size and hydrophilic nature is close to that of lysine. The lysine residue at position 860 is preferably substituted by an amino acid residue selected from Arg, Asn, Gln, Met, Thr, Ser, Gly, Val, Leu, Cys, Ile.

Herein, "E569Q" encompasses substitution of the glutamic acid residue at position 569 of native CyaA of *Bordetella bronchiseptica* by a glutamine residue or by another conservative residue, in particular a residue whose side chain size and hydrophilic nature is close to that of glutamic acid. The glutamic acid residue at position 569 is preferably substituted by an amino acid residue selected from Gln, Asn, Met, Thr, Ser, Gly, Arg, Lys, Val, Leu, Cys, Ile, Asp.

Herein, "K859R" encompasses substitution of the lysine residue at position 859 of native CyaA of *Bordetella bronchiseptica* by an arginine residue or by another conservative residue, in particular a residue whose side chain size and hydrophilic nature is close to that of lysine. The lysine residue at position 859 is preferably substituted by an amino acid residue selected from Arg, Asn, Gln, Met, Thr, Ser, Gly, Val, Leu, Cys, Ile.

In the embodiments described hereafter, the mutant *Bordetella pertussis* CyaA proteins or protein fragments carrying the "E570Q" and "K860R" substitutions may be replaced by mutant *Bordetella parapertussis* or *Bordetella hinzii* CyaA proteins or protein fragments carrying the equivalent "E570Q" and "K860R" substitutions, or by mutant *Bordetella bronchiseptica* CyaA proteins or protein fragment carrying the equivalent "E569Q" and "K859R" substitutions.

The native CyaA of *Bordetella pertussis* has also been described as an amino acid sequence and a nucleotide sequence by Glaser, P. et al, 1988, Molecular Microbiology 2(1), 19-30. This sequence is referred to as SEQ ID N°1 as illustrated in FIG. 6. Accordingly, when amino acid residues or sequences or nucleotides or nucleotide sequences of the CyaA protein of *B. pertussis*, are cited in the present invention their positions are given with respect to the sequences disclosed in said publication of Glaser et al. 1988.

In an embodiment of the present invention the amino sequence of the *Bordetella pertussis* adenylate cyclase is the sequence disclosed as SEQ ID N°1.

When reference is made to SEQ ID N°1 or to SEQ ID N°2 herein, it is especially pointed out that, unless it is technically not relevant, the disclosed features would similarly apply to a sequence modified by insertion of residues in SEQ ID N°1 or SEQ ID N°2 in order to detoxify the CyaA protein. In such a case, the numbering of the amino acid residues should be adapted (especially insofar as positions 570 and 860 of the native sequence are concerned).

Advantageously, the CyaA protein or a fragment thereof is a protein or a fragment thereof, which is the result of the co-expression in a cell, especially in a recombinant cell, of both cyaA and cyaC genes. It has been indeed shown that in order to have invasive properties for target cells, CyaA has to undergo post-translational modifications which are enabled by the expression of both cyaA and cyaC genes (WO 93/21324).

In a particular embodiment of the invention, the CyaA protein is a bacterial protein. In a preferred embodiment, CyaA protein is derived from a *Bordetella* species.

Among *Bordetella* species of interest, according to the invention, one of them is *Bordetella pertussis*. Other *Bordetella* strains of interest are those of *Bordetella parapertussis, Bordetella hinzii* or *Bordetella bronchiseptica*. The sequence of CyaA protein of *B. parapertussis* has been disclosed especially under accession number NC 002928.3 (as a sequence of 1740 amino acids) and in Parkhill J. et al (Nat. Genet. DOI, 10 (2003)), for *B. hinzii* in Donato G. M. et al. (J. Bacteriol. 2005 November, 187(22):7579-88) and for *B. bronchiseptica* in Betsou F. et al (Gene 1995, Aug. 30; 162(1): 165-6). The sequence of *Bordetella parapertussis* has been disclosed especially under accession number CAB76450, referred to herein as SEQ ID N°7 as illustrated in FIG. 14. The sequence of *Bordetella hinzii* has been disclosed especially under accession number AAY57201, referred to herein as SEQ ID N°8 as illustrated in FIG. 15. The sequence of *Bordetella bronchiseptica* has been disclosed especially under accession number CAA85481, referred to herein as SEQ ID N°9 as illustrated in FIG. 16. Accordingly, when amino acid residues or sequences of the CyaA protein of *Bordetella parapertussis, Bordetella hinzii* or *Bordetella bronchiseptica*, are cited in the present invention their positions are given with respect to the sequences disclosed in SEQ ID N°7, 8 and 9 respectively.

The expression "polypeptide mutant of the adenylate cyclase protein" excludes the native adenylate cyclase as expressed by *Bordetella*. As stated above, it is characterised by a primary difference with the native protein, lying in the combined substitution of two specific amino acid residues. It may be further modified with respect to said native protein and it may especially be a fragment of the thus mutated protein, such as for example a truncated variant of said mutated protein, wherein residues at either or both terminal ends are deleted. In particular residues at the C-terminal end may be deleted to the extent that it does not affect the recognition and binding site for the CD11b/CD18 cell receptor. Alternatively or in addition residues may be deleted at the N-terminal end provided that it does not affect the translocation ability of the obtained mutant polypeptide. It may also be a fragment obtained after internal deletions of one or more residues of the native mutated CyaA protein.

Where the invention relates to a polypeptide mutant which is a fragment as stated herein, said fragment which necessarily comprises the mutated residues E570Q and K860R (when reference is made to the amino sequence of the CyaA protein of *Bordetella pertussis*) also retains the ability of the mutated full-length CyaA to bind cells and to translocate its N-terminal domain into the cytosol of target cells, especially of CD11b/CD18 expressing cells.

The invention provides thus mutant polypeptides suitable for use in the design of means for the delivery of one or more molecules into a cell, especially a target cell expressing the CD11b/CD18 receptor.

In particular the invention provides mutant polypeptides of a CyaA protein, where said protein is either derived from the CyaA toxin or is preferably derived from a toxoid thereof, especially a CyaA/AC⁻ toxoid. The mutant polypeptides are capable of binding to a cell, especially to a target cell, especially a target cell expressing the CD11b/CD18 receptor, are capable of translocating their N-terminal domain or the molecule inserted in said domain or grafted on it into the cell and their pore-forming activity is totally or partially suppressed as compared to that of the CyaA toxin or toxoid.

The capacity of the mutant polypeptide to target CD11b/CD18 cells can be assayed especially according to the methods disclosed in EP 03291486.3 and El-Azami-El-Idrissi M. et al, J. Biol. Chem., 278(40)38514-21 or in WO 02/22169. Furthermore, the capacity of the mutant polypeptide to translocate the epitope(s) or polypeptide(s) containing said epitope(s) into the cytosol of target cell can be assayed by applying the method described in WO 02/22169.

Total or partial suppression of the CyaA toxin or toxoid pore-forming activity, or cell-permeabilizing capacity, is to be understood as the total or partial suppression of the ability to form pores, in particular cation selective pores of an estimated diameter of 0.6 to 0.8 nm, which permeabilize a cellular membrane and eventually provoke colloid-osmotic cell lysis. The pore-forming activity can be measured using the single whole cell patch-clamp experiment as described in examples.

The pore-forming activity of the CyaA toxin contributes to its overall cytolytic or haemolytic activity on cells. Indeed in the context of the present invention, the overall cytolytic or haemolytic activity of CyaA (or its "overall cytotoxic activity") is to be understood as the resultant of at least the adenylate cyclase and pore-forming activities of the CyaA toxin. Thus total or partial suppression of the CyaA toxin pore-forming activity allows at least a partial suppression of its cytolytic activity.

In a preferred embodiment, the overall cytolytic activity of the polypeptide according to the invention, in particular on cells which express the CD11b/CD18 receptor, is totally or partially reduced as compared to that of the *Bordetella pertussis* CyaA toxin. The cytolytic activity of the inventive polypeptide can be determined by measuring the amount of hemoglobulin (for erythrocytes) or of lactate dehydrogenase (for monocytes) released by the cells when incubated with the tested polypeptide as described in examples.

Figure 2:
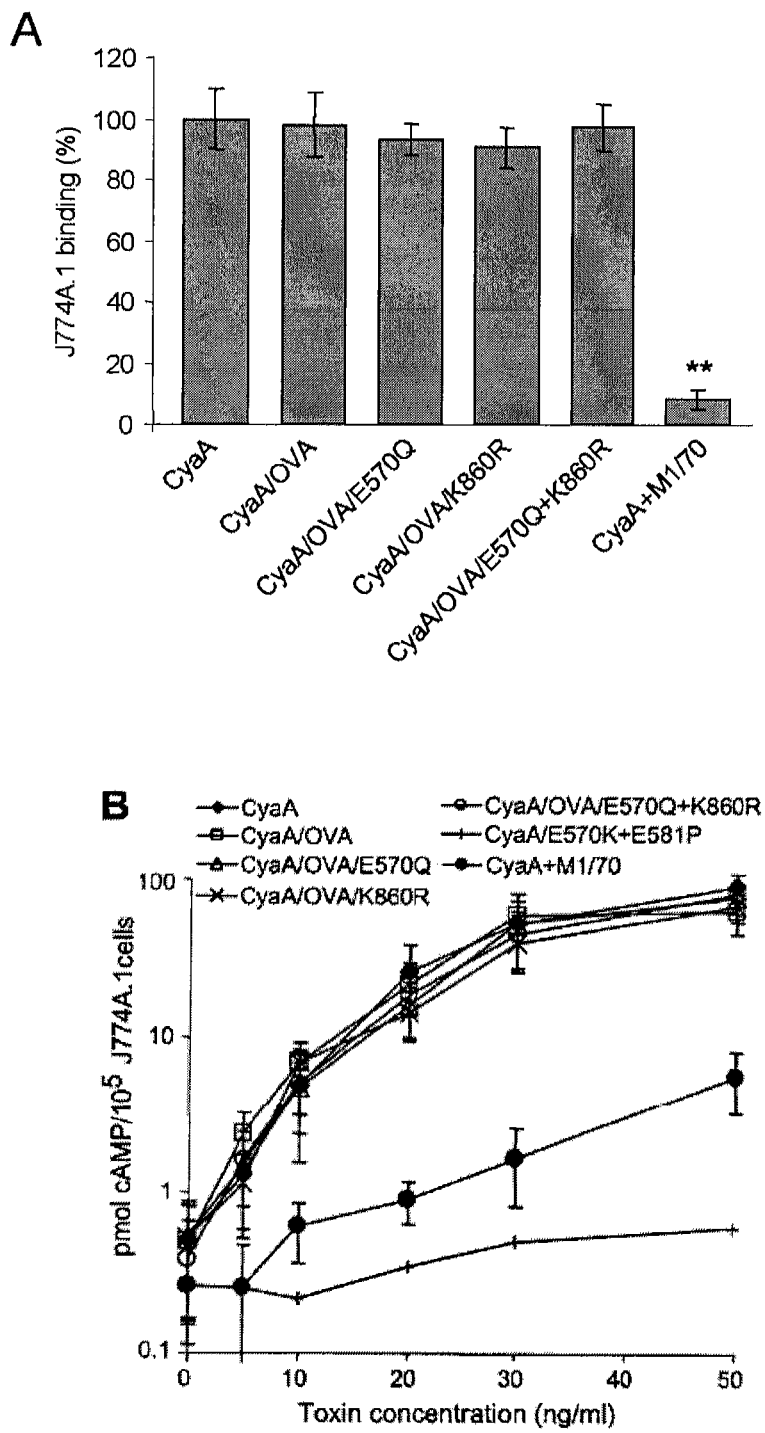
Figure 2:
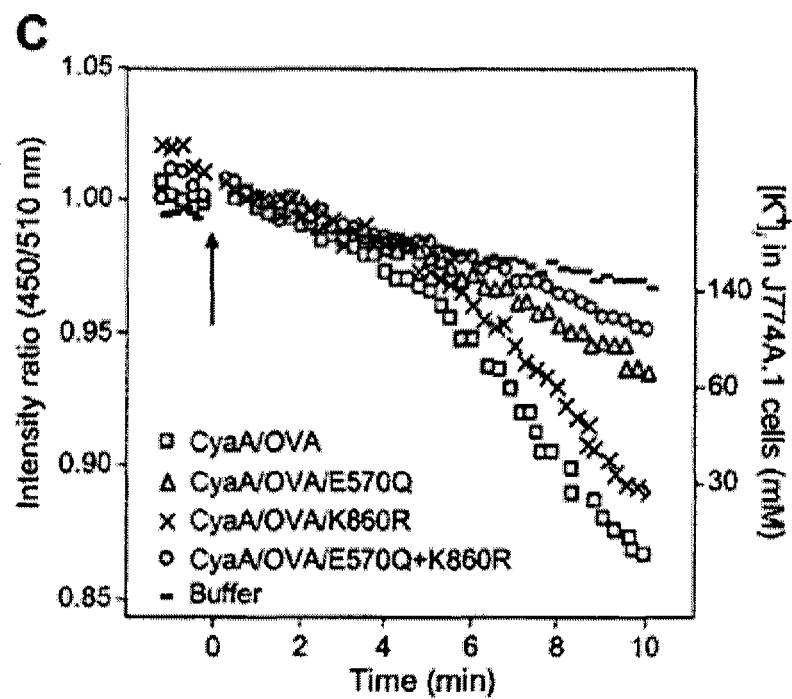

In a preferred embodiment, the overall cytolytic activity of the polypeptide according to the invention on cells which express the CD11b/CD18 receptor is at least 75% lower, preferably still at least 80%, 85%, 90% or 95% lower, than that the *Bordetella pertussis* CyaA toxin, or than that of a *Bordetella pertussis* CyaA protein whose adenylate cyclase activity is partly or totally suppressed (or "CyaA toxoid"). In a particularly preferred embodiment, the overall cytolytic activity of the polypeptide according to the invention on cells which express the CD11b/CD18 receptor is at least 75% lower, preferably still at least 80% or 85% lower, than that the *Bordetella pertussis* CyaA toxoid whose amino acid sequence is shown in FIG. 2 (SEQ ID N°2).

In a preferred embodiment, the invention relates to a polypeptide which is a mutant of an adenylate cyclase and whose amino acid sequence comprises or consists of an amino acid sequence (i) which is mutated with respect to the amino acid sequence disclosed in SEQ ID N°1 said mutations comprising at least the substitutions E570Q and K860R or (ii) which is a fragment of the CyaA protein having said amino acid sequence disclosed as SEQ ID N°1, to the extent that said fragment has an amino acid sequence including substitutions E570Q and K860R and wherein the polypeptide is capable of binding to a target cell and of translocating its N-terminal domain into the cell.

In a particular embodiment of the present invention, the fragment including a substitution of the glutamic acid residue at position 570 of SEQ ID N°1 by a glutamine residue (referred to as "E570Q"), and the substitution of the lysine residue at position 860 of SEQ ID N°1 by an arginine residue (referred to as "K860R") encompasses at least the amino acid sequence of the CyaA protein starting with the first N-terminal residue or from one of the amino acid residues comprised between the positions 1 and 400, preferably between the positions 1 and 380 and extending up to the residues forming the recognition and binding site for the CD11b/CD18 cell receptor and said fragment contains residues corresponding to the mutated E570Q and K860R residues or consists of said amino acid sequence. In a particular embodiment, the fragment including the E570Q and K860R substitutions does not comprise the amino acid sequence running from the amino acid at position 1 of SEQ ID N°1 to the amino acid at position 372 of SEQ ID N°1.

In a preferred embodiment the fragment which is thus prepared has essentially lost the adenyl cyclase enzyme activity (AC activity)

In a preferred embodiment, the mutant polypeptide of the invention is produced by co-expression in a recombinant cell of a mutated gene encoding the E570Q and R860R mutated CyaA amino acid sequence and of the cyaC gene, followed by recovery of the selected expressed fragment of mutant CyaA.

Preferably, the mutant polypeptide of the invention has a lysine residue which corresponds to the lysine residue at position 983 of the CyaA amino acid sequence as set forth in SEQ ID N°1 and which is acylated, in particular which is palmytoylated or palmitoleilated.

Alternatively, the mutant polypeptide of the invention has a lysine residue which corresponds to the lysine residue at position 983 of the CyaA amino acid sequence as set forth in SEQ ID N°1 which is not acylated.

In a specific embodiment, the mutant polypeptide of the invention has an amino acid sequence derived from the CyaA amino acid sequence disclosed in SEQ ID N°1 by mutation of residues resulting in E570Q and K860R and has an amino acid sequence which shares at least 50%, preferably at least 60%, 70%, 75%, 80%, 85%, 90%, 95% or 99% identity with the sequence set forth in SEQ ID N°1.

In another specific embodiment, the mutant polypeptide of the invention has an amino acid sequence which differs from the CyaA amino acid sequence as set forth in SEQ ID N°1 by mutation of residues resulting in E570Q and K860R and by further mutations resulting in 1 to 500, in particular, 1 to 400, 1 to 300, 1 to 200, 1 to 100, 1 to 50, 1 to 40, 1 to 30, 1 to 25, 1 to 20, 1 to 15, 1 to 10 or 1 to 5 amino acid residue substitutions, deletions, and/or insertions including the E570Q and K860R substitutions.

In a specific embodiment, the mutant polypeptide of the invention does not carry any amino acid residue substitutions, deletions, and/or insertions as compared to the *Bordetella pertussis* CyaA amino acid sequence other than the E570Q and K860R substitutions. In a specific embodiment, the mutant polypeptide has amino acid sequence of SEQ ID N°2 as illustrated in FIG. 7. In another specific embodiment, the only further amino acid substitutions, deletions, and/or insertions as compared to the amino acid sequence of SEQ ID N°2 consist in amino acid substitutions, deletions, and/or insertions which totally or partially suppress the adenyl cyclase enzymatic activity of the CyaA protein, such as in particular the insertion of a dipeptide, for example an "LQ" or "GS" dipeptide between the amino acids at positions 188 and 189.

In a particular embodiment, the mutant polypeptide of the invention differs from the CyaA amino acid sequence as set forth in SEQ ID N°1 by 1, 2, 3, 4, 5, 6, 7, 8, 9 or 10 amino acid residue substitutions, deletions, and/or insertions in addition to the E570Q and K860R substitutions.

In a particular embodiment, in addition to the E570Q and K860R substitutions, the leucine residue at position 247 of the native CyaA protein of *Bordetella pertussis* is substituted by a glutamine residue (L247Q) or by another amino acid residue in particular a conservative amino acid residue.

A mutant polypeptide of the invention which is a fragment as disclosed herein of the amino acid sequence disclosed in SEQ ID N°1 is to be understood as a sequence which comprises one or more fragments having at least about 350 amino acid residues and up to about 1705 amino acid residues of the SEQ ID N°1 amino acid sequence, in particular fragments comprising a stretch of at least 400, 500, 600, 700, 800, 900, 1000, 1100, 1200, 1300, 1400, 1500, 1600 amino acid residues of SEQ ID N°1, encompassing residues E570Q and K860R. A mutant polypeptide of the invention can also be defined as a fragment of the amino acid sequence disclosed in SEQ ID N°2 which comprises one or more fragments having at least about 350 amino acid residues and up to about 1705 amino acid residues of the SEQ ID N°2 amino acid sequence, in particular fragments comprising a stretch of at least 400, 500, 600, 700, 800, 900, 1000, 1100, 1200, 1300, 1400, 1500, 1600 amino acid residues of SEQ ID N°2, encompassing residues 570 and 860. Said fragments preferably retain the capacity of binding to the CD11b/CD18 cell receptor and the ability to translocate their N-terminal domain into target cells. Preferably, the mutant polypeptide of the invention which is such a fragment which has a stretch of amino acids comprising amino acid residues 570 as E570Q to 860 as K860R or 1 to 860, or 2 to 860 of SEQ ID N°1 to the extent that the E570Q and K860R mutations are observed with respect to the original SEQ ID N°1.

In a preferred embodiment, the fragment further comprises amino acid residues 1166 to 1281 or amino acid residues 1208 to 1243 of the CyaA amino acid sequence as set forth in SEQ ID N°1 of CyaA protein for interaction with CD11b/CD18 target cells.

A particular fragment thus encompasses all or part of the C-terminal part of the native protein which part is responsible for the binding of the polypeptide of the invention to target cell membrane and/or CD11b/CD18 receptor, and for the subsequent delivery of the N-terminal domain of the polypeptide into the cell cytosol. A particular polypeptide of the invention is the fragment of CyaA protein which contains amino acid residues 373 to 1706 of CyaA protein especially of the SEQ ID N°1, to the extent that residues 570 and 860 are mutated as E570Q and K860R.

In another preferred embodiment, the mutant polypeptide which is such a fragment comprises:
a) a first amino acid sequence which corresponds to a stretch of at least 100 contiguous amino acid residues from SEQ ID N°1 comprising amino acid residues 570 as E570Q, and further including 0, 1, 2, 3, 4 or 5 deletions, substitutions or insertions as compared to SEQ ID N°1 and
b) a second amino acid sequence which corresponds to a stretch of at least 100 contiguous amino acid residues from SEQ ID N°1 comprising amino acid residues 860 as K860R, and further including 0, 1, 2, 3, 4 or 5 deletions, substitutions or insertions as compared to SEQ ID N°1 and preferably,
c) a third amino acid sequence comprising amino acid residues 1166 to 1281 or amino acid residues 1208 to 1243 of the CyaA amino acid sequence as set forth in SEQ ID N°1 of CyaA protein for interaction with CD11b/CD18 target cells.

Another particular polypeptide of the invention is a fragment which is one which corresponds to the E570Q and K860R mutated CyaA protein wherein amino acid residues 225 to 234 have been deleted, thus providing a fragment containing residues 1 to 224 and 235 to 1706 of the mutated protein.

In a particularly preferred embodiment, the polypeptide fragment according to the invention binds to a cell which expresses the CD11b/CD18 receptor as a result of specific binding to said receptor.

In a preferred embodiment, adenylate cyclase activity of the polypeptide in a cell is partly or totally suppressed as compared to that of the *Bordetella pertussis* CyaA toxin. As stated above, the expression "CyaA protein" relates either to the toxin form or preferably to the toxoid form of the protein. Accordingly each embodiment of the invention relating to the polypeptide which is a mutant of the CyaA protein applies to each of the toxin or toxoid form of the protein.

Total or partial suppression of CyaA adenylate cyclase or enzymatic activity is to be understood as the total or partial suppression of the ability to convert ATP into cAMP in a cellular environment as compared to that of a CyaA toxin produced by co-expression of the cyaA and cyaC genes in a cell. The ability to convert ATP into cAMP can be determined by measuring the level of intracellular cAMP as described in the examples.

Such total or partial suppression can be obtained as a result of genetic inactivation, for example by introduction of a short amino acid sequence sequence, comprising for example from one to ten amino acids, in particular a dipeptide in a site of the amino acid sequence of CyaA which is part of the catalytic site, i.e. in a site located within the first 400 amino acids (AC domain) of SEQ ID N°1 or by deletion or substitution of a part of the CyaA amino acid sequence as set forth in SEQ ID N°1 which is essential for enzymatic activity. In a preferred embodiment, total or partial suppression of the CyaA enzymatic activity is obtained by insertion of a dipeptide, for example an "LQ" or "GS" dipeptide, between the amino acids at position 188 and 189 of the CyaA sequence as set forth in SEQ ID N°1. This can be achieved by inserting an oligonucleotide, such as "CTG CAG" or "CGATCC", at the EcoRV site at position 564 of the coding phase of the cyaA gene. See Ladant et al., 1992. Alternatively, total or partial suppression of the enzymatic activity can also be obtained by directed mutagenesis, for example, by replacing the lysine residue at position 58 or 65 of the native CyaA *Bordetella pertussis* protein (Glaser et al., 1989) by a Gln residue.

The polypeptide according to the invention can also be defined as a polypeptide which may be obtained from a CyaA polypeptide having an amino acid sequence according to SEQ ID N°1, 7, 8 or 9, by:
a) substituting the glutamic acid residue at position 570 of SEQ ID N°1, 7, 8 or at position 569 of SEQ ID N°9 by a glutamine residue or by a conservative amino acid residue,
b) substituting the lysine residue at position 860 of SEQ ID N°1, 7, 8 or at position 859 of SEQ ID N°9 by an arginine residue or by a conservative amino acid residue, and
c) optionally, carrying out one or more amino acid residue substitutions, insertions and/or deletions at locations other than the locations recited in a) and b), provided that the polypeptide thus obtained has the capacity of the CyaA protein of *Bordetella pertussis* to bind to a target cell and translocate its N-terminal adenylate cyclase enzyme domain or part thereof into said cell.

Preferably, in step a), the glutamic acid residue is substituted by an amino acid residue selected from Gln, Asn, Met, Thr, Ser, Gly, Arg, Lys, Val, Leu, Cys, Ile, Asp, most preferably by Gln. Preferably, in step b), the lysine residue is substituted by an amino acid residue selected from Arg, Asn, Gln, Met, Thr, Ser, Gly, Val, Leu, Cys, Ile, most preferably by Arg.

In a specific embodiment, no further amino acid residue substitutions, insertions and/or deletions are carried out in step c).

In particular, step c) may comprise truncation of either or both terminal ends. In particular, residues at the C-terminal end may be deleted to the extent that it does not affect the recognition and binding site for the CD11b/CD18 cell receptor. Alternatively or in addition, residues may be deleted at the N-terminal end provided that it does not affect the translocation ability of the obtained mutant polypeptide. Internal deletions of one or more residues of the native CyaA protein located at positions other than those recited in steps a) and b) may also be performed. In a particular embodiment, step c) comprises the deletion of up to 380 or up to 400 amino acids in the N-terminal amino acid sequence of the CyaA polypeptide, preferably the deletion of the stretch of amino acids running from the amino acid at position 1 of SEQ ID N°1, 7, 8 or 9 to the amino acid at position 372 of SEQ ID N°1, 7, 8 or 9.

Preferably, after performing step c), the obtained polypeptide encompasses all or part of the C-terminal part of the native protein which part is responsible for the binding of the polypeptide of the invention to the membrane of the target cell and/or CD11b/CD18 receptor, and for the subsequent delivery of the N-terminal domain of the polypeptide into the cell cytosol. In a particular embodiment, in step c), amino acid residues 373 to 1706 of SEQ ID N°1, 7 or 8, or amino acid residues 373 to 1705 of SEQ ID N°9 are not deleted. In a preferred embodiment, in step c), amino acid residues 1208 to 1243 of SEQ ID N°1, 7 or 8, or amino acid residues 1207 to 1242 of SEQ ID N°9 are not deleted.

In a preferred embodiment, step c) comprises amino acid substitutions, deletions, and/or insertions which totally or partially suppress the adenyl cyclase enzymatic activity of the CyaA protein. Such total or partial suppression can be obtained by introduction of a short amino acid sequence, comprising for example from one to ten amino acids, in particular a dipeptide in a site located within the first 400 amino acids (AC domain) of SEQ ID N°1, 7, 8 or 9 or by deletion or substitution of a part of the CyaA amino acid sequence as set forth in SEQ ID N°1, 7, 8 or 9 which is essential for enzymatic activity. In a preferred embodiment, total or partial suppression of the CyaA enzymatic activity is obtained by insertion of a dipeptide, for example an "LQ" or "GS" dipeptide, between the amino acids at positions 188 and 189 of the CyaA sequence as set forth in SEQ ID N°1, 7, 8 or 9. Alternatively, total or partial suppression of the enzymatic activity can also be obtained by directed mutagenesis, for example, by replacing the lysine residue at position 58 or 65 of the native CyaA *Bordetella pertussis* protein (Glaser et al., 1989) by a Gln residue.

Preferably, in step c) the lysine residue at position 983 of the CyaA amino acid sequence as set forth in SEQ ID N°1, 7, 8 or at position 982 in SEQ ID N°9 is neither substituted nor deleted. In one embodiment, this lysine residue is acylated, in particular it is palmytoylated or palmitoleilated. Alternatively, this lysine residue is not acylated.

Preferably, after performing step c), the obtained polypeptide has an amino acid sequence which shares at least 50%, preferably at least 60%, 70%, 75%, 80%, 85%, 90%, 95% or 99% identity with the sequence set forth in SEQ ID N°1, 7, 8 or 9.

Preferably still, after performing step c), the obtained polypeptide has an amino acid sequence which differs from the sequence set forth in SEQ ID N°1, 7, 8 or 9 by the amino acid residue substitutions resulting from steps a) and b), and by 1 to 500, in particular, 1 to 400, 1 to 300, 1 to 200, 1 to 100, 1 to 50, 1 to 40, 1 to 30, 1 to 25, 1 to 20, 1 to 15, 1 to 10 or 1 to 5 further amino acid residue substitutions, deletions, and/or insertions. In a particular embodiment, after performing step c), the obtained polypeptide differs from the CyaA amino acid sequence as set forth in SEQ ID N°1, 7, 8 or 9 by 1, 2, 3, 4, 5, 6, 7, 8, 9 or 10 amino acid residue substitutions, deletions, and/or insertions in addition to the substitutions carried out in steps a) and b).

The invention is also directed to a polypeptide derivative comprising or consisting of the mutant polypeptide according to the invention which is further combined with one or more molecules of interest. In a preferred embodiment, a molecule of interest is a biologically active molecule either when taken alone or when combined to the polypeptide of the invention. Said molecules may especially be of prophylactic value or therapeutic value i.e., may have a prophylactic or a therapeutic activity, or may enhance a prophylactic or therapeutic activity.

In specific embodiments, the molecules of interest are selected in the group comprising: peptides, glycopeptides, lipopeptides, polysaccharides, oligosaccharides, nucleic acids, lipids and chemicals.

In a specific embodiment, the one or more molecules of interest are polypeptidic molecules or contain polypeptidic molecules. Their amino acid sequence may comprise 2 to 1000, preferably 5-800, 5 to 500, 5 to 200, 5 to 100, 8 to 50, 5 to 25, 5 to 20 or 8 to 16, or 300-600, 400-500, amino acid residues.

In a preferred embodiment, the one or more molecules of interest are heterologous amino acid sequences suitable for eliciting an immune response (also referred to as "heterologous antigens"), in particular amino acid sequences which comprise or consist of an epitope, including antigens. As used herein, the term "heterologous" refers to an antigen other than the mutant polypeptide which is used in the vector itself. As used herein, the term "epitope" refers to a heterologous molecule and especially a heterologous peptide that can elicit an immune response, when presented to the immune system of a host. In particular, such an epitope can comprise or consist of a stretch of 8, 9, 10, 11, 12, 13, 14, 15 or 16 amino acid residues. It may alternatively consist in a full-length antigen or consist in antigen(s) fragment(s).

In a specific embodiment, a polypeptide derivative according to the invention can be encoded by a plasmid which corresponds to the OVA-QR-AC⁻ plasmid deposited under accession number CNCM I-4137 (FIG. 12) in which the DNA sequence encoding the "OVA" antigenic sequence is replaced by a DNA sequence encoding an antigenic sequence comprising one or more epitopes.

The polypeptidic molecule suitable for eliciting an immune response is especially one eliciting a T-cell immune response, including as an example a CTL response. The polypeptidic molecule suitable for eliciting an immune response can also be one eliciting a B-cell immune response.

In specific embodiments, the heterologous antigen is selected from the group consisting of an antigen of a bacterial pathogen, a tumoral cell antigen, a viral antigen, a retroviral antigen, a fungus antigen or a parasite cell antigen.

A molecule of interest can be especially an antigen selected from the group consisting of: a Chlamidia antigen, a Mycoplasma antigen, a hepatitis virus antigen, a poliovirus antigen, an HIV virus antigen, an influenza virus antigen, a choriomeningitis virus antigen, a tumor antigen, or a part of any of these antigens which comprises at least an epitope.

In a preferred embodiment of the polypeptide derivative of the invention, the amino acid sequence of each of said molecule(s) suitable for eliciting an immune response comprises or consists of an amino acid sequence of a Chlamidia antigen, a Mycoplasma antigen, a hepatitis virus antigen, a poliovirus antigen, an HIV virus antigen, an influenza virus antigen, a choriomeningitis virus sequence, a tumor antigen, or comprises or consist of a part of an amino acid sequence of any these antigens which comprises at least one epitope.

In a particularly preferred embodiment, the molecule of interest is a tumor associated antigen (TAA). Tumor-associated antigens have been characterized for a number of tumors such as for example: Melanoma, especially metastatic melanoma; Lung carcinoma; Head & neck carcinoma; cervical carcinoma, Esophageal carcinoma; Bladder carcinoma, especially infiltrating Bladder carcinoma; Prostate carcinoma; Breast carcinoma; Colorectal carcinoma; Renal cell carcinoma; Sarcoma; Leukemia; Myeloma. For these various histological types of cancers, it has been shown that antigenic peptides are specifically expressed on tumor samples and are recognized by T cells, especially by $CD8^+$ T cells or $CD4^+$ T cells.

A review of peptides found as tumor-associated antigens in these types of tumors is made by Van der Bruggen P. et al (Immunological Reviews, 2002, vol 188:51-64). Especially, the disclosure of the peptides contained in table 3 of said review is referred to herein as providing examples of such tumor-associated antigens and said table 3 is incorporated by reference to the present application.

The following antigens are cited as examples of tumor-associated antigens recognized by T cells, according to the publication of Kawakami Y. et al (Cancer Sci, October 2004, vol. 95, no. 10, p 784-791) that also provides methods for screening these antigens or further one: antigens shared by various cancers, including MAGE (especially in Melanoma), NY-ESO-1, Her2/neu, WT1, Survivin, hTERT, CEA, AFP, SART3, GnT-V, antigens specific for some particular cancers such as βbeta-catenin, CDK4, MART-2, MUM3, gp100, MART-1, tyrosinase for Melanoma; bcr-abl, TEL-AML1 for Leukemia; PSA, PAP, PSM, PSMA for prostate cancer; Proteinase 3 for myelogenous leukemia; MUC-1 for breast, ovarian or pancreas cancers; EBV-EBNA, HTLV-1 tax for lymphoma, ATL or cervical cancer; mutated HLA-A2 for Renal cell cancer; HA1 for leukemia/lymphoma. Tumor-associated antigens in animals have also been described such as Cycline D1 and Cycline D2 in tumors affecting cats or dogs.

Tumor-associated antigens recognized by T cells have also been disclosed in Novellino L. et al (Immunol Immunother 2004, 54:187-207).

More generally, TAA of interest in the present invention are those corresponding to mutated antigens, or to antigens that are overexpressed on tumor cells, to shared antigens, tissue-specific differenciation antigens or to viral antigens.

In a particular embodiment of the invention, the tumor-associated antigen is an antigen of papillomavirus (HPV) or is tyrosinase.

According to another particular embodiment of the invention, the amino acid sequences of the polypeptidic molecules which comprise or consist of an epitope have been modified with respect to their native amino acid sequence, for example in order to decrease the number of negatively charged amino acid residues within the sequence. Such a modification can be obtained by removing some of these negatively charged amino acid residues or also by adding some positively charged amino acid residues, especially as flanking residues of the epitopes. Polypeptides thus comprising less negatively charged residues might favour the translocation of the catalytic domain of the polypeptide derivative of the invention in the cytosol of target cells.

The amino acid sequences of the polypeptidic molecules which comprise or consist of an epitope or an antigen can also be designed in such a way that they are unfolded when they are inserted in the polypeptide derivative of the invention, which improves efficiency of the internalization of the molecule(s) of interest according to the invention into the target cells. Such unfolding in polypeptides which undergo folding as a consequence of their amino acid content, can be obtained for instance, by removing or substituting cystein residues in order to avoid formation of disulfide bonds that may be involved in folding of polypeptides. In some cases, it is possible to prevent folding of the polypeptides by preparing them in the presence of reducing agents to enable avoiding in vivo refolding.

In a particular embodiment, the amino acid sequences, especially the antigen, can comprise or consist of cryptic epitopes.

The inventors have indeed determined that polypeptide derivative constructs, which comprise (i) a polypeptide of the invention which is a mutant of a CyaA protein (polypeptide mutant) according to the definitions disclosed herein and (ii) a polypeptidic molecule having an amino acid sequence bearing one or several antigenic fragments of one or several antigens, enable cryptic epitopes of said antigens to become immunogenic as a result of their presentation in the constructs. Especially, said constructs involving mutant polypeptides as defined in the present invention comprising polypeptidic molecule(s) derived from antigens of interest for especially prophylactic or therapeutic applications, including immunotherapeutic vaccination, purposes are processed in target cells where the polypeptidic molecule(s) is allowed to be internalized as a result of the translocation of the N-terminal domain of the mutant polypeptide. Such processing enables epitopes presentation through the class I MHC molecules of the target cells, and said epitopes can comprise cryptic epitopes of the antigen which are allowed to become immunogenic and in particular to raise a T-cell response in a host, especially a CTL response.

The invention thus also relates to a polypeptide derivative, in particular to a recombinant protein comprising one or several polypeptidic molecules having an amino acid sequence bearing one or several epitopes of one or several antigens, or bearing said antigen(s) said amino acid sequence(s) of said polypeptidic molecule(s) being inserted in the same or in different sites, especially in different permissive sites of a mutant polypeptide according to the invention, said recombinant protein retaining the property of the CyaA toxin to target antigen presenting cells (APC), wherein at least one of said epitope(s) is a subdominant cryptic T-cell epitope and wherein said polypeptide derivative, especially said recombinant protein, is capable of eliciting an antigen-specific response against said polypeptidic molecule(s).

In a specific embodiment of the polypeptide derivative according to the invention, the one or more amino acid sequences are inserted into one or more sites, especially permissive sites.

For the present invention, a "permissive site" is a site of the sequence of the CyaA protein where a polypeptide can be inserted without substantially affecting the desired functional properties of the CyaA protein especially without substantially affecting the targeting of cells, particularly the targeting of antigen presenting cells (APC) by CyaA, including without substantially affecting the specific binding to the CD11b/CD18 receptor and advantageously without substantially affecting the domains of the protein involved in the process of translocation of the CyaA N-terminal domain into a target cell.

Methods to select for permissive sites are presented for example in WO93/21324, in Ladant et al., 1992, and in Osicka et al., 2000 (Infection and Immunity, 2000, 68(1):247-256). In particular, a methodology using a double selection (resistance to an antibiotic and colorimetric test on dishes by α-complementation) enables to identify readily oligonucleotides insertions (which preserve the reading frame) in the portion of the gene coding for the N-terminal catalytic domain of the toxin. The functional consequences of these mutations on the catalytic activity of the toxin may be readily analysed, both genetically (functional complementation of an E. coli cya⁻ strain) and biochemically (characterization of the stability of the modified adenylcyclases, of their enzymatic activity, of their interaction with caM, etc.). This methodology has enabled a large number of mutations to be screened in order to identify the sites which are potentially advantageous for the insertion of antigenic determinants.

Permissive sites of the Bordetella pertussis adenylate cyclase allowing translocation of CyaA catalytic domain and hence translocation of amino acid sequences inserted into such permissive sites include, but are not limited to, residues 137-138 (Val-Ala), residues 224-225 (Arg-Ala), residues 228-229 (Glu-Ala), residues 235-236 (Arg-Glu), and residues 317-318 (Ser-Ala) (Sebo et al., 1995). The following additional permissive sites are also included in embodiments of the invention: residues 107-108 (Gly-His), residues 132-133 (Met-Ala), residues 232-233 (Gly-Leu), and 335-336 (Gly-Gln) and 336-337. However, other permissive sites may be used in the present invention, that can be identified for example by use of the methodology indicated above, especially sites between residues 400 and 1700 of the CyaA protein.

For other Bordetella species corresponding permissive sites can be defined by comparison of sequences and determination of corresponding residues.

According to another embodiment, the one or more amino acid sequence polypeptide can also or alternatively be inserted at one and/or the other extremities (ends) of the polypeptide of the invention, preferably at the N-terminal end of the mutant CyaA polypeptide lacking all or part of the N-terminal catalytic domain of the Bordetella pertussis CyaA protein, and more particularly lacking residues 1-373.

According to a specific embodiment, the one or more amino acid sequences suitable for eliciting an immune response, is grafted onto an amino acid residue of said polypeptide.

According to the invention, the "combination" (or insertion) of an amino acid sequence with the CyaA mutant polypeptide to provide a so-called polypeptide derivative, also referred to as a "recombinant protein" or a "hybrid protein", encompasses genetic insertion especially by available DNA technology. Alternatively, "combination" also encompasses non genetic insertion, including chemical insertion for instance covalent coupling carried out especially at one extremity of the amino acid sequence, or non covalent coupling. Non-genetic insertion can especially be of interest when the amino acid sequence to be inserted is synthetic or semi-synthetic. Methods for coupling a drug to a polypeptide are well known in the Art and comprise for example disulfide linkage by using N-pyridyl sulfonyl-activated sulfhydryl.

In particular, it is possible to graft molecules to the polypeptides of the invention by a chemical linkage or by genetic insertion for in vivo targeting to CyaA target cells, such as APC, for example CD11b/CD18 positive cells and particularly to the cytosol of said cells. Indeed, when coupling a molecule corresponding to a given CD8+ T-cell epitope to the catalytic domain of detoxified CyaA, either by means of a disulfide bond or by genetic insertion, it has been found that the engineered molecule can elicit in vivo specific CTL response, thereby showing that said CD8+ T-cell epitope is translocated into the cytosol of CD11b-expressing cells.

In a preferred embodiment of the invention, the mutant CyaA polypeptide is used in the manufacturing of a proteinaceous vector or in the preparation of a composition specifically designed to prime CD8+ cytoxic T-cell response (CTL response) when said response follows the targeting of the mutant CyaA polypeptide modified (especially recombined or conjugated) with a molecule of interest to CD11b expressing cells, followed by the translocation of the molecule of interest to the cytosol of said CD11b expressing cells, and in particular to myeloid dendritic cells. In this context, the molecule of interest is or comprises preferably an epitope or an antigen.

In another preferred embodiment of the invention, the mutant CyaA polypeptide is used in the manufacturing of the proteinaceous vector or in the preparation of a composition specifically designed to prime CD4+ cells response when said response follows the targeting of the adenylcyclase modified (especially recombined or conjugated) with a molecule of interest to CD11b expressing cells, in particular myeloid dendritic cells. In this context, the molecule of interest is or comprises preferably an epitope or an antigen.

The mutant polypeptides can also be used in the manufacturing of a proteinaceous vector for targeting of a prophylactic or a therapeutic compound to CD11b expressing cells. In this context, in one specific embodiment of the invention, the so-called molecule of interest has a prophylactic or therapeutic value and in particular is a drug. Said prophylactic or therapeutic compound and in particular said drug may be chemically or genetically coupled to the mutant polypeptide. Method for coupling a compound to a polypeptide are well known in the Art and comprise for example disulfide linkage by using N-pyridyl sulfonyl-activated sulfhydryl. In one embodiment, a molecule of interest is an anti-inflammatory compound which is, when coupled to the mutant polypeptide, specifically targeted to the surface of the cells involved of the inflammatory response, such as dentritic cells or neutrophils.

More specifically, antigen presentation for selective CD8+ cytotoxic cells priming is mainly performed by myeloïd dendritic cells.

Accordingly, in a specific embodiment, the mutant CyaA polypeptide used for the manufacturing of proteinaceous vector is a genetically modified adenylcyclase containing one or more molecule(s) chemically coupled by means of a disulfide bond to genetically inserted cysteine residue(s) located within the catalytic domain of the mutant CyaA polypeptide. Indeed, multiple molecules can be chemically coupled to the mutant CyaA polypeptide by means of a disulfide bond to different cysteine residues located at different permissive sites within the catalytic domain.

The mutant polypeptides or polypeptide derivatives according to the invention are suitable for use in therapy or prophylaxis.

By therapy or therapeutic effect it is intended any effect which is beneficial to the condition of a patient, be it curative or sufficient to limit the symptoms or the consequences of a pathological condition, including limiting the progression of a pathological condition. By therapy or therapeutic effect is also encompassed the prevention of the onset of pathological condition.

The mutant polypeptides or polypeptide derivatives according to the invention are in particular suitable to elicit a cell-mediated immune response such as a T-cell immune response or a B-cell immune response in a host in need thereof. It includes CTL and Th, especially Th1 response, including CD4+ T cell response and/or CD8+ T cell response.

The ability of a polypeptide derived from CyaA protein to elicit a cell-mediated immune response may be sufficient to prevent tumor growth in vivo or even to enable tumor regression in an animal. It may also be enhanced by activation of innate component of the immune response through TLR activation and by down activating the regulatory component of the immune response through the use of chemotherapeutic agents. The invention provides means which should enable such results to be obtained in improved safety conditions as a result of the combined mutations E570Q and K860R, which have been selected.

The present invention is thus also directed to therapeutic methods comprising administration to an animal or human patient of the mutant polypeptide or polypeptide derivative according to the invention to a patient to elicit a T-cell immune response or a B-cell immune response in a host in need thereof.

The mutant polypeptides or polypeptide derivatives according to the invention can in particular be used for the prevention or the treatment of a disease selected from neoplasia, cancers and infectious diseases selected from viral-, retroviral-, bacterial- or fungal-induced diseases. In particular, the polypeptide derivatives can be used for the treatment of HIV infections in a patient.

It is especially provided that in a particular embodiment of the invention, the CyaA mutant polypeptide or polypeptide derivative is suitable for the treatment of infiltrating or vascularized tumors versus superficial tumors or for the treatment of metastatic tumors versus primary tumors, in accordance with the acknowledged clinical criteria for the classification of tumors.

Solid tumors are especially a target for the treatment through the use of the polypeptide derivative of the invention.

Among tumors which may be candidates for the treatment with the polypeptide derivative of the invention, the following, for which tumor-associated antigens have been characterized, are described as examples:

Melanoma, especially metastatic melanoma; Lung carcinoma; Head & neck carcinoma; cervical carcinoma, Esophageal carcinoma; Bladder carcinoma, especially infiltrating Bladder carcinoma; Prostate carcinoma; Breast carcinoma; Colorectal carcinoma; Renal cell carcinoma; Sarcoma; Leukemia; Myeloma. For these various histological types of cancers, it has been shown that antigenic peptides are specifically expressed on tumor samples and are recognized by T cells, especially by CD8+ T cells or CD4+ T cells.

The invention further relates to the use of a polypeptide derivative according to the invention, for the preparation of a therapeutic composition for the treatment of a disease selected from neoplasia, cancers and infectious diseases selected from viral- or retroviral-induced diseases.

In a preferred embodiment, the polypeptide or polypeptide derivative according to the invention can be administered to the patient in combination with an adjuvant and/or in combination with another therapeutically active molecule or agent.

In the context of the present invention said "another therapeutically active molecule or agent" is one which may be beneficial to the condition of a patient to whom it is administered. It is especially an active principle suitable for use in the manufacturing of a drug. It may be a compound suitable to either, potentiate increase or modulate the effect of a therapeutically active principle.

The mutant CyaA poplypeptide or the poplypeptide derivative thereof can be administered with a therapeutically active molecule or agent, in particular one suitable for eliciting an immune response in a patient.

In particular, mutant CyaA poplypeptide or the poplypeptide derivative thereof can be administered with a therapeutically active agent suitable for modulating a cell response in a patient, in particular by lowering or blocking regulatory T cells immunosuppressive capacity.

According to a particular embodiment of the invention, such an effect on a regulatory cell response may be obtained with an agent modulating a regulatory T cell and/or modulating another cell suppressive response, such as the myeloid suppressive cells response, said agent targeting said regulatory cells, especially T cells, by depleting or inactivating these cells (such as with CD25-specific antibody, or cyclophosphamide), altering trafficking of said cells, especially regulatory T cells (such as CCL22-specific antibody) or altering differentiation and signalling of said cells (such as by blocking FOXP3 (forkhead box P3) signal).

According to a particular embodiment of the invention, the agent modulating a regulatory cell response targets suppressive molecules, especially such molecules present on APCs (such as B7-H1, B7-H4, IDO (indoleamine 2,3-dioxygenase) or arginase) or on T cells (such as CTLA4 (cytotoxic T-lymphocyte-associated antigen 4) or PD1 (programmed cell death 1)), or targets soluble immunosuppressive molecules (such as TGF beta (transforming growth factor), IL-10, VEGF (vascular endothelial growth factor), COX2 (cyclooxygenase 2)).

As examples of agents having an effect on a regulatory cell response, cytotoxic agents are proposed, that can kill regulatory T cells or other immunosuppressive cells, or that can block their activity and/or development and/or accumulation.

In a particular embodiment of the invention, the agent modulating the regulatory cell response, especially a regulatory T cell response, is a chemotherapeutic agent. Especially it is selected among chemotherapeutic agents known as anti-cancer agents and used in chemotherapy. Such agents include those helping to reduce the tumor burden, those acting by increasing sensitivity of tumor cells to treatment or those enabling killing or inactivating immune regulatory cells. The chemotherapeutic agents used within the frame of the invention thereby enhance antitumor immunity.

In a particular embodiment of the invention, the chemotherapeutic agent is an alkylating agent. Especially, it is Cyclophosphamide (CTX) (Sigma, Steinheim, Germany). Cyclophosphamide is capable of depleting or inactivating regulatory T cells.

In another particular embodiment of the invention, the chemotherapeutic agent is an intercalating agent.

In a particular embodiment, the chemotherapeutic agent is Doxorubicin (DOX) (Calbiochem, La Jolla, Calif., USA).

The chemotherapeutic agent is advantageously administered by low doses.

The mutant CyaA poplypeptide or the poplypeptide derivative thereof can also be administered with an adjuvant component, suitable for activating the innate immune response primed by a tumor in a patient.

In a particular embodiment of the invention, the adjuvant component is selected in the group of components consisting of nucleic acids, peptidoglycans, carbohydrates, peptides, cytokines, hormones and small molecules, wherein said adjuvant component is capable of signaling through pattern-recognition receptors (PRRs).

PRRs are known to mediate the innate immune response to pathogens, and to tumors, by recognition of so-called evolutionarily conserved signatures from pathogens (pathogen-associated molecule patterns, PAMPs). PRRs are present on a variety of immune cells including dendritic cells, natural killer cells, B cells, and also on some non immune cells such as epithelial cells or endothelial cells. PRRs and their involvement in the innate immune response are described in Pashine A. et al (Nature medicine supplement volume 11, N° 4, Apr. 2005).

In particular an adjuvant component for the activation of the innate immune response can target PRRs and therefore activate signaling through PRRs, wherein said PRRs encompass Toll-like receptors or nucleotide-binding oligomerization domain (NOD) or C type lectin.

In a particular embodiment of the invention, the adjuvant component is a Toll-like receptor (TLR) agonist. The Toll-like receptor agonist is especially formulated to efficiently activate the innate immune system of a patient. Said TLR agonist is capable of binding the TLR, i.e., is a ligand of the TLR and is furthermore capable of enhancing the immune response elicited under the control of said TLR.

For illustration, TLR agonists are selected from the group of TLR-9, TLR-8, TLR-3 and TLR-7 agonists. However agonists of other TLR receptors may be used to perform the invention, such as agonists of the TLR2, TLR4, TLR5 receptors.

The TLR agonist used in the invention can be a natural or a synthetic agonist. It can be a combination of different agonists of the same or of different toll-like receptors.

According to a particular embodiment of the invention, the TLR agonist is an immunostimulatory nucleotide sequence, especially a stabilized nucleotide sequence, for example stabilized as a result of structure modification such as phosphorothioate modification. The nucleotide sequence can also be protected against degradation by specific formulation. Especially liposome formulation thereof, e.g. liposome suspension, can be advantageous for the efficient administration of the immunostimulatory nucleotide sequence.

In a particular embodiment of the invention, the immunostimulatory nucleic acid sequence is a single-stranded RNA.

In a particular embodiment of the invention, the immunostimulatory nucleotide sequence comprises a CpG motif and especially is a CpG oligonucleotide (CpG ODNs). As an example of suitable CpG oligonucleotides the invention provides TLR-9 ligands such as Type A CpG ODN, i.e., CpG 2216 having nucleotide sequence 5'-GGGGGAC-GATCGTCGGGGGG-3' (SEQ ID NO:10) or Type B CpG ODN, i.e., CpG 1826 having nucleotide sequence 5'-TCCAT-GACGTTCCTGACGTT-3' (SEQ ID NO:11).

CpG oligonucleotide can be used after being complexed with DOTAP (Roche Manheim, Germany), in order to protect it against degradation and to facilitate its uptake.

According to another particular embodiment of the invention, the TLR agonist is a small molecule. Small molecules suitable as TLR agonists are for example imidazoquinoline amine derivatives, such as the one named R848 (resiquimod), i.e., 4-amino-2-ethoxymethyl-a, a, dimethyl-1-H-imidazo[4,5c]quinoline-1-ethanol available from Invivogen, as TLR-7 ligand, or the one named R837 (imiqimod) available from Aldara as TLR-7 agonist.

Other molecules suitable as TLR agonists are polyuridine (pU) as TLR-3 ligand, or polycytidylic acid (PlC) as TLR-7 ligand.

These molecules can be formulated to facilitate their uptake and/or to protect them from degradation. These molecules can also be prepared as a liposome formulation, especially as a liposome suspension, for administration to a patient.

According to another particular embodiment of the invention, the adjuvant component can be a cell-based adjuvant component. An example thereof is dendritic cells that are known to be able to prime lymphocyte response, such dendritic cells being possibly conditioned ex vivo prior to their administration, in order to increase their activity of stimulation of the T cell response. Dendritic cells can hence be stimulated with adjuvants interacting with the PRRs, including TLR ligands or agonists (Pashine A. et al Nature Medicine Supplement Volume 11, N°4, Apr. 2005 p S63-S68)

Alternatively, the polypeptide or polypeptide derivative according to the invention can be administered to the patient without an adjuvant.

Indeed the inventors have previously shown that CTL specific for the vectorized antigen can be primed in vivo after a single intravenous injection of the recombinant toxin, especially with no need to provide an heterologous adjuvant. These results and in particular the specific targeting of the epitope to myeloid dendritic cells enable to bypass the requirement for adjuvant and CD4+ T cell help.

Therefore, the invention also relates to the use of a mutant CyaA polypeptide recombined with a molecule and especially a peptide of interest for the preparation of a composition formulated for intravenous administration and enabling a CD8+ T cell immune response in vivo, said composition being free of a heterologous adjuvant. The invention also concerns this composition as such.

The present invention is further directed to therapeutic methods comprising administration of the mutant polypeptide or polypeptide derivative according to the invention to an animal or human patient suffering from a disease selected from neoplasia, cancers and infectious diseases selected from viral-, retroviral-, bacterial- or fungal-induced diseases.

The mutant polypeptide or polypeptide derivative can in particular be administered with a therapeutically active molecule and/or an adjuvant.

The mutant CyaA polypeptide or the polypeptide derivative, the therapeutically active molecule and/or an adjuvant can be administered together as part of a pharmaceutical composition which further comprises a pharmaceutically acceptable carrier or excipient(s).

Alternatively, the various types of molecules described herein to carry out the invention used, can be administered separately either simultaneously in time (especially for the mutant CyaA polypeptide or the polypeptide derivative and the adjuvant) or separately in time (especially for the mutant CyaA polypeptide).

The administration of the therapeutically active molecule can alternatively be carried out prior and after the administration of the mutant CyaA polypeptide or the polypeptide derivative and/or the adjuvant. It can also be sequential in time.

A particular regimen that may be adopted is a repeated administration protocol, especially in a protocol which encompasses two rounds or more of administration of at least one of the compounds selected from the mutant CyaA polypeptide or the polypeptide derivative, the therapeutically active agent and/or the adjuvant.

The invention is also directed to a pharmaceutical composition which comprises a mutant CyaA polypeptide or a polypeptide derivative according to the invention, a pharmaceutically acceptable carrier or excipient(s), and optionally an adjuvant and/or another therapeutically active molecule.

The invention is also directed to a kit of parts comprising the mutant CyaA polypeptide or the polypeptide derivative, a therapeutically active molecule and/or an adjuvant.

The compounds of the kit of parts or the composition of the invention can especially be given to the patient through intravenous administration, intratumoral administration or subcutaneous administration.

The kit of parts of the invention or the composition has the ability to target (i) the adaptive immune response, through the mutant CyaA polypeptide or the polypeptide derivative disclosed in the present application, (ii) to downregulate the regulatory immune response through the therapeutically active agent, and if the adjuvant is present, to target (iii) the innate component of the immune response, by activating said innate response through the adjuvant.

The invention also relates to a method of treatment of a patient in need thereof, either a human or an animal patient, comprising the step of administering the components of the kit of parts or of the composition herein disclosed.

The invention in particular also relates to a new immunogenic composition formulated for administration, especially intravenous administration, in an animal or human host, characterized in that it comprises a recombinant CyaA polypeptide derivative which comprises an antigen inserted in the catalytic domain.

The invention further relates to a pharmaceutical composition for administration in a human or an animal formulated for targeting a molecule of interest specifically to CD11b expressing cells characterized in that said molecule of interest is coupled to a mutant CyaA polypeptide as described herein.

In another specific embodiment, the pharmaceutical or immunogenic composition comprises a nucleic acid construction encoding the recombinant CyaA polypeptide derivative comprising a CyaA mutant polypeptide as defined herein coupled to a molecule of interest.

Furthermore, the invention also relates to the use of the immunogenic composition as defined above for the preparation of a vaccine or an immunotherapeutic composition, for administration to an animal or human host.

As used herein, the term "immunotherapeutic composition" relates to a composition which leads to an immunological response and which is associated to therapeutic treatments, such as treatment against neoplasia, cancers, viral infections, fungal infections, parasites infections or bacterial infections.

The invention further relates to a method to immunize an animal or human host, wherein said method comprises the steps of:
a) providing an immunogenic composition as defined above;
b) administering said immunogenic composition, preferably via intravenous route, to said host in order to promote an immune response.

In particular, the immunogenic compositions of the invention are capable of inducing or stimulating, in vivo or in vitro an immune cell response involving specifically dendritic cells. The immunogenic compositions of the invention can in particular be used for preventive or therapeutic vaccination of a patient.

As a consequence, in a specific embodiment, the immunogenic or pharmaceutical composition is advantageously devoid of priming adjuvants commonly used in the Art, such as aluminium hydroxide.

The invention further relates to a method for the preparation of a proteinaceous vector suitable for the delivery of a molecule of interest into a cell comprising binding the molecule of interest to a CyaA mutant polypeptide as defined herein.

The invention further relates to nucleic acid molecules, in particular DNA or RNA molecules, which encode a polypeptide or polypeptide derivative as defined above.

The invention is also directed to eukaryotic or prokaryotic cells which comprise the nucleic acid molecules as defined above.

The invention also relates to eukaryotic cells, preferably mammalian cells, which comprise a mutant CyaA polypeptide or polypeptide derivative as defined above. In a preferred embodiment, the cells are human cells.

The invention further relates to eukaryotic cells, preferably mammalian cells, transformed with the proteinaceous vector as defined above.

FIGURES

FIG. 1. Substitutions in the pore-forming and acylation domains synergize in decreasing the specific hemolytic activity of CyaA. (A) Sheep erythrocytes ($5 \times 10^8$/ml) in TNC buffer were incubated with 5 µg/ml of enzymatically active CyaA proteins at 37° C. After 30 min, aliquots of cells suspensions were washed repeatedly to remove unbound CyaA and used to determine the amount of cell-associated and cell-invasive AC activity. Hemolytic activity was measured after 5 hours of incubation as the amount of released hemoglobin by photometric determination ($A_{541}$). Activity of intact CyaA was taken as 100%. (B) Erythrocytes were incubated as above with the indicated concentrations of the enzymatically active CyaA-derived proteins for 30 min, washed, and the amount of cell-associated AC enzyme activity was determined. (C) The reduced cell binding activity of proteins with the K860R substitution was compensated for by increasing their concentration from 5 µg/ml to 25 µg/ml. Activities of CyaA/233OVA (CyaA/OVA) in the presence were taken as 100% value. The results represent average values from at least three independent experiments performed in duplicates. The asterisks indicate statistically significant differences (**, p<0.001) from activities of CyaA (FIG. 1A) or CyaA/OVA (FIG. 1C).

FIG. 2. CyaA/OVA/E570Q+K860R binds and translocates into CD11b$^+$ monocytes. (A) J774A.1 cells ($10^6$/ml) were incubated in D-MEM for 30 min at 4° C. with 2.5 µg/ml of CyaA, washed repeatedly, and the amount of cell-associated AC activity was determined in cell lyzates. To block the CD11b/CD18 receptor, cells were incubated for 30 min with the CD11b-specific antibody M1/70 (Exbio, Czech Republic) at a final concentration of 10 µg/ml prior to addition of CyaA (**, p<0.001). (B) The AC domain translocation capacity of constructs was assessed as the capacity to penetrate cells and convert cytosolic ATP to cAMP. J774A.1 cells were incubated with CyaA constructs for 30 minutes at 37° C. and the amounts of cAMP accumulated in cell lyzates were determined (41). As a control, the CD11b/CD18 receptor was blocked with the anti-CD11b antibody M1/70 as above. Membrane penetration of CD11b/CD18-bound and endocytosed toxin was controlled by using the doubly mutated CyaA/E570K+E581P variant, which is intact for receptor binding but fails to translocate the AC domain across cell membrane and elevate cytosolic cAMP concentrations (Vojtova-Vodolanova et al., 2009). (C) J774A.1 cells were loaded with the K$^+$ sensitive fluorescent probe PBFI/AM at 9.5 µM final external concentration and 25° C. for 45 min in the presence of Pluronic F-127 [0.05% (w/w)]. Cells were washed in HBSS before 3 µml$^{-1}$ of the indicated toxins were added. Fluorescence intensity ratio of PBFI (excitation wavelength 340, emission wavelengths 450 and 510 nm) reflecting the intracellular K$^+$ concentration was recorded every 15 s.

The right scale shows intracellular [K$^+$] values derived from calibration experiments (see Experimental procedures). No cell lysis, assessed as lactate dehydrogenase release, was observed within the time interval of the assay. Results representative of three independent determinations performed in duplicates are shown.

Figure 3:
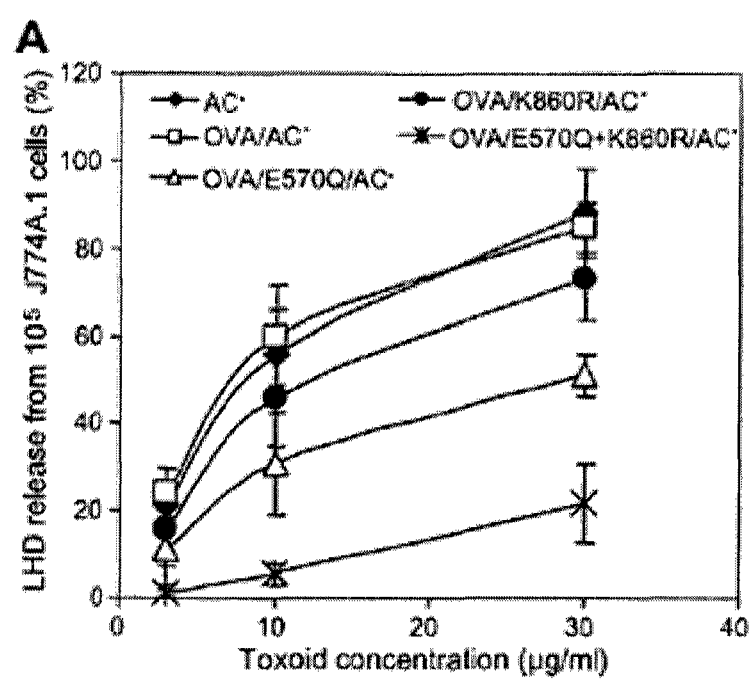
Figure 3:
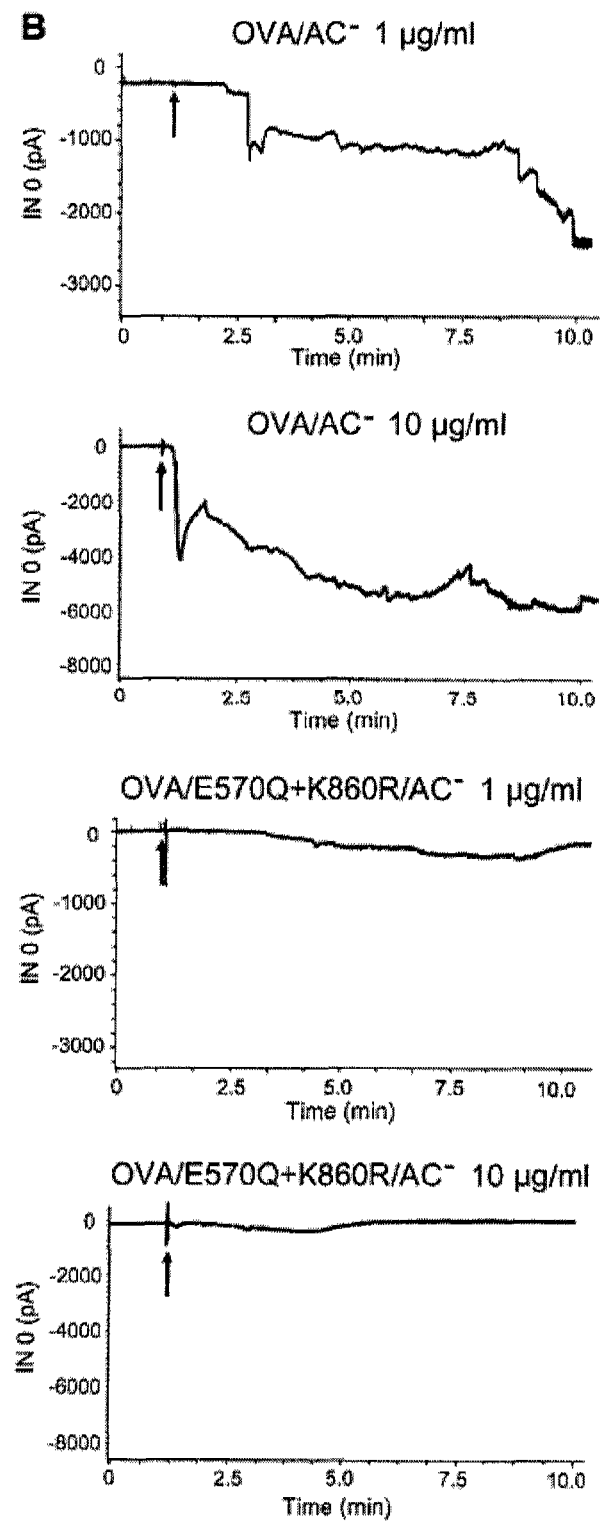

FIG. 3. E570Q+K860R toxoid does not permeabilize J774A.1 cells. (A) Lysis of J774A.1 cells was determined as the amount of lactate dehydrogenase released from 10$^5$ cells upon 3 h of incubation with 3, 10 and 30 μg ml$^{-1}$ of the indicated protein at 37% in DMEM without serum. The results represent the average of values obtained in two experiments performed in duplicates. (B) Whole-cell patch-clamp measurements were performed on single J774A.1 cells at room temperature exposed to 1 or 10 μg/ml of CyaA/233OVA/AC$^-$ or CyaA/233OVA/E570Q+K860R/AC$^-$ proteins as described in Materials and Methods. The shown curves are representative of six determinations in 3 independent experiments.

Figure 4:
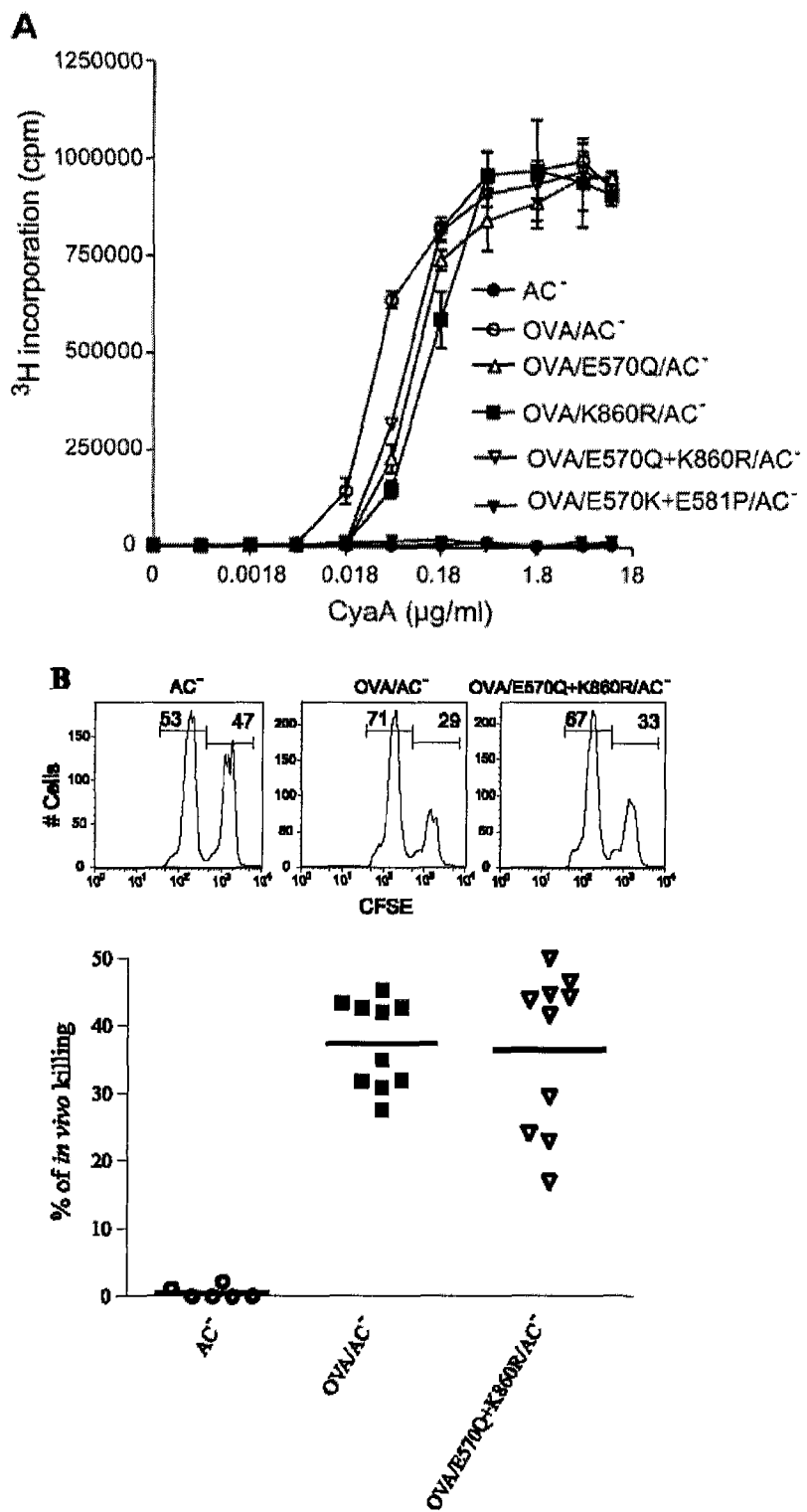

FIG. 4. Toxoid with E570Q+K860R substitutions delivers the OVA T-cell epitope for presentation by MHC class I molecules and induction of CD8$^+$ CTLs, (A) BMDC (3×10$^5$ cells/well) used as APCs were incubated in the presence of indicated concentrations (0 to 60 nM) of the toxoids harboring the OVA epitope or with mock CyaNAC$^-$. Upon co-culture for 24 hours with B3Z T cells (1×10$^6$ cells/well), IL-2 secretion by the stimulated B3Z cells was determined by the CTLL proliferation method. Results are expressed as Δcpm of incorporated [$^3$H]thymidine (cpm in the presence of toxoid cpm in the absence of toxoid)±SD and are representative of five independent experiments. (B) Analysis of the induction of OVA (SIINFEKL)-specific (SEQ ID NO:12) CTL responses by in vivo killing assay. On day 0, mice received 50 μg i.v. of mock AC$^-$ or OVA/AC$^-$ toxoids and on day 7, they were i.v. injected with a mixture (1:1) of OVA (SIINFEKL) (SEQ ID NO:12) peptide-loaded CFSE$^{high}$ and unloaded CFSE$^{low}$ splenocytes. The number of CFSE-positive cells remaining in the spleen after 20 h was determined by FACS analysis, as documented for one representative in vivo killing assay in the upper panel assembly of plots, where percentages of cells in the gates are indicated. The lower panel shows pooled results of in vivo killing assays for three independent experiments. Statistical significance was determined by the Student t test (p=0.75 for OVA/AC$^-$ vs. OVA/E570Q+K860R/AC$^-$).

Figure 5:
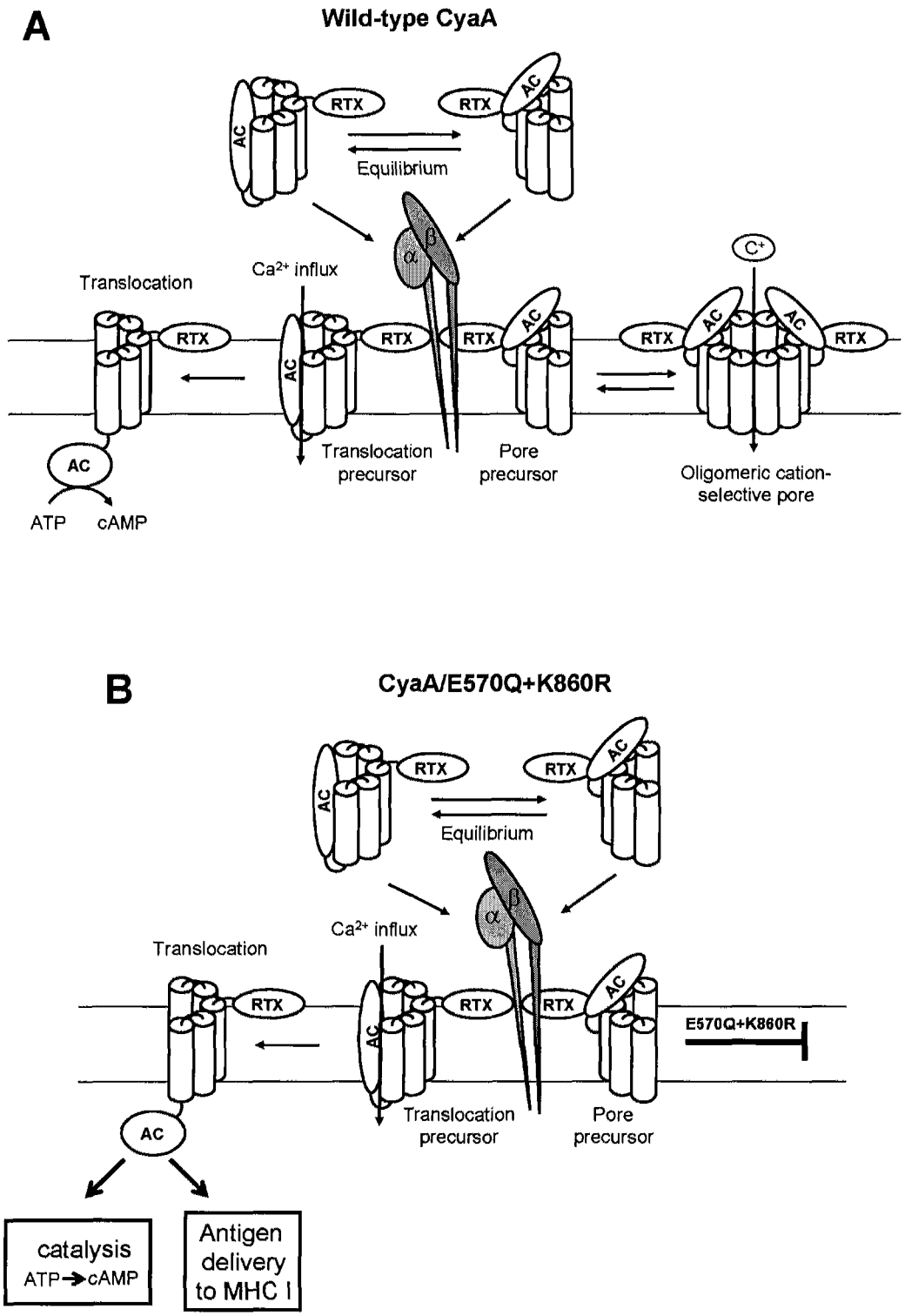

FIG. 5. Model of CyaA action on the membrane. (A) The model predicts an equilibrium between two conformers of CyaA in solution, each of them inserting into cell membrane in different a conformation. One would yield a monomeric CyaA translocation precursor, delivery of the AC domain into cytosol and concomitant influx of calcium ions into cells. The conformer would insert as pore precursor oligomerizing into a CyaA pore. (B) The synergic effect of the E570Q and K860R substitutions would selectively block the capacity of CyaA pore precursors to oligomerize into a pore, while the capacity of translocation precursors to deliver the AC domain across membrane would remain unaffected.

FIG. 6. Amino acid sequence of the *Bordetella pertussis* CyaA toxin (SEQ ID N°1)

FIG. 7. Amino acid sequence of the *Bordetella pertussis* CyaA/E570Q+K860R mutant (SEQ ID N°2)

FIG. 8. Amino acid sequence of the *Bordetella pertussis* CyaA/E570Q+K860R/AC$^-$ mutant (SEQ ID N°3)

FIG. 9. Amino acid sequence of the *Bordetella pertussis* CyaA/233OVA/E570Q+K860R/AC$^-$ mutant (SEQ ID N°4)

Figure 10:
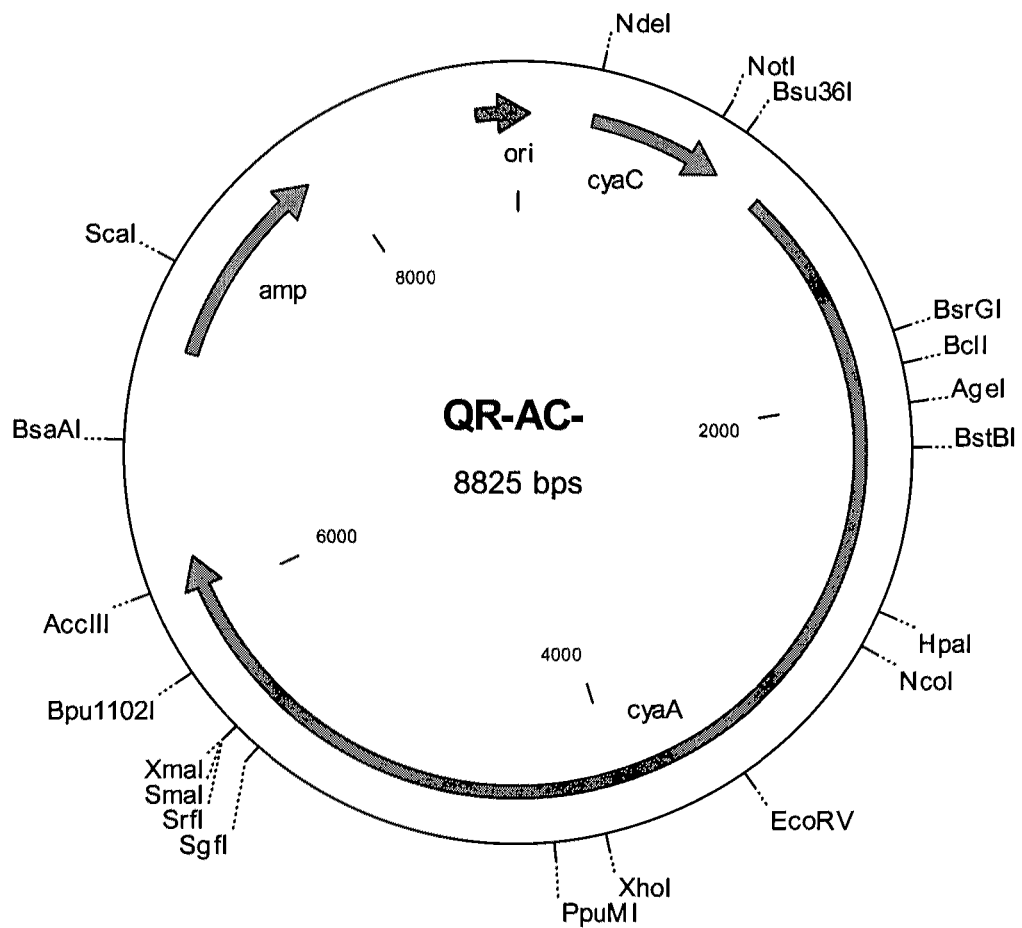

FIG. 10. Plasmid encoding the CyaA/E570Q+K860R/AC$^-$ mutant (QR-AC$^-$).

FIG. 11A-C. DNA sequence of the QR-AC- plasmid encoding the CyaA/E570Q+K860R/AC- mutant (SEQ ID N°5).

Figure 12:
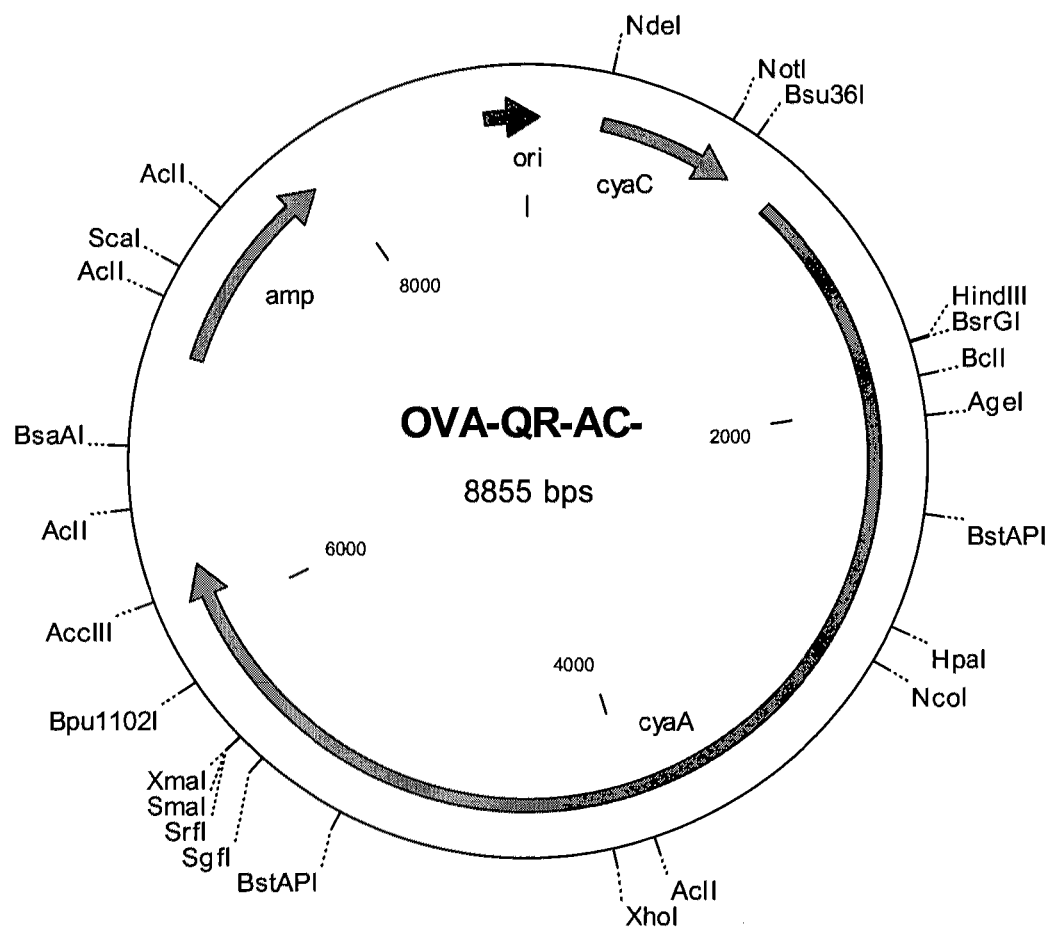

FIG. 12. Plasmid encoding the CyaA/233OVA/E570Q+K860R/AC$^-$ mutant (OVA-QR-AC$^-$).

FIG. 13A-C. DNA sequence of OVA-QR-AC- plasmid encoding the CyaA/233OVA/E570Q+K860R/AC- mutant (SEQ ID N°6).

FIG. 14. Amino acid sequence of the *Bordetella parapertussis* CyaA toxin (accession number CAB76450, SEQ ID N°7)

FIG. 15. Amino acid sequence of the *Bordetella hinzii* CyaA toxin (accession number AAY57201, SEQ ID N°8)

FIG. 16. Amino acid sequence of the *Bordetella bronchiseptica* CyaA toxin (accession number CAA85481, SEQ ID N°9)

EXAMPLES

Adenylate Cyclase Toxin Translocates Across Target Cell Membrane Without Forming a Pore Materials and Methods Construction, Production and Purification of CyaA proteins.

The modifications yielding CyaA/AC$^-$, CyaA/233OVA, CyaA/E570Q and CyaA/K860R constructs were previously described (13, 20, 21) and were introduced into CyaA/233OVA/AC$^-$ individually or in combination. The CyaA-derived proteins were produced in *E. coli* XL-1 Blue and purified close to homogeneity as previously described (29). During the hydrophobic chromatography, the resin with bound toxin was repeatedly washed with 60% isopropanol (30) to reduce the endotoxin content of CyaA samples below 100 IU/mg of protein, as determined by the LAL assay QCL-1000 (Cambrex).

An *Escherichia coli* XL1-Blue strain (Stratagene) containing the QR-AC$^-$ plasmid (FIG. 10) which encodes the CyaA/E570Q+K860R/AC$^-$ mutant was deposited on Mar. 18, 2009 at the CNCM (Collection Nationale de Cultures de Microorganismes, France) under the accession number CNCM I-4136 (FIG. 10). The DNA sequence of the QR-AC$^-$ plasmid (SEQ ID N°5) is disclosed in FIG. 11.

An *Escherichia coli* XL1-Blue strain (Stratagene) containing the OVA-QR-AC$^-$ plasmid (FIG. 12) which encodes the CyaA/233OVA/E570Q+K860R/AC$^-$ mutant was deposited on Mar. 18, 2009 at the CNCM (Collection Nationale de Cultures de Microorganismes, France) under the accession number CNCM I-4137. The DNA sequence of the OVA-QR-AC$^-$ plasmid (SEQ ID N°6) is disclosed in FIG. 13.

Cell Binding and Hemolytic Activities on Sheep Erythrocytes.

5×10$^8$ washed sheep erythrocytes in 50 mM Tris pH 7.4, 150 mM NaCl and 2 mM CaCl$_2$ (TNC buffer) were incubated at 37° C. with 5 μg/ml of CyaA proteins and cell binding, cell-invasive AC and hemolytic activities of CyaA were determined as described in detail previously (13). Significance of differences in activity values was analyzed using a one-way analysis of variance (ANOVA) with Bonferroni post-test (SigmaStat v. 3.11, Systat, San Jose, Calif.).

Macrophage Binding, Elevation of cAMP and Cell Lysis Capacities of CyaA.

J774.AI murine monocytes/macrophages (ATCC, number TIB-67) were cultured at 37° C. in a humidified air/CO$_2$ (19:1) atmosphere in RPMI medium supplemented with 10% (v/v) heat-inactivated fetal bovine serum, penicillin (100 IU ml$^{-1}$), streptomycin (100 μg ml$^{-1}$) and amphotericin B (250 ng ml$^{-1}$). Prior to assays, RPMI was replaced with Dulbecco's modified Eagle's medium (DMEM) (1.9 mM Ca2+) without FCS and the cells were allowed to rest in DMEM for 1 h at 37° C. in a humidified 5% $CO_2$ atmosphere (8). J774A.1 macrophages ($10^6$) were incubated in D-MEM with 2.5 µg/ml of CyaA variants for 30 min at 4° C., prior to removal of unbound toxin by three washes in D-MEM. Cells were lyzed with 0.1% Triton X-100 for determination of cell-bound AC activity. For intracellular cAMP assays, $10^5$ cells were incubated with CyaA for 30 minutes in D-MEM with 100 µM IBMX (3-isobutyl-1-methylxanthin), the reaction was stopped by addition of 0.2% Tween-20 in 100 mM HCl, samples were boiled for 15 min at 100° C., neutralized by addition of 150 mM unbuffered imidazol and cAMP was measured as described (29). To block the CD11b/CD18 receptor, cells were preincubated for 30 min on ice with the CD11b-specific blocking MAb M1/70 (Exbio, Czech Republic) at a final concentration of 10 µg/ml prior to addition of CyaA. Toxin-induced lysis of J774A.1 cells was determined using the CytoTox 96 kit assay (Promega) as the amount of lactate dehydrogenase released from $10^5$ cells in 3 hours of incubation with 10 µg/ml of the appropriate protein at 37° C. in D-MEM as described (8). Significance of differences in activity values was analyzed as above.

Patch Clamp Measurements.

Whole-cell patch-clamp measurements were performed on J774A.1 cells bathing in HBSS (140 mM NaCl, 5 mM KCl, 2 mM $CaCl_2$, 3 mM $MgCl_2$, 10 mM Hepes-Na, 50 mM glucose; pH 7.4). Fire-polished glass micropipettes with outer diameter of about 3 µm were filled with a solution of 125 mM potassium gluconate, 15 mM KCl, 0.5 mM $CaCl_2$, 1 mM $MgCl_2$, 5 mM EGTA, 10 mM HEPES-KOH pH 7.2. The resulting resistances of the microelectrodes were 3 to 5 MΩ. Cells were clamped at −40 mV, the data were filtered at 1 kHz and digitized at 2 kHz using Axopatch 200A amplifier, Digidata 1320A digitizer and PClamp-9 software package (Axon Instruments, Foster City, Calif.).

Determination of Decrease of Cytosolic K+ Concentration.

Cells grown on grass coverslips were washed in HBSS and loaded with 9.5 µM PFBI acetoxymethyl ester (PBFI/AM, Molecular Probes, Eugene, Oreg., USA) for 30 min at 25° C. in the presence of 0.05% (w/w) Pluronic F-127 (Sigma, St. Louis, Mo.), in the dark. Ratiometric measurement was performed at 25° C. using a FluoroMax-3 spectrofluorimeter (Jobin Yvon Horriba, France) equipped with DataMax software. Fluorescence intensity of PBFI (excitation wavelength 340, emission wavelengths 450 and 510 nm) was recorded every 15 s and the integration time for each wavelength was 3 s. The ratio of 450/510 nm wavelengths is shown. The observed area of coverslip mounted in the 1 cm cuvette was about 10 mm$^2$, corresponding to approximately $10^4$ cells. Calibration experiments were performed in 50 mM HEPES, pH 7.2, with varying concentrations of Potassium Acetate (10, 30, 60 or 140 mM) and Sodium Acetate (135, 115, 85 or 5 mM), respectively, on cells permeabilized for 30 min with 3 pM valinomycin or nigericin. Final intensity ratio (450/510 nm) is shown on right vertical axis of the plots.

Mice and Cell Lines

Female C57BL/6 obtained from Charles River Laboratories were kept under specific pathogen-free conditions and manipulated according to institutional guidelines. CTLL-2 cells were obtained from ATCC. B3Z, a CD8+ specific T cell hybridoma specific for the $K^b$ restricted OVA (SIINFEKL) epitope ("SIINFEKL" disclosed as SEQ ID NO: 12, was provided by N. Shastri (University of California, Berkeley) and maintained in the presence of 1 mg/ml G418 and 400 µg/ml hygromycin B in complete RPMI 1640 medium (Invitrogen Life Technologies) with 10% heat-inactivated FCS, 100 U/ml penicillin, 100 µg/ml streptomycin, and $5\times10^{-5}$ M 2-ME.

Antigen Presentation Studies.

Bone Marrow Dendritic Cells (BMDC, $3\times10^5$ per well) used as APCs were incubated in the presence of various concentrations (0 to 60 nM) of the recombinant CyaA/OVA/AC− carrying the OVA (SIINFEKL) epitope ("SIINFEKL" disclosed as SEQ ID NO: 121 or mock CyaNAC− and cocultured for 24 hours with B3Z T cells ($1\times10^5$ per well), selectively recognizing the OVA SIINFEKL/H-2$K^b$ ("SIINFEKL" disclosed as SEQ ID NO: 12) MHC class I complexes. After 18 h of culture, supernatants were frozen for at least 2 h at −80° C. The amount of IL-2 produced by the stimulated B3Z cells was then determined by the CTLL proliferation method. Briefly, $10^4$ cells of the IL-2-dependent CTLL line per well were cultured with 100 µl of supernatant in 200 µl of final volume. Twenty-four hours later, [$^3$H]-thymidine (50 µCi/well) was added and cells were harvested 6 h later with an automated cell harvester. Incorporated [$^3$H]-thymidine was detected by scintillation counting. Each point was done in duplicate and the experiment was repeated five times. Results are expressed in Δcpm of incorporated [$^3$H]-thymidine (cpm in the presence of toxoid cpm in the absence of toxoid).

In Vivo Killing Assay.

For CTL priming, mice were immunized by i.v. injection with 50 µg of recombinant CyaA/OVA/AC− carrying the OVA (SIINFEKL) epitope ("SIINFEKL" disclosed as SEQ ID NO: 121 or mock CyaA/AC−. Seven days after immunization, naive syngenic splenocytes were pulsed with OVA (SIINFEKL) peptide ("SIINFEKL" disclosed as SEQ ID NO: 12) (10 µg/ml) (30 min, 37° C.), washed extensively and labeled with a high concentration (1.25 µM) of carboxyfluoroscein succinimidyl ester (CFSE; Molecular Probes, Eugene, Oreg.). The nonpulsed control population was labeled with a low concentration (0.125 µM) of CFSE. CFSE$^{high}$- and CFSE$^{low}$-labeled cells were mixed in a 1:1 ratio ($5\times10^6$ cells of each population) and injected i.v. into mice. Spleen cells were collected 20 h after, washed and resuspended in FACS buffer (PBS supplemented with 1% BSA and 0.1% $NaN_3$). The number of CFSE-positive cells remaining in the spleen after 20 h was determined by FACS. The percentage of specific lysis was calculated as follows: percent specific lysis=100−[100×(% CFSE$^{high}$ immunized mice/% CFSE$^{low}$ immunized mice)/(% CFSE$^{high}$ naive mouse/% CFSE$^{low}$ naive mouse)].

Statistical Analysis:

Significance of differences in values was analyzed using a one-way analysis of variance (ANOVA) with Bonferroni post-test (SigmaStat v. 3.11, Systat, San Jose, Calif.).

Results

Combined Elimination of Negatively Charged Glutamate 570 and of Acylated Lysine 860 Ablates Cell-permeabilizing Capacity of CyaA.

The working model of CyaA action predicts that CyaA can be modified to lose its pore-forming (hemolytic) activity while preserving the capacity to deliver the AC domain into cytosol of target cells. To test this hypothesis, the inventors sought to produce CyaA constructs exhibiting as low hemolytic and cytolytic activities as possible, building on previous observation that the capacity of CyaA/AC− toxoids to lyze cells can be modulated both up or down by substitutions within the pore-forming domain (8, 12-14, 18). To enable assessment of target cell penetration also for the CyaNAC− toxoids, the inventors derived such mutants from a CyaA/233OVA toxin that was previously tagged by insertion of the SIINFEKL peptide ("SIINFEKL" disclosed as SEQ ID NO: 12) from ovalbumin (OVA). This CyaA variant was chosen as the insertion of reporter $K^b$-restricted CD8+ T-cell epitope at residue 233 does not affect the AC activity and allows to quantify translocation of the OVA/AC enzyme into cells as elevation of cytosolic cAMP. More importantly, presence of the OVA epitope allows to assess also the capacity of enzymatically inactive CyaA/233OVA/AC⁻ toxoids to deliver their OVA/AC⁻ domain into cytosol of CD11b⁺ antigen presenting cells (APC), as this enables proteasome processing and cell surface presentation of the OVA epitope on MHC Class I glycoproteins that can be determined as stimulation of OVA-specific CD8⁺ T cells, both in vitro and in vivo (20).

To generate CyaA/AC⁻ toxoids possibly lacking the cytolytic activity, the inventors combined the E570Q and K860R substitutions previously shown to reduce the specific hemolytic activity of CyaA on sheep erythrocytes, with the E570Q substitution having been found to reduce also the cytolytic activity of the CyaA/AC⁻ on CD11b⁺ J774A.1 monocytes (8, 13). These substitutions were engineered into CyaA/233OVA/AC⁻ individually and in combination and the specific hemolytic and cytolytic activities of resulting toxoids were compared using sheep erythrocytes as model CD11b⁻ target and J774A.1 as model CD11b⁺ target in parallel (Table I). In agreement with results obtained previously with toxoids lacking the OVA epitope (4, 8, 13, 21), under the used conditions the OVA/AC⁻ toxoids carrying individually the E570Q and K860R substitutions exhibited respectively a two-fold reduced (55±8) and nil (1±1) relative hemolytic activity on erythrocytes and the relative cytolytic activity of the E570Q toxoid towards CD11b-expressing J774A.1 cells was also reduced (37±10), as compared to OVA/AC⁻. In turn, as expected from results obtained with an enzymatically active K860R construct, despite the low hemolytic activity on CD11b⁻ erythrocytes, the K860R toxoid exhibited only a slightly reduced relative cytolytic activity on CD11b⁺ J774A.1 cells (72±22%), confirming that the structural defect caused by the K860R substitution was rescued by interaction with the CD11b/CD18 receptor (4). Nevertheless, when combined with E570Q, the K860R substitution exhibited a clear synergic effect in reducing the relative cytolytic activity of the E570Q+K860R construct towards J774A.1 cells down to 14±7%.

TABLE I

Cytolytic activities of OVA/AC⁻ and derivatives on sheep erythrocytes and J774A.1 macrophages.

| Protein | Lysis of erythrocytes (% of AC⁻)[a] | Lysis of J774A.1 cells (% of AC⁻)[b] |
|---|---|---|
| AC⁻ | 100 ± 5 | 100 ± 10 |
| OVA/AC⁻ | 93 ± 4 | 93 ± 12 |
| OVA/E570Q/AC⁻ | 55 ± 8** | 37 ± 10** |
| OVA/K860R/AC⁻ | 1 ± 1** | 72 ± 22** |
| OVA-L247Q-AC⁻ | 97 ± 3 | 41 ± 9 |
| OVA/E570Q + K860R/AC⁻ | 1 ± 1** | 14 ± 7** |
| OVA-E570Q-L247Q-AC⁻ | 50 ± 12 | 40 ± 11 |
| OVA-K860R-L247Q-AC⁻ | 1 ± 1 | 45 ± 11 |
| OVA-E570Q-K860R-L247Q-AC⁻ | 0 ± 1 | 16 ± 10 |

Table Legend
[a]Lysis of sheep erythrocytes was determined after 4.5 hours as the amount of hemoglobin released upon incubation of 5 × 10⁸ RBC at 37° C. in the presence of 2 mM Ca²⁺ with 5 μg/ml of the given protein (31). The hemolytic activity of CyaA/AC⁻ was taken as 100% activity. The results represent the average of values obtained in four independent experiments performed in duplicates ± S.D with two different protein preparations.
[b]Lysis of J774A.1 cells was determined as the amount of released lactate dehydrogenase from 10⁵ cells upon 3 hours of cell incubation with 10 μg/ml of the appropriate protein at 37° C. in D-MEM. J774A.1 cell lysis by CyaA/AC⁻ was taken as 100%. The results represent the average of values obtained in four separate experiments performed in duplicates ± S.D with two different protein preparations (*, $p < 0.05$; **, $p < 0.001$).

To enable quantification of capacity of the E570Q+K860R construct to deliver the AC domain into cytosol of cells, the E570Q and K860R substitutions were transferred into enzymatically active constructs derived from CyaA/233OVA (CyaA/OVA). These were produced and purified in the same way as the AC⁻ toxoids (not shown) and characterized for cell binding, hemolytic and AC translocation capacities on sheep erythrocytes. As shown in FIG. 1A and expected from results with toxins lacking the OVA epitope (4, 13, 21), the E570Q substitution had no impact on erythrocyte binding or the capacity of CyaA/OVA to deliver the AC domain into erythrocyte cytosol and selectively reduced only its relative hemolytic activity. As further expected (4), the K860R substitution significantly reduced the capacity of CyaA/OVA to bind and penetrate erythrocytes, causing a sharp reduction of the relative hemolytic and cell-invasive AC activities of the E570Q and E570Q+K860R mutants on erythrocytes.

It has to be noted, that the hemolytic activity of CyaA is a highly cooperative function of the amount of cell-associated CyaA (Hill number >3), suggesting that CyaA oligomerization is a prerequisite for pore formation (22). Therefore, to assess the impact of combined E570Q+K860R substitutions on the hemolytic activity, the loss of erythrocyte-binding capacity of the K860R constructs had to be compensated by increasing their concentration in the assay to 25 μg/ml (5 μg/ml for intact toxin), in order to achieve binding of equal amounts of all proteins to erythrocytes, as shown in FIG. 1C. Under these conditions the combination of E570Q and K860R substitutions exhibited a clear synergy in further reducing by a factor of two the already impaired hemolytic activities of constructs carrying the E570Q (~50%) and K860R substitutions (~30%) individually, as shown in FIG. 2C. This suggests that combination of the two substitutions affected the specific cell-permeabilizing capacity of CyaA.

Pore-forming Activity of CyaA is Dispensable for Membrane Translocation of the AC Domain.

In contrast to impact of the K860R substitution on toxin activity on erythrocytes, both the E570Q and K860R substitutions were previously found to have no effect on the capacity of CyaA to bind and penetrate J774A.1 monocytes expressing the CD11b/CD18 receptor (4, 8). Moreover, as documented in FIG. 2, when the two substitutions were combined in the same toxin molecule, the CyaA/OVA/E570Q+K860R construct exhibited an equal capacity to bind J774A.1 cells (FIG. 2A) and to deliver the AC domain into their cytosol to elevate cytosolic cAMP concentrations (FIG. 2B), as did intact CyaA. At the same time, however, the doubly mutated E570Q+K860R toxoid exhibited an about seven-fold reduced (14±7%) relative cytolytic capacity on these cells (cf. Table I). As shown in FIG. 2C, when compared with intact CyaA, the singly mutated E570Q and the doubly mutated E570Q+K860R constructs were importantly impaired in the capacity to elicit decrease of intracellular concentration of potassium ions ([K⁺]i) in toxin-treated J774A.1 cells. While no cell lysis was detected over 20 min by the assay for release of lactate dehydrogenase, the [K⁺]i of J774A.1 cells exposed to 3 μg ml⁻¹ of intact CyaA decreased from 140 mM to well below 30 mM already in 10 min upon toxin addition. In turn, when the same amounts of the ER570QiK860R constructs were used (3 μg ml⁻¹), the [K⁺]i levels in cells did not decrease below 100 mM (FIG. 2C). Indeed, efflux of potassium from cells was previously shown to be the hallmark of insertion of the CyaA pore precursors into cell membrane (32). This suggested that the combination of E570Q and K860R substitutions selectively impaired only the capacity of the toxoid to permeabilize J774A.1 cells and not its capacity to translocate the AC domain across cell membrane.

This conclusion was further supported by an importantly reduced relative cytolytic activity of the corresponding E570Q/AC- and E570Q+K860R/AC- toxoids, as discussed above (Table I) and documented in detail in FIG. 3A. The doubly mutated E570Q+K860R toxoid at 3 µg ml$^{-1}$ was essentially unable to provoke any detectable release of lactate dehydrogenase from J774A.1 cells in 3 h of incubation, while 20% of cells lysed in the presence of equal amounts of intact toxoid.

To test this, the inventors analyzed the cell-permeabilizing capacity of the E570Q+K860R construct in single whole cell patch-clamp experiments. Here again the AC$^-$ toxoids had to be used, in order to avoid the massive ruffling of J774A.1 cells provoked by toxin-generated cAMP (23). As shown in FIG. 3A by a representative recording of ion currents across the membrane of patch-clamped single J774A.1 cells exposed to 1 µg/ml of CyaA/OVA/AC$^-$, upon an initial lag of about 3 minutes the J774A.1 cells were progressively and massively permeabilized by CyaA/OVA/AC$^-$ and the currents across cell membrane reached −3,000 pA within 10 minutes. In contrast, as shown in FIG. 3B, exposure to the CyaA/OVA/E570Q+K860R/AC$^-$ reproducibly caused only a transient and minimal initial permeabilization of the cells, with currents across cell membrane not exceeding −200 pA and returning close to zero within 10 minutes after toxoid addition. Quite similar picture was observed when toxoid concentrations were elevated to 10 µg ml$^{-1}$, which was the concentration used for comparisons of relative cytolytic activity of toxoids summarized in Table I. The 10-fold increase of concentration from 1 to 10 µg ml$^1$ resulted in about twofold increase of the currents produced across cell membrane by OVA/AC−, while essentially no enhancement of cell permeabilization was observed even at the increased concentration of OVA/E570Q+K860R/AC− (note the expanded scale of y-axis for measurements at 10 µg ml$^{-1}$). The shown recordings were representative of at least six determinations from 3 independent experiments and demonstrate that the combination of the E570Q and K860R substitutions had a major impact on the capacity of the toxoid to permeabilize the membrane of J774A.1 cells. Given that the enzymatically active version of the same construct was fully capable to translocate the AC domain into J774A.1 cells (cf. FIG. 2B), these results strongly suggest that the cell-permeabilizing (pore-forming) activity of CyaA was not required for AC domain translocation across cellular membrane.

Membrane-permeabilizing Activity of CyaA is Dispensable for Delivery of Passenger Antigens to the Cytosolic MHC Class I Pathway.

Since the assay for cytosolic cAMP could not be used for assessment of cell penetration capacity of the AC$^-$ toxoids, the surrogate assay for their capacity to deliver the reporter OVA epitope to the cytosolic processing site of the MHC class I antigen presentation pathway was used (7, 24). Towards this end, the inventors determined the capacity of C57BL/6 mouse bone marrow-derived dendritic cells (BMDCs), loaded with the toxoids, to stimulate IL-2 release by B3Z T cells that selectively recognize the complex of K$^b$ MHC class I molecules with the SIINFEKL (OVA) peptide ("SIINFEKL" disclosed as SEQ ID NO: 12) on APCs. It has, indeed, been previously shown that the capacity of CyaA/AC-toxoids to translocate the AC domain across the cytoplasmic membrane into cytosol of BMDCs is essential for the capacity of the toxoids to promote presentation of the delivered OVA epitope in complex with the H-2Kb MHC class I molecules. This, in turn, is essential for specific in vitro stimulation of cytotoxic T cells to occur (29). Nevertheless, it was important to confirm here that delivery of the OVA epitope for proteasome processing and subsequent presentation was due to AC domain translocation into cytosol of BMDCs across their cytoplasmic membrane, and was not due to sampling of the added antigen by fluid phase uptake, or endocytosis. For this purpose, a doubly mutated non-translocating OVA/E570K+E581 P/AC-toxoid variant was used, which bears a combination of charge-reversing and a-helix-breaking substitutions of glutamates 570 and 581 in the transmembrane domain of CyaA (33). This construct was previously found to exhibit a full capacity to bind CD11b/CD18-expressing cells (cf. FIG. 2A), while its capacity to translocate the AC domain across target cell membrane was ablated by the combination of E570K and E581P substitutions (cf. FIG. 2B).

As shown in FIG. 4A, the B3Z hybridoma cells were effectively stimulated upon co-incubation with BMDCs loaded with the OVA/E570Q/AC− and OVA/E570Q+K860R/AC− toxoids. In contrast, no B3Z stimulation was observed upon co-incubation with BMDCs loaded with the OVA/E570K+E581P/AC− toxoid defective in AC domain translocation across cell membrane. Moreover, the OVA/E570Q/AC$^-$ and OVA/E570Q+K860R/AC$^-$ toxoids induced stimulation of the B3Z lymphocytes by APCs in vitro with as high efficiency as intact OVA/AC$^-$ toxoid. These results confirm that the E570Q+K860R double mutant was fully capable to translocate its AC domain into BMDC cytosol for processing and presentation of the OVA epitope by K$^b$ MHC class I molecules, while being essentially unable to permeabilize the J774A.1 cells. These results suggest that the cell-permeabilizing (pore-forming) activity of CyaA was neither required for AC domain translocation across cellular membrane, nor did it play any role in the capacity of CyaA to deliver passenger epitopes into APC cytosol.

To corroborate the observed in vitro antigen delivery capacity of the non-cytolytic toxoids, the inventors assessed their in vivo capacity to prime OVA-specific cytotoxic CD8$^+$ T lymphocytes (CTL), 50 µg of the various OVA-toxoids were injected intravenously into C57BL/6 mice and one week later the OVA-specific CTL responses were assessed in immunized mice by an in vivo killing assay. C57BL/6 mice received i.v. injection of a mixture (1:1) of OVA (SIINFEKL) (SEQ ID NO: 12) peptide-loaded CFSE$^{high}$ and unloaded CFSE$^{low}$ splenocytes, followed one day later by FACS analysis of CFSE-labeled cells. As shown in FIG. 4B, immunization of mice with the mock toxoid did not induce any SIINFEKL-specific ("SIINFEKL" disclosed as SEQ ID NO: 12) in vivo CTL activity. In turn, immunization with the E570Q+K860R toxoid induced the same OVA-specific in vivo CTL killing response as the unmutated toxoid used as positive control, with the slight difference in the values of mean response to the intact and doubly mutated toxoids not being statistically significant (p=0.065). These results show that the cell-permeabilizing activity of CyaA was dispensable for the in vivo capacity of the CyaA/233OVA/AC$^-$ toxoids to deliver an AC-inserted passenger antigen into cytosol of APCs.

Discussion

The inventors demonstrate here that translocation of the AC domain of CyaA across the membrane of CD11b/CD18 receptor-expressing myeloid target cells does not depend on the capacity of the toxin to form pores and permeabilize the cellular membrane.

As summarized in the model proposed in FIG. 5, the inventors have previously reported that balance between the two activities of CyaA can be shifted by mutations or alternative acylation of CyaA. Enhancement of the pore-forming (hemolytic) activity at the expense of the capacity to deliver AC into cells was, indeed, observed upon lysine substitutions of glutamates 509, 516 and 581 (13, 18), or upon blocking of AC translocation by the 3D1 monoclonal antibody (MAb) (25). In turn, a shift in the opposite direction was observed for the recombinant r-Ec-CyaA, acylated in E. coli by palmitoleyl (C16:1) residues, as compared to the native (C16:0) palmitylated Bp-CyaA produced by *B. pertussis*. The r-Ec-CyaA was found to exhibit about four-fold reduced hemolytic activity and about ten-fold lower pore-forming activity in planar lipid bilayers than Bp-CyaA (12), while both CyaA forms were equally active in penetrating cellular membrane and translocating the AC domain into erythrocytes (17, 26). Moreover, recently the CyaA/E570Q construct was found to exhibit a full capacity to deliver the AC domain into both erythrocytes and J774A.1 macrophages, while exhibiting reduced hemolytic activity and lower specific pore-forming capacity in planar lipid bilayers than intact CyaA, with the CyaA/E570Q/AC⁻ toxoid exhibiting a two-fold reduced cytolytic activity on J774A.1 cells (8, 13).

Despite the above mentioned and the many mutant CyaAs that the inventors characterized, the question remained whether formation of a membrane pore by CyaA is required for translocation of the AC domain across the membrane of CD11b-expressing cells. It is worth mentioning that, based on previous comparisons of haemolytic potency of the intact r-Ec-CyaA with that of the native Bp-CyaA purified from *B. pertussis*, the specific haemolytic activity of the here described r-Ec-CyaA/OVA/E570Q+K860R/AC− toxoid on sheep erythrocytes would be reduced by about three orders of magnitude. The residual specific cytolytic activity of r-Ec-CyaA/OVA/E570Q+K860R/AC− on CD11b-expressing cells would then be estimated to be about 50-fold lower than that of Bp-CyaA, while the specific capacity of both proteins to deliver the AC domain into these cells would be the same (using intact r-Ec-CyaA as 100% invasive AC activity standard for comparisons). The here described CyaA/233OVA/E570Q+K860R mutant is the first construct with an importantly reduced capacity to permeabilize cells that remains fully capable of translocating the AC domain across cellular membrane. This shows that on its way to cell cytosol the translocating AC domain can bypass the cation-selective pore formed by CyaA.

The mode and path of AC domain translocation across cellular membrane, however, remain to be defined in more detail. Given the differing effects of substitutions of glutamates 509, 516, 570 and 581 on the pore-forming and AC delivery activities of CyaA (8, 13, 18), where the balance between the two activities can be almost entirely shifted in either direction by specific substitutions, the amphipathic helices harboring these glutamate residues appear to be involved in both activities of CyaA in an alternative manner. This is supported by the effect of combined E509K+E516K substitution, which yields a hyper-hemolytic CyaA unable to deliver the AC domain into cells (8, 18), while the here described E570Q+K860R combination yields the opposite, an essentially non-cytolytic CyaA that is fully competent to translocate the AC domain into J774A.1 cells (CD11b⁺).

These observations further corroborate the proposed model that the two membrane activities of CyaA would depend on different conformers inserting into membrane, one yielding translocation of the AC domain by toxin monomers and the other leading to formation of oligomeric CyaA pores (13, 18). It is proposed that the transmembrane segments harbouring the critical glutamate residues 509, 516, 570 and 581 can participate in formation of an oligomeric and cation-selective cytolytic pore only if the membrane-inserted pore precursor conformer has the AC domain located outside the cell. In the AC translocating conformer, the same transmembrane segments would adopt a different conformation in the membrane, being potentially obtruded and prevented from entering CyaA oligomers by the polypeptide linking the C-terminal end of the AC domain to transmembrane segments. Support for this interpretation can be deduced from results obtained by Gray and co-workers (25). These authors showed that deletion of the AC domain together with the segment linking it to the pore-forming domain (up to residue 489), or binding of the 3D1 antibody that blocks membrane translocation of the terminal AC domain segment located between residues 373 and 399, importantly enhances the pore-forming (haemolytic) activity of the toxin. This is likely to be due to imposing a conformation on the transmembrane segments of CyaA that is favourable for formation of the otigomeric pores. It remains to be defined what CyaA segments outside of the pore-forming domain are involved in AC domain translocation across membrane. Given the requirement for its structural integrity (27), the large RTX repeat domain (residues 1006 to 1706) is likely to be taking part in AC translocation into cells. It would be sized enough (700 residues) to form a hydrophilic translocation interface within cellular membrane that might allow passage of an unfolded AC domain across the membrane without a concomitant formation of a real cell-permeabilizing pore. Alternatively, CyaA might promote formation of inverted nonlamellar (inverted hexagonal phase) lipid structures (28), which might potentially take part in a well sealed protein-lipid interface through which the AC domain could slide into cell cytosol.

CyaA was, indeed, previously shown to promote formation of inverted non-lamellar (inverted hexagonal phase) lipid structures (28). These might potentially take part in formation of a well-sealed protein-lipid interface, thus allowing translocation of the AC domain across membrane in the absence of cell permeabilization. Formation of non-lamellar lipid structures is favoured in cholesterol-enriched lipid rafts and CyaA was, indeed, recently found to mobilize into rafts in complex with its receptor CD11b/CD18. Moreover, the inventors have recently shown that AC domain translocation across membrane is accomplished only upon relocation of CyaA into rafts (L., Bumba, J., Masin, R., Fiser, and P., Sebo, submitted). Intriguingly, translocation of the catalytic subunit of diphtheria toxin (DT) across the cell cytoplasmic membrane was also previously found to occur without detectable cell permeabilization, when DT was pulsed into cells by low pH upon binding to a truncated GPI-anchored DT receptor (34). The authors did not examine whether the GPI-anchored DT receptor localized into lipid rafts, but this is highly likely. It is, hence, tempting to speculate that the specific lipid composition of the raft membrane may support translocation of different protein toxins into target cells without the need for formation of a true protein conducting pore permeabilizing the cell.

Last not least, a practical discovery reported herein is that the CyaA/E570Q+K860R/AC⁻ toxoid with the much reduced cell-permeabilizing (cytolytic) activity, remains fully active in antigen delivery into CD11b⁺ APCs. This is of importance in the light of its potential use as enhanced safety profile tool for delivery of tumor-specific antigens in second generation of CyaA/AC⁻-derived vaccines for immunotherapy of cancer.

REFERENCES

1. Vojtova J, Kamanova J, Sebo P (2006) *Bordetella* adenylate cyclase toxin: a swift saboteur of host defense. *Curr Opin Microbiol* 9: 69-75.
2. Glaser P, Sakamoto H, Bellalou J, Ullmann A, Danchin A (1988) Secretion of cyclolysin, the calmodulin-sensitive adenylate cyclase-haemolysin bifunctional protein of *Bordetella pertussis*. *Embo J* 7: 3997-4004.
3. Rose T, Sebo P, Bellalou J, Ladant D (1995) Interaction of calcium with *Bordetella pertussis* adenylate cyclase toxin.

Characterization of multiple calcium-binding sites and calcium-induced conformational changes. *J Biol Chem* 270: 26370-26376.

4. Masin J, et al. (2005) Acylation of lysine 860 allows tight binding and cytotoxicity of *Bordetella* adenylate cyclase on CD11b-expressing cells. *Biochemistry* 44: 12759-12766.

5. Guermonprez P, et al. (2001) The adenylate cyclase toxin of *Bordetella pertussis* binds to target cells via the alpha(M) beta(2) integrin (CD11b/CD18). *J Exp Med* 193: 1035-1044.

6. Gordon V M, Leppla S H, Hewlett E L (1988) Inhibitors of receptor-mediated endocytosis block the entry of *Bacillus anthracis* adenylate cyclase toxin but not that of *Bordetella pertussis* adenylate cyclase toxin. *Infect Immun* 56: 1066-1069.

7. Schlecht G, Loucka J, Najar H, Sebo P, Leclerc C (2004) Antigen targeting to CD11b allows efficient presentation of CD4+ and CD8+ T cell epitopes and in vivo Th1-polarized T cell priming. *J Immunol* 173: 6089-6097.

8. Basler M, Masin J, Osicka R, Sebo P (2006) Pore-forming and enzymatic activities of *Bordetella pertussis* adenylate cyclase toxin synergize in promoting lysis of monocytes. *Infect Immun* 74: 2207-2214.

9. Khelef N, Zychlinsky A, Guiso N (1993) *Bordetella pertussis* induces apoptosis in macrophages: role of adenylate cyclase-hemolysin. *Infect Immun* 61: 4064-4071.

10. Morova J, Osicka R, Masin J, Sebo P (2008) RTX cytotoxins recognize {beta}2 integrin receptors through N-linked oligosaccharides. *Proc Natl Acad Sci USA*.

11. Paccani S R, et al. (2008) Suppression of T-lymphocyte activation and chemotaxis by the adenylate cyclase toxin of *Bordetella pertussis*. *Infect Immun* 76: 2822-2832.

12. Benz R, Maier E, Ladant D, Ullmann A, Sebo P (1994) Adenylate cyclase toxin (CyaA) of *Bordetella pertussis*. Evidence for the formation of small ion-permeable channels and comparison with HlyA of *Escherichia coli*. *J Biol Chem* 269: 27231-27239.

13. Basler M, et al. (2007) Segments crucial for membrane translocation and pore-forming activity of *Bordetella* adenylate cyclase toxin. *J Biol Chem* 282: 12419-12429.

14. Hewlett E L, Donato G M, Gray M C (2006) Macrophage cytotoxicity produced by adenylate cyclase toxin from *Bordetella pertussis*: more than just making cyclic AMP! *Mol Microbiol* 59: 447-459.

15. Fayolle C, Sebo P, Ladant D, Ullmann A, Leclerc C (1996) In vivo induction of CTL responses by recombinant adenylate cyclase of *Bordetella pertussis* carrying viral CD8+ T cell epitopes. *J Immunol* 156: 4697-4706.

16. Rogel A, Hanski E (1992) Distinct steps in the penetration of adenylate cyclase toxin of *Bordetella pertussis* into sheep erythrocytes. Translocation of the toxin across the membrane. *J Biol Chem* 267: 22599-22605.

17. Havlicek V, et al. (2001) Mass spectrometric analysis of recombinant adenylate cyclase toxin from *Bordetella pertussis* strain 18323/pHSP9. *J Mass Spectrom* 36: 384-391.

18. Osickova A, Osicka R, Maier E, Benz R, Sebo P (1999) An amphipathic alpha-helix including glutamates 509 and 516 is crucial for membrane translocation of adenylate cyclase toxin and modulates formation and cation selectivity of its membrane channels. *J Biol Chem* 274: 37644-37650.

19. Fiser R, et al. (2007) Third activity of *Bordetella* adenylate cyclase (AC) toxin-hemolysin. Membrane translocation of AC domain polypeptide promotes calcium influx into CD11b+ monocytes independently of the catalytic and hemolytic activities. *J Biol Chem* 282: 2808-2820.

20. Osicka R, et al. (2000) Delivery of CD8(+) T-cell epitopes into major histocompatibility complex class I antigen presentation pathway by *Bordetella pertussis* adenylate cyclase: delineation of cell invasive structures and permissive insertion sites. *Infect Immun* 68: 247-256.

21. Basar T, of al. (1999) The conserved lysine 860 in the additional fatty-acylation site of *Bordetella pertussis* adenylate cyclase is crucial for toxin function independently of its acylation status. *J Biol Chem* 274: 10777-10783.

22. Szabo G, Gray M C, Hewlett E L (1994) Adenylate cyclase toxin from *Bordetella pertussis* produces ion conductance across artificial lipid bilayers in a calcium- and polarity-dependent manner. *J Biol Chem* 269: 22496-22499.

23. Kamanova J, et al. (2008) Adenylate cyclase toxin subverts phagocyte function by RhoA inhibition and unproductive ruffling. *J Immunol* 181: 5587-5597.

24. Guermonprez P, Ladant D, Karimova G, Ullmann A, Leclerc C (1999) Direct delivery of the *Bordetella pertussis* adenylate cyclase toxin to the MHC class I antigen presentation pathway. *J Immunol* 162: 1910-1916.

25. Gray M C, et al. (2001) Translocation-specific conformation of adenylate cyclase toxin from *Bordetella pertussis* inhibits toxin-mediated hemolysis. *J Bacteriol* 183: 5904-5910.

26. Hackett M, et al. (1995) Hemolytic, but not cell-invasive activity, of adenylate cyclase toxin is selectively affected by differential fatty-acylation in *Escherichia coli*. *J Biol Chem* 270: 20250-20253.

27. Iwaki M, Ullmann A, Sebo P (1995) Identification by in vitro complementation of regions required for cell-invasive activity of *Bordetella pertussis* adenylate cyclase toxin. *Mol Microbiol* 17: 1015-1024.

28. Martin C, et al. (2004) Membrane restructuring by *Bordetella pertussis* adenylate cyclase toxin, a member of the RTX toxin family. *J Bacteriol* 186: 3760-3765.

29. Karimova G, Pidoux J, Ullmann A, Ladant D (1998) A bacterial two-hybrid system based on a reconstituted signal transduction pathway. *Proc Natl Acad Sci USA* 95: 5752-5756.

30. Franken K L, et al. (2000) Purification of his-tagged proteins by immobilized chelate affinity chromatography: the benefits from the use of organic solvent. *Protein Expr Purif* 18: 95-99.

31. Bellalou J, Sakamoto H, Ladant D, Geoffroy C, Ullmann A (1990) Deletions affecting hemolytic and toxin activities of *Bordetella pertussis* adenylate cyclase. *Infect Immun* 58: 3242-3247.

32. Gray M. C., et al. (1998) Distinct mechanisms for K+ efflux, intoxication, and hemolysis by *Bordetella pertussis* AC toxin. *J Biol CHem* 273:18260-18267

33. Vojvova-Vodolanova J., et al. (2009) Oligomerization is involved in pore formation by *Bordetella pertussis* adenylate cyclase toxin. *FASEB J* 23:2331-2343

34. Lanzrein M., et al. (1996) GPI anchored diphteria toxin receptor allows membrane translocation of the toxin without detectable ion channel activity. *EMBO J.* 15:725-734

The invention claimed is:

1. An isolated or purified polypeptide comprising a *Bordetella pertussis* CyaA sequence having at least 99% identity with SEQ ID NO: 1, in which:
   a) the glutamic acid residue at position 570 of SEQ ID NO: 1 has been substituted by another amino acid residue selected from the group consisting of Gln, Asn, Met, Thr, Ser, Gly, Arg, Lys, Val, Leu, Cys, Ile, and Asp, and
   b) the lysine residue at position 860 of SEQ ID NO: 1 has been substituted by another amino acid residue selected from the group consisting of Gln, Asn, Met, Thr, Ser, Gly, Arg, Val, Leu, Cys, and Ile.

2. The polypeptide of claim 1, wherein the polypeptide is combined with one or more molecules of interest for eliciting an immune response comprising an amino acid sequence of a poliovirus antigen, an HIV virus antigen, an influenza virus antigen, a choriomeningitis virus antigen, a tumor antigen, or comprising or consisting of an amino acid sequence of any of these antigens which comprises at least one epitope.

3. The polypeptide of claim 2, wherein the molecule of interest suitable for eliciting an immune response is inserted into a permissive site of the polypeptide, thereby preserving the capacity of said polypeptide to translocate its N-terminal adenylate cyclase enzyme domain into target cells.

4. The polypeptide of claim 2, wherein each of said amino acid sequences suitable for eliciting an immune response is covalently or non-covalently coupled to an amino acid residue of said polypeptide.

5. The polypeptide of claim 2, which elicits a T-cell immune response and/or a B-cell immune response in a host in need thereof.

6. The polypeptide of claim 1, further comprising an adjuvant or a therapeutically active molecule.

7. The polypeptide of claim 1, whose adenylate cyclase activity in cells is partly or totally suppressed as compared to that of the *Bordetella pertussis* CyaA toxin.

8. The polypeptide of claim 7, wherein the polypeptide has essentially lost its adenylate cyclase enzyme activity.

9. The polypeptide of claim 8, wherein said partial or total suppression of adenylate cyclase activity is achieved by insertion of a dipeptide between the amino acid residues at positions 188 and 189 of SEQ ID NO: 1.

10. A pharmaceutical composition comprising a polypeptide according to claim 1 and a pharmaceutically acceptable carrier.

11. The pharmaceutical composition of claim 10, further comprising an adjuvant or a therapeutically active molecule.

* * * * *

UNITED STATES PATENT AND TRADEMARK OFFICE
CERTIFICATE OF CORRECTION

| | | |
|---|---|---|
| PATENT NO. | : 9,222,143 B2 | Page 1 of 1 |
| APPLICATION NO. | : 13/257569 | |
| DATED | : December 29, 2015 | |
| INVENTOR(S) | : Sebo et al. | |

It is certified that error appears in the above-identified patent and that said Letters Patent is hereby corrected as shown below:

On the Title Page, item 63 should include:

"Related U.S. Application Data

Continuation-in-part of U.S. Application No. 12/409,324, filed on March 23, 2009, now U.S. Patent 8,017,132.".

In the Specification

Col. 1, line 12, replace "claims the priority" with -- is a continuation-in-part --.

Signed and Sealed this
Eighth Day of March, 2016

Michelle K. Lee
*Director of the United States Patent and Trademark Office*